US011696990B2

(12) United States Patent
Martin et al.

(10) Patent No.: US 11,696,990 B2
(45) Date of Patent: Jul. 11, 2023

(54) MONITORING RESPIRATORY PRESSURE THERAPY

(71) Applicant: RESMED PARIS SAS, Moissy-Cramayel (FR)

(72) Inventors: Dion Charles Chewe Martin, Sydney (AU); Clancy John Dennis, Potts Point (AU); Benjamin John Leavens, Sydney (AU); Etienne Veschambre, Sydney (AU); Stuart Wishart, Sydney (AU)

(73) Assignee: RESMED PARIS SAS

( * ) Notice: Subject to any disclaimer, the term of this patent is extended or adjusted under 35 U.S.C. 154(b) by 297 days.

(21) Appl. No.: 16/947,081

(22) Filed: Jul. 17, 2020

(65) Prior Publication Data

US 2020/0345961 A1 Nov. 5, 2020

Related U.S. Application Data

(63) Continuation of application No. 15/752,725, filed as application No. PCT/AU2016/050736 on Aug. 12, 2016, now Pat. No. 10,751,490.

(30) Foreign Application Priority Data

Aug. 14, 2015 (AU) .................................. 2015903275

(51) Int. Cl.
*A61M 16/00* (2006.01)
*A61M 16/08* (2006.01)
(Continued)

(52) U.S. Cl.
CPC .... *A61M 16/0051* (2013.01); *A61M 16/0066* (2013.01); *A61M 16/026* (2017.08);
(Continued)

(58) Field of Classification Search
CPC .............. A61M 16/00; A61M 16/0051; A61M 16/0066; A61M 16/0069; A61M 16/024;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

JP H08512218 A 12/1996
JP 3701670 B2 7/2005
(Continued)

OTHER PUBLICATIONS

International Search Report for Application No. PCT/AU2016/050736 dated Jan. 3, 2017.
(Continued)

*Primary Examiner* — Joseph D. Boecker
(74) *Attorney, Agent, or Firm* — Botos Churchill IP Law LLP

(57) ABSTRACT

Methods and apparatus provide automated circuit disconnection monitoring such as for a respiratory apparatus or system. Disconnection of a patient circuit, including a patient interface and air delivery circuit, may be detected and a message or alarm activated. In some versions, detecting occurrences of circuit disconnection event(s), such as by a processor, may be based on an instantaneous disconnection parameter as a function of a disconnection setting. The disconnection setting may be determined based on patient circuit type. The instantaneous disconnection parameter may be determined from detected pressure and flow rate, and may be, for example, a conductance value or an impedance value. Disconnection events may be qualified by one or more detected respiratory indicators. In some cases, instantaneous (Continued)

impedance or conductance may be used to assess re-connection of a patient circuit, detection of flow starvation, determine breath shape for triggering and cycling and to detect patient or circuit obstructions.

32 Claims, 27 Drawing Sheets

(51) Int. Cl.
| | |
|---|---|
| A61M 16/06 | (2006.01) |
| A61M 16/10 | (2006.01) |
| A61M 16/12 | (2006.01) |
| A61M 16/16 | (2006.01) |
| A61M 16/20 | (2006.01) |

(52) U.S. Cl.
CPC ......... *A61M 16/08* (2013.01); *A61M 16/0057* (2013.01); *A61M 16/06* (2013.01); *A61M 16/0633* (2014.02); *A61M 16/0666* (2013.01); *A61M 16/0683* (2013.01); *A61M 16/0825* (2014.02); *A61M 16/0858* (2014.02); *A61M 16/105* (2013.01); *A61M 16/109* (2014.02); *A61M 16/1055* (2013.01); *A61M 16/1095* (2014.02); *A61M 16/12* (2013.01); *A61M 16/16* (2013.01); *A61M 16/161* (2014.02); *A61M 16/206* (2014.02); *A61M 16/208* (2013.01); *A61M 2016/003* (2013.01); *A61M 2016/0027* (2013.01); *A61M 2016/1025* (2013.01); *A61M 2202/0208* (2013.01); *A61M 2202/0225* (2013.01); *A61M 2205/14* (2013.01); *A61M 2205/15* (2013.01); *A61M 2205/18* (2013.01); *A61M 2205/21* (2013.01); *A61M 2205/33* (2013.01); *A61M 2205/3331* (2013.01); *A61M 2205/3365* (2013.01); *A61M 2205/3368* (2013.01); *A61M 2205/3375* (2013.01); *A61M 2205/3553* (2013.01); *A61M 2205/3561* (2013.01); *A61M 2205/3592* (2013.01); *A61M 2205/362* (2013.01); *A61M 2205/3606* (2013.01); *A61M 2205/42* (2013.01); *A61M 2205/505* (2013.01); *A61M 2205/6018* (2013.01); *A61M 2205/6054* (2013.01); *A61M 2205/70* (2013.01); *A61M 2205/8206* (2013.01); *A61M 2230/205* (2013.01)

(58) Field of Classification Search
CPC ........ A61M 16/026; A61M 2016/0027; A61M 2016/0033; A61M 2016/0036; A61M 2016/0039; A61B 5/0826; A61B 5/4818
See application file for complete search history.

(56) References Cited

U.S. PATENT DOCUMENTS

| | | | | |
|---|---|---|---|---|
| 5,259,373 | A * | 11/1993 | Gruenke | A61M 16/06 128/204.23 |
| 5,640,149 | A | 6/1997 | Campbell | |
| 5,881,717 | A | 3/1999 | Isaza | |
| 6,138,675 | A | 10/2000 | Berthon-Jones | |
| 6,142,952 | A * | 11/2000 | Behbehani | A61B 5/7253 600/533 |
| 6,152,129 | A | 11/2000 | Berthon-Jones | |
| 6,240,921 | B1 | 6/2001 | Brydon | |
| 6,532,959 | B1 | 3/2003 | Berthon-Jones | |
| 6,603,006 | B2 | 8/2003 | Coppi et al. | |
| 6,668,824 | B1 | 12/2003 | Isaza et al. | |
| 7,866,944 | B2 | 1/2011 | Kenyon et al. | |
| 7,984,712 | B2 | 7/2011 | Soliman et al. | |
| 8,424,520 | B2 | 4/2013 | Thiessen | |
| 8,603,006 | B2 | 12/2013 | Mulqueeny et al. | |
| 8,636,479 | B2 | 1/2014 | Barton et al. | |
| 8,638,014 | B2 | 1/2014 | David | |
| 8,733,349 | B2 | 5/2014 | Bath et al. | |
| 8,746,248 | B2 | 6/2014 | Jafari et al. | |
| 10,751,490 | B2 * | 8/2020 | Martin | A61M 16/0066 |
| 2003/0213491 | A1 * | 11/2003 | Berthon-Jones | A61M 16/0069 128/204.21 |
| 2004/0016431 | A1 | 1/2004 | Preveyraud | |
| 2005/0061321 | A1 | 3/2005 | Jones | |
| 2006/0086357 | A1 | 4/2006 | Soliman et al. | |
| 2007/0135757 | A1 | 6/2007 | Acker et al. | |
| 2009/0044808 | A1 | 2/2009 | Guney et al. | |
| 2009/0326403 | A1 * | 12/2009 | Bassin | A61B 5/087 128/204.23 |
| 2010/0000534 | A1 | 1/2010 | Kooij et al. | |
| 2010/0147303 | A1 | 6/2010 | Jafari et al. | |
| 2011/0196251 | A1 | 8/2011 | Jourdain et al. | |
| 2012/0037159 | A1 | 2/2012 | Mulqueeny et al. | |
| 2012/0179061 | A1 | 7/2012 | Ramanan et al. | |
| 2013/0263854 | A1 | 10/2013 | Taylor et al. | |
| 2015/0020801 | A1 | 1/2015 | Frame et al. | |
| 2015/0059755 | A1 * | 3/2015 | Bassin | A61M 16/026 128/204.23 |
| 2015/0128941 | A1 * | 5/2015 | Holley | A61M 16/0833 128/203.14 |
| 2015/0144130 | A1 | 5/2015 | O'Donnell et al. | |
| 2015/0182710 | A1 | 7/2015 | Berry Ann et al. | |
| 2015/0320338 | A1 * | 11/2015 | Kane | A61B 5/4818 600/533 |
| 2017/0100554 | A1 | 4/2017 | Adametz et al. | |
| 2018/0015244 | A1 | 1/2018 | Isaza | |

FOREIGN PATENT DOCUMENTS

| | | |
|---|---|---|
| WO | 1998004310 A1 | 2/1998 |
| WO | 9841268 A1 | 9/1998 |
| WO | 2004073778 A1 | 9/2004 |
| WO | 2005063328 A1 | 7/2005 |
| WO | 2006074513 A1 | 7/2006 |
| WO | 2006130903 A1 | 12/2006 |
| WO | 2009052560 A1 | 4/2009 |
| WO | 2010091462 A1 | 8/2010 |
| WO | 2010135785 A1 | 12/2010 |
| WO | 2011006199 A1 | 1/2011 |
| WO | 2012116133 A1 | 8/2012 |
| WO | 2012171072 A1 | 12/2012 |
| WO | 2013020167 A1 | 2/2013 |
| WO | 2014030098 A1 | 2/2014 |
| WO | 2014128668 A1 | 8/2014 |
| WO | 2014162283 A1 | 10/2014 |
| WO | 2015063218 A2 | 5/2015 |
| WO | 2016103122 A1 | 6/2016 |
| WO | 2016145483 A1 | 9/2016 |

OTHER PUBLICATIONS

Notification of Transmittal of International Preliminary Report on Patentability for International Application No. PCT/AU2016/050736, dated Aug. 7, 2017.
NZ First Examination Report dated Feb. 25, 2020.
West, Respiratory Physiology, Lippincott Williams & Wilkins, 9th edition published 2011.
Office Action for Chinese Patent Application No. 201680048334.3, dated May 17, 2021.
Office Action for European Patent Application No. 16836263.0, dated Mar. 18, 2021.
Office Action for Japanese Patent Application No. 2018-507535, dated Oct. 13, 2020.
Office Action for Japanese Patent Application No. 2018-507535, dated Sep. 24, 2021.
Naijie , et al., "Critical Care Medicine of Integrated Traditional Chinese and Western Medicine", p. 582, Huazhong University of Science and Technology Press, 2009.

(56) References Cited

OTHER PUBLICATIONS

Venegas, "Equivalent Circuit Analysis of High-Frequency Ventilators Including a New High-Impedance Flow-Interrupting Ventilator", IEEE Transactions on Biomedical Engineering, vol. BME-33, No. 4, 1986, pp. 420-427.

* cited by examiner

FIG. 7F(ii)

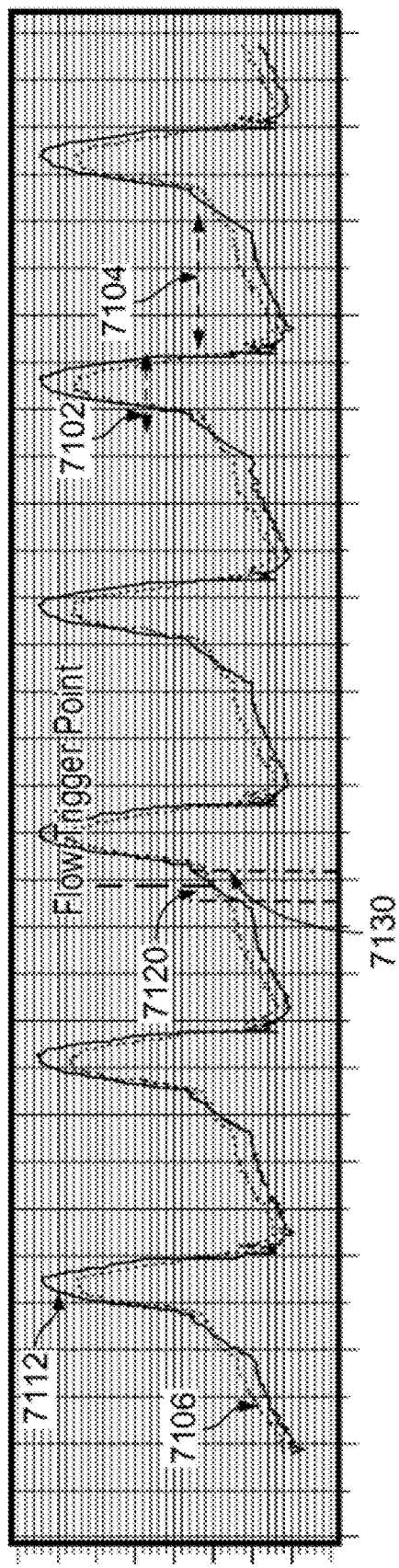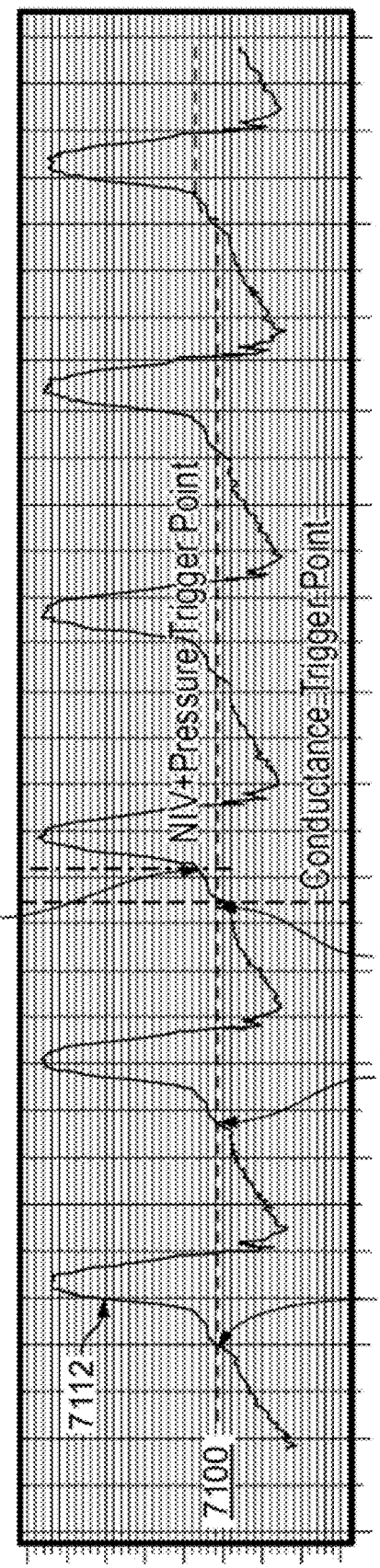
FIG. 7G(i)  FIG. 7G(ii)

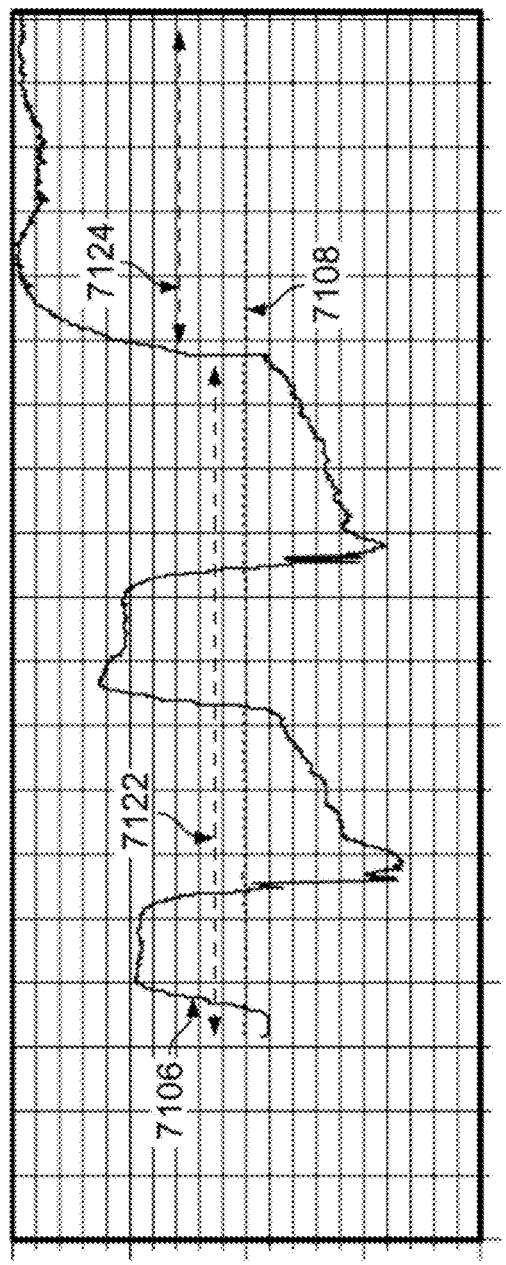
FIG. 7H(i)
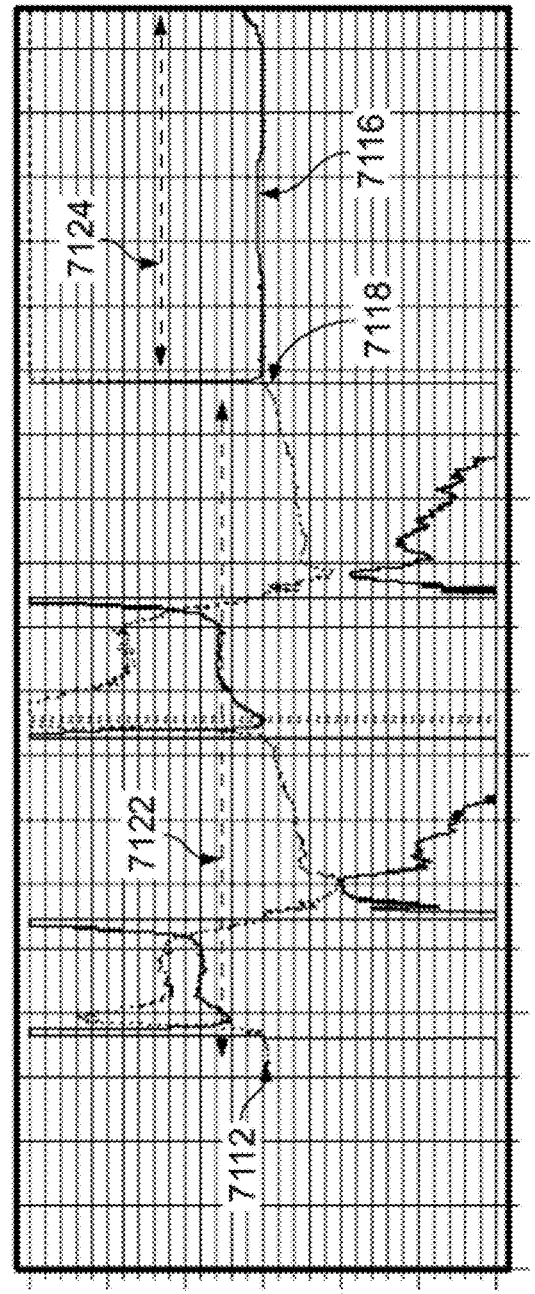
FIG. 7H(ii)

MONITORING RESPIRATORY PRESSURE THERAPY

I. CROSS REFERENCE TO RELATED APPLICATIONS

This application is a continuation of U.S. patent application Ser. No. 15/752,725 filed Feb. 14, 2018, which is a national phase entry under 35 U.S.C. § 371 of International Application No. PCT/AU2016/050736 filed Aug. 12, 2016, published in English, which claims priority from Australian Provisional Patent Application No. 2015903275 filed on Aug. 14, 2015, all of which are incorporated herein by reference.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use. In particular the present technology relates using determinations of conductance or impedance in a patient circuit to monitor the delivery of therapy in a respiratory apparatus.

1.2 Description of the Related Art

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs, and are therefore characterised by abnormal blood gas tensions. Respiratory failure may encompass some or all of the following disorders.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory portion of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising.

1.2.2 Respiratory Pressure Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory insufficiency, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

A treatment system may include a circuit disconnection detection system that detects when a patient has been disconnected from the system. Examples are the Smart-Start™ feature described in U.S. Pat. No. 6,240,921 and present in ResMed CPAP and VPAP devices such as the ResMed AirSense 10 CPAP device. Depending on the patient's disorder, the appropriate action may be to automatically (a) suspend therapy, (b) pause normal therapy and enter a non-therapeutic stand-by condition with a variety of aims including to conserve water or supplementary gas delivery, prevention of rebreathing, detect subsequent re-connection, or (c) to sound an alarm in combination with either of (a) or (b), or in combination with maintenance of normal therapy if possible.

An accidental disconnection along the gas flow path to a ventilator dependent patient can be life-threatening, therefore such systems may require an alarm to notify caretakers or clinicians when a patient has become disconnected. Many volume ventilators include low pressure alarms that can be configured to detect patient disconnection with certain circuit configurations and therapy modes. This relies on the device suffering a drop in pressure due to a disconnected circuit substantially below that pressure present when connected, including during situations of background leak or strong patient efforts. Such disconnection detection systems may commonly not detect de-cannulation, such as with small tracheostomy tubes commonly used in infants and small children, or with an un-cuffed cannula associated with high leak, or with turbine-based ventilators which may not suffer a pressure drop due to their high flow capability, or with high resistance mouthpieces. There is a general trend towards non-invasive ventilation, in which even high leaks are tolerated without loss of pressure. With such wide variation in patients, circuits, ventilation modes, and ventilation technology, no single-modality disconnection alarm (such as low pressure, high flow, high volume, and low volume) will reliably detect disconnection in all circumstances.

A re-connection of the patient, if detected, may be cause to resume previous therapy or other action appropriate to ensure the well-being of the patient while connected to the device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT" II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT" nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Humidifier

Delivery of a flow of air without humidification may cause drying of airways. The use of a humidifier with an RPT device and the patient interface produces humidified gas that minimises drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.4 Data Management

There may be clinical reasons to obtain data to determine whether the patient prescribed with respiratory pressure therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that detect a patient circuit disconnection.

Some versions of the present technology include a method of detecting an occurrence of a circuit disconnection event for a patient circuit of a respiratory apparatus configured to supply a flow of pressurised air to a patient via the patient circuit. The method may include determining a disconnection setting based on a type of the patient circuit. The method may include detecting pressure and flow rate of the pressurised air flow with one or more sensors. The method may include calculating in a processor an instantaneous disconnection parameter based on the detected pressure and flow rate. The method may include detecting with the processor the occurrence of a circuit disconnection event based on the instantaneous disconnection parameter as a function of the disconnection setting.

In some versions, the instantaneous disconnection parameter may be a conductance value. The instantaneous disconnection parameter may be an impedance value. The disconnection setting may be disconnection threshold. The detecting the occurrence of a circuit disconnection event may include comparing the calculated instantaneous disconnection parameter to the disconnection threshold.

The disconnection setting may be a profile, and the detecting the occurrence of a circuit disconnection event may include comparing a plurality of calculated instantaneous disconnection parameters to the profile.

In some versions, the method may include receiving patient specific information by the respiratory apparatus and using the patient specific information in determining the disconnection setting. The patient specific information may include one or more of a patient's age, weight, height and patient type. Optionally, the disconnection setting may be determined from a look-up table stored in a memory of the respiratory apparatus. The method may include determining the type of the patient circuit. The method may include receiving the type of the patient circuit via a user interface of the respiratory apparatus. The type of the patient circuit may include a configuration of an air circuit. The configuration of the air circuit may be at least one of vented, non-vented, single limb and double limb, single limb, and double limb. The type of the patient circuit may include a type of a patient interface. The type of the patient interface may be at least one of invasive, non-invasive, vented, and non-vented.

In some cases, the method may include, upon the detection of an occurrence of a circuit disconnection event, signalling that a circuit disconnection event has occurred. The method may include, upon the detection of an occurrence of a circuit disconnection event, generating a response to the disconnection event. Generating a response to the disconnection event may include activating a message on a display of the respiratory apparatus. Generating a response to the disconnection event may include activating a disconnection alarm.

In some cases, a user interface of the respiratory apparatus is configured with a user control to mute the disconnection alarm for a predetermined period of time.

The method may include continuously detecting the occurrence of the circuit disconnection event for a predetermined time limit prior to generating a response to the disconnection event. The predetermined time limit may be a set time between 5 seconds and 60 seconds. The predetermined time limit may be a predetermined number of breaths. The predetermined time limit may be adjustable via a user interface of the respiratory apparatus. The method may include calculating the instantaneous disconnection parameter at least once per breath. The method may include calculating the instantaneous disconnection parameter from an inspiration phase of each breath. The method may include calculating the instantaneous disconnection parameter at least once from an inspiration phase of each breath and at least once from an expiration phase of each breath. The method may include calculating the instantaneous disconnection parameter at predetermined time intervals.

In some version, the method may include determining a sensitivity setting, and adjusting the disconnection setting based on the sensitivity setting. The method may include determining the sensitivity setting according to a default sensitivity setting based on the type of the patient circuit. The method may include determining the sensitivity setting from a testing phase. The testing phase may occur prior to the respiratory apparatus providing respiratory therapy to the patient. The testing phase may occur whilst the respiratory apparatus is providing respiratory therapy to the patient. The method may include, upon the detection of an occurrence of a circuit disconnection event from the testing phase, generating a response to the disconnection event. The sensitivity setting may be selectable via a user interface of the respiratory apparatus from a predetermined range of settings. The predetermined range of settings may include values between 1% and 100%. The predetermined range of settings may include values between 5% and 95% provided in 5% increments. In some cases, a value of the sensitivity setting for detection of a circuit disconnection event may be provided on a display of the respiratory apparatus.

In some versions, the method may include, upon detecting the occurrence of a circuit disconnection event, qualifying the detected occurrence by monitoring for respiratory indicators. In some cases, if a respiratory indicator indicates that the patient is still connected to the patient circuit, the method may include qualifying the detected occurrence of the circuit disconnection event as false. In some cases, if a respiratory indicator does not indicate that the patient is still connected to the patient circuit, the method may include qualifying the detected occurrence of the circuit disconnection event as true. The respiratory indicators may consist of one or more of: (i) an expiratory flow indicative of expiratory effort; (ii) an inspiratory flow indicative of inspiratory effort; (iii) a difference in the instantaneous disconnection parameter calculated from an inspiration phase compared to the instantaneous parameter calculated from an expiration phase; (iv) a comparison of the instantaneous disconnection parameter to a calculated variance of previous values of the instantaneous disconnection parameter; and (v) a variation in the instantaneous disconnection parameter over time within a breath phase.

In some versions, the method may include, upon detecting the occurrence of a circuit disconnection event, comparing the detected flow rate to a predetermined threshold to confirm the occurrence of the disconnection event. The method may include detecting re-connection of the patient circuit to the patient following the detection of the occurrence of a circuit disconnection event. The re-connection of the patient circuit to the patient may be detected by comparing the instantaneous disconnection parameter to a second threshold. The re-connection of the patient circuit to the patient may be detected by detection of an abrupt change in the instantaneous disconnection parameter.

Some versions of the present technology may include a method of detecting an occurrence of a circuit disconnection event in a patient circuit of a respiratory apparatus configured to supply a flow of pressurised air to a patient via the patient circuit. The method may include repeatedly detecting pressure and flow rate of the pressurised air flow with one or more sensors. The method may include repeatedly calculating in a processor an instantaneous disconnection parameter based on the detected pressure and flow rate. The method may include comparing with the processor successive instantaneous disconnection parameters to determine a level of variability in the instantaneous disconnection parameter over time. The method may include detecting with the processor the occurrence of a circuit disconnection event based on the level of variability. In some versions, the instantaneous disconnection parameter may be a conductance value. The instantaneous disconnection parameter may be an impedance value.

Some versions of the present technology may include a system for detecting an occurrence of a circuit disconnection event for a patient circuit of a respiratory apparatus configured to supply a flow of pressurised air to a patient via the patient circuit. The system may include a controller having at least one processor to access data representing pressure and flow rate of the pressurised air flow detected by one or more sensors. The controller may be configured to determine a disconnection setting based on a type of the patient circuit. The controller may be configured to calculate an instantaneous disconnection parameter based on the accessed data representing pressure and flow rate. The controller may be configured to detect the occurrence of a circuit disconnection event based on the instantaneous disconnection parameter as a function of the disconnection setting. T the instantaneous disconnection parameter may be a conductance value. The instantaneous disconnection parameter may be an impedance value.

In some versions of the system, the disconnection setting may be a disconnection threshold and the controller may be configured to compare the calculated instantaneous disconnection parameter to the disconnection threshold to detect the occurrence of a circuit disconnection event. The disconnection setting may be a profile, and the controller may be configured to compare a plurality of the calculated instantaneous disconnection parameters to the profile to detect the occurrence of a circuit disconnection event. The controller may be further configured to receive patient specific information and to use the patient specific information to determine the disconnection setting. The patient specific information may include one or more of a patient's age, weight, height and patient type. The controller may be configured to determine the disconnection setting based on a look-up table stored in a memory of the respiratory apparatus.

The controller may be configured to determine the type of the patient circuit. The controller may be configured to receive the type of the patient circuit via a user interface of the respiratory apparatus. The type of the patient circuit may include a configuration of an air circuit, and the configuration of the air circuit may be at least one of invasive, non-invasive, vented, non-vented, single limb and double limb. The controller may be configured to provide an indication of a circuit connection status on a user interface of the respiratory apparatus. The controller may be configured to generate a response to the circuit disconnection event by activating a message on a user interface of the respiratory apparatus. The controller may be configured to generate a response to the circuit disconnection event by activating a disconnection alarm. The controller may be configured to mute the disconnection alarm for a predetermined period of time in response to user activation of a user control of a user interface of the respiratory apparatus. The controller may be configured to refrain from activating the disconnection alarm until the occurrence of a circuit disconnection event is continuously detected for a predetermined time limit. The predetermined time limit may be a set time between 5 seconds and 60 seconds. The predetermined time limit may be a predetermined number of breaths. The predetermined time limit may be adjustable.

In some versions, the controller may be configured to calculate the instantaneous disconnection parameter at least once per breath. The controller may be configured to calculate the instantaneous disconnection parameter from an inspiration phase of each breath. The controller may be configured to calculate the instantaneous disconnection parameter at least once from an inspiration phase of each breath and at least once from an expiration phase of each breath. The controller may be configured to calculate the instantaneous disconnection parameter at predetermined time intervals.

In some versions, the controller may be further configured to determine a sensitivity setting and to adjust a sensitivity of the disconnection setting based on the sensitivity setting. The controller may be configured to determine a default sensitivity setting based on the type of the patient circuit. The controller may be configured to determine the sensitivity setting from a testing phase. The testing phase may occur prior to the respiratory apparatus providing respiratory therapy to the patient. The testing phase may occur whilst the respiratory apparatus may be providing respiratory therapy to the patient. Activation of a disconnection alarm may be disabled during the testing phase. The sensitivity setting may be selectable via a user interface of the respiratory apparatus from a predetermined range of settings. The predetermined range of settings may include values between 1% and 100%. The predetermined range of settings may include values between 5% and 95% provided in 5% increments. Optionally, a sensitivity setting indication may be provided on a display of the respiratory apparatus. The sensitivity setting indication may provide an indication of whether a disconnection event is detected with the determined sensitivity setting.

In some version of the system, the controller may be further configured to qualify a determined occurrence of a circuit disconnection event by monitoring for respiratory indicators that indicate the patient may be still connected to the patient circuit contemporaneously with the determined occurrence of a circuit disconnection event. The controller may be configured to qualify the determined occurrence of the circuit disconnection event as false, if a respiratory indicator indicates that the patient may be still connected to the patient circuit. The controller may be configured to qualify the determined occurrence of the circuit disconnection event as true, if a respiratory indicator does not indicate that the patient may be still connected to the patient circuit. The respiratory indicators consist of one or more of: (i) an expiratory flow indicative of expiratory effort; (ii) an inspiratory flow indicative of inspiratory effort; (iii) a difference in the instantaneous disconnection parameter calculated from an inspiration phase compared to the instantaneous parameter calculated from an expiration phase; (iv) a comparison of the instantaneous disconnection parameter to a calculated variance of previous values of the instantaneous disconnection parameter; and (v) a variation in the instantaneous disconnection parameter over time within a breath phase.

The controller may be further configured to compare the flow rate to a predetermined threshold to confirm the occurrence of the circuit disconnection event after detecting the occurrence of a circuit disconnection event. The controller may be further configured to detect re-connection of the patient circuit to the patient following the detection of the occurrence of a circuit disconnection event. The re-connection of the patient circuit to the patient may be detected by comparing the instantaneous disconnection parameter to a second threshold. The re-connection of the patient circuit to the patient may be detected by detection of an abrupt change in the instantaneous disconnection parameter.

In some cases, a respiratory apparatus may include any one or more of the aforementioned systems, and may further include the one or more sensors, and a pressure generator configured to supply the flow of pressurised air.

Some versions of the present technology may include a respiratory therapy system configured to provide respiratory therapy to a patient breathing in successive breathing cycles including an inspiration phase and an expiration phase. The system may include a pressure generator configured to supply a flow of pressurised air. The pressure generator may be configured to couple with a patient interface via an air circuit to deliver the pressurised air from the pressure generator to the patient. The system may include at least one sensor configured to provide one or more signals indicative of a pressure and a flow rate of the pressurised air flow. The system may include a controller including a processor configured to repeatedly detect values of instantaneous pressure and values of instantaneous flow rate from the one or more signals from the at least one sensor. The controller including a processor may be configured to repeatedly calculate instantaneous conductance values based on the values of instantaneous pressure and values of instantaneous flow rate. The controller including a processor may be configured to monitor changes in the instantaneous conductance values over time to detect an occurrence of a respiratory event within the system.

In some cases, the respiratory event may be an obstruction. The obstruction may be detected when the instantaneous conductance falls below a predetermined threshold. The obstruction may be detected when the instantaneous conductance remains unchanged over time. The obstruction may occur in the air circuit, the patient interface, or the patient's airways.

In some cases, the respiratory event may be flow starvation during a volume target mode. The flow starvation may be detected as a function of a profile of the instantaneous conductance values over the inspiration phase of a breathing cycle. The flow starvation may be detected when instantaneous conductance values are higher at an early-to-mid-inspiration portion of the inspiration phase compared to an end portion of the inspiration phase. The flow starvation may be detected by a comparison of (a) an instantaneous conductance value calculated from an inspiration phase of a breathing cycle and (b) a conductance threshold. The flow starvation may be detected when the instantaneous conductance value calculated from the inspiration phase of a breathing cycle exceeds the conductance threshold. In some cases, upon detection of the respiratory event, the controller may be configured to activate a message to indicate the occurrence of the respiratory event.

Some versions of the present technology may include a respiratory therapy system configured to provide respiratory therapy to a patient breathing in successive breathing cycles including an inspiration phase and an expiration phase. The system may include a pressure generator configured to supply a flow of pressurised air. The pressure generator may be configured to couple with a patient interface via an air circuit to deliver the pressurised air from the pressure generator to the patient. The system may include at least one sensor configured to provide one or more signals indicative of a pressure and a flow rate of the pressurised air flow. The system may include a controller including a processor configured to repeatedly detect values of instantaneous pressure and values of instantaneous flow rate from the one or more signals from the at least one sensor. The system may include a controller including a processor configured to repeatedly calculate instantaneous conductance values based on the values of instantaneous pressure and values of instantaneous flow rate. The system may include a controller including a processor configured to monitor changes in the instantaneous conductance values over time to monitor the respiratory therapy.

In some versions, the controller may determine a level of difference in an instantaneous conductance value calculated from a beginning portion of the inspiration phase and an instantaneous conductance value calculated from an end portion of the inspiration phase. The controller may be configured to adjust a rise time setting based on the level of difference. The controller may be configured to adjust a peak inspiratory flow setting based on the level of difference. The controller may be configured to monitor the instantaneous conductance value over time to determine an inspiration phase and an expiration phase of one or more breathing cycles. The controller may be configured to monitor the instantaneous conductance value over time to detect an insufficient vent flow condition. The controller may be configured to detect the insufficient vent flow condition as an anomalously low conductance value compared to recent baseline conductance values.

Some versions of the present technology may include a respiratory therapy system configured to provide respiratory therapy to a patient breathing in successive breathing cycles including an inspiration phase and an expiration phase. The system may include a pressure generator configured to supply a flow of pressurised air. The pressure generator may be configured to couple with a patient interface via an air circuit to deliver the pressurised air from the pressure generator to the patient. The system may include at least one sensor configured to provide one or more signals indicative of a pressure and flow of the pressurised air flow. The system may include a controller including a processor configured to repeatedly detect values of instantaneous pressure and values of instantaneous flow rate from the one or more signals from the at least one sensor. The system may include a controller including a processor configured to repeatedly calculate instantaneous impedance values based on the values of instantaneous pressure and values of instantaneous flow rate. The system may include a controller including a processor configured to monitor changes in the instantaneous impedance values over time to detect an occurrence of a respiratory event within the system.

In some versions, the respiratory event may be an obstruction. The obstruction may be detected when the instantaneous impedance exceeds a predetermined threshold. The obstruction may be detected when the instantaneous impedance remains substantially unchanged over time. The obstruction may occur in the air circuit, the patient interface, or the patient's airways.

In some versions, the respiratory event may be flow starvation during a volume target mode. The flow starvation may be detected as a function of a profile of instantaneous impedance values over an inspiratory portion of a breathing cycle. The flow starvation may be detected when instantaneous impedance values are lower at an early to mid-inspiration portion of the inspiration phase compared to an end portion of the inspiration phase. The flow starvation may be detected by comparison of instantaneous impedance values calculated from an inspiration phase of a breathing cycle with an impedance threshold. The flow starvation may be detected when the instantaneous impedance values calculated from the inspiration phase of the breathing cycle fall below the impedance threshold.

In some cases, upon detection of the respiratory event, the controller may be configured to provide a message to indicate the occurrence of the respiratory event.

Some versions of the present technology may include a respiratory therapy system configured to provide respiratory therapy to a patient breathing in successive breathing cycles including an inspiration phase and an expiration phase. The system may include a pressure generator configured to supply a flow of pressurised air. The pressure generator may be configured to couple with a patient interface via an air circuit to deliver the pressurised air from the pressure generator to the patient. The system may include at least one sensor configured to provide one or more signals indicative of a pressure and a flow rate of the pressurised air flow. The system may include a controller including a processor configured to repeatedly detect values of instantaneous pressure and instantaneous flow rate from the one or more signals from the at least one sensor. The system may include a controller including a processor configured to repeatedly calculate instantaneous impedance values based on the values of instantaneous pressure and values of instantaneous flow rate. The system may include a controller including a processor configured to monitor changes in the instantaneous impedance values over time to monitor the respiratory therapy.

In some versions, the controller determines a level of difference in instantaneous impedance values calculated from a beginning portion of the inspiration phase and instantaneous impedance values calculated from an end portion of the inspiration phase. The controller may be configured to adjust a rise time setting based on the level of difference. The controller may be configured to adjust a peak inspiratory flow setting based on the level of difference. The controller may be configured to monitor the instantaneous impedance value over time to determine a patient's inspiration phase and expiration phase of each breathing cycle. The controller may be configured to monitor the instantaneous impedance value over time to detect an insufficient vent flow condition. The controller may be configured to detect an insufficient vent flow condition as an anomalously high impedance value compared to recent baseline impedance values.

One form of the present technology comprises a method and apparatus that detects a patient circuit disconnection based on a determination of an instantaneous impedance in the respiratory circuit. The instantaneous impedance may be compared to an impedance threshold or an impedance profile (shape) consistent with a passive unconnected circuit. The impedance threshold may be determined based on the patient circuit coupled to the apparatus.

One form of the present technology comprises a method and apparatus that detects a patient circuit disconnection based on a determination of an instantaneous conductance in the respiratory circuit. The instantaneous conductance may be compared to a conductance threshold or a conductance profile (shape). The conductance threshold may be determined based on the patient circuit coupled to the apparatus.

Another aspect of one form of the present technology is a method of detecting an occurrence of a circuit disconnection event in a respiratory apparatus configured to provide respiratory therapy to a patient via a patient circuit, the method comprising determining a type of patient circuit configuration coupled to the respiratory apparatus; determining a disconnection setting as a function of the type of patient circuit configuration; in a controller of the respiratory apparatus repeatedly determine pressure and flow parameters and determine an instantaneous disconnection parameter based on the pressure and flow parameters; and determining the occurrence of a circuit disconnection event based on the instantaneous disconnection parameter as a function of the disconnection setting. In some forms the disconnection setting and the instantaneous disconnection parameter may be conductance values. In other forms the disconnection setting and the instantaneous disconnection parameter may be impedance values.

Another aspect of one form of the present technology is a method of detecting an occurrence of a circuit disconnection in a respiratory apparatus configured to provide respiratory therapy to a patient via a patient circuit, the method comprising: in a controller of the respiratory apparatus repeatedly determine pressure and flow parameters and repeatedly determine an instantaneous disconnection parameter based on the pressure and flow parameters; and compare successive instantaneous disconnection parameters to determine a level of variability in the instantaneous disconnection parameters over time and determine the occurrence of a circuit disconnection based on level of variability. The instantaneous disconnection parameter may be a conductance value or an impedance value.

Another aspect of one form of the present technology is a circuit disconnection system for detecting the occurrence of a circuit disconnection event in a respiratory apparatus, the system comprising: a controller having at least one processor to access data representing pressure and flow parameters of breathable gas, the controller configured to determine a type of patient circuit configuration coupled to the respiratory apparatus; determine a disconnection setting as a function of the type of patient circuit configuration; determine an instantaneous disconnection parameter based on the pressure and flow parameters; determine the occurrence of a circuit disconnection event based on the instantaneous disconnection parameter as a function of the disconnection setting; and indicate the occurrence of a circuit disconnection event. In some forms the disconnection setting and the instantaneous disconnection parameter may be conductance values. In other forms the disconnection setting and the instantaneous disconnection parameter may be impedance values.

In some forms the disconnection detection system or method may include the disconnection setting being a first disconnection threshold and the determined instantaneous disconnection parameter is compared to the first disconnection threshold to determine the occurrence of a circuit disconnection event.

In other forms of the disconnection detection system or method the disconnection setting is a profile shape and occurrence of a circuit disconnection event includes comparing a plurality of the determined instantaneous disconnection parameters to the profile shape to determine the occurrence of a circuit disconnection.

In some forms of the disconnection detection system or method patient specific information may be input into the respiratory apparatus and the patient specific information may be used in determining the disconnection setting. The patient specific information may include one or more of a patient's age, weight, height or patient type.

In some forms of the disconnection detection system or method the disconnection setting may be determined from a look-up table stored in a memory of the respiratory apparatus.

In some forms of the disconnection detection system or method the type of patient circuit configuration may be automatically detected by the respiratory apparatus. Whilst in other forms the type of patient circuit configuration may be entered into the respiratory apparatus via a user interface. The type of patient circuit configuration may be determined to be at least one of invasive, non-invasive, vented, non-vented, single limb or double limb.

In some forms of the disconnection detection system or method an indication of a circuit connection status is provided on a user interface of the respiratory apparatus. A disconnection indication may be provided when a circuit disconnection event is detected. The disconnection indication may include providing a message on the respiratory apparatus or activating a disconnection alarm or both. In some forms the disconnection alarm may be muted for a predetermined period of time via a user interface of the respiratory apparatus. In some forms the disconnection indication must be continuously provided for a predetermined time prior to the disconnection alarm being activated. The predetermined time may be a set time between 5 seconds and 60 seconds or a predetermined number of breaths. The predetermined time may be adjustable.

In some forms of the disconnection detection system or method the instantaneous disconnection parameter is determined at least once per breath. For example the instantaneous disconnection parameter is determined during an inspiration phase of each breath, or at least once during an inspiration phase of each breath and at least once during an expiration phase of each breath. In other forms the instantaneous disconnection parameter may be determined at predetermined time intervals.

In some forms of the disconnection detection system or method a sensitivity setting to adjust a sensitivity of the disconnection setting is determined. The sensitivity setting may be determined as a default sensitivity setting as a function of the type of patient circuit configuration. The sensitivity setting may be determined during a testing phase and the testing phase may occur prior to the respiratory apparatus providing respiratory therapy to the patient or whilst the respiratory apparatus is providing respiratory therapy to the patient. The activation of a disconnection alarm may be disabled during the testing phase.

In some forms the sensitivity setting may be selectable via a user interface from a predetermined range of settings. The predetermined range of settings may include values between 1% and 100%. Such as the predetermined range of settings may include values between 5% and 95% provided in 5% increments.

In some forms a sensitivity setting indication may be provided on a display of the respiratory apparatus, the sensitivity setting indication may provide an indication as whether the determined sensitivity setting has detected a disconnection event.

In some forms after detecting the occurrence of a circuit disconnection event, the disconnection detection system or method may monitor for respiratory indicators that indicate the patient is still connected to the patient circuit to qualify the disconnection event For example, if a respiratory indicator does indicate a patient is still connected to the patient circuit, the occurrence of the circuit disconnection event may be qualified as false such that it is disqualified as a circuit disconnection event. Alternatively, if a respiratory indicator does not indicate a patient is still connected to the patient circuit, the occurrence of the circuit disconnection event may be qualified as true such that it confirms the circuit disconnection event. The respiratory indicators may include one or more of: (i) detecting an expiratory flow indicative of expiration; (ii) detecting an inspiratory flow indicative of inspiration; (iii) a difference in the instantaneous disconnection parameter determined during an inspiration phase compared to the instantaneous parameter determined during an expiration phase; (iv) a comparison of the instantaneous disconnection parameter to a calculated variance of previous measures of the instantaneous disconnection parameters; or (v) a variation in the instantaneous disconnection parameter over time within a breath phase.

In some forms after detecting the occurrence of a circuit disconnection event the disconnection detection system or method may compare the determined flow parameter to a predetermined threshold to confirm the occurrence of the circuit disconnection event.

In some forms following the detection of the occurrence of a circuit disconnection event the disconnection detection system or method may detect re-connection of the patient circuit to the patient. The re-connection of the patient circuit to the patient may be detected by comparing the instantaneous disconnection parameter to a second threshold. The re-connection of the patient circuit to the patient may be detected by detection of an abrupt change in the instantaneous disconnection parameter.

Another aspect of one form of the present technology is a respiratory apparatus including a circuit disconnection system or a method of detecting a circuit disconnection event.

Another aspect of one form of the present technology is a respiratory system configured to provide respiratory therapy to a patient breathing in successive breathing cycles including an inspiration phase and an expiration phase, the system comprising a pressure generator configured to provide a supply of pressurised gas; at least one sensor to provide a signal indicative of a pressure and flow of the pressurised gas; a patient interface device coupled to an air delivery circuit to deliver the pressurised gas from the pressure generator to the patient; and a controller including a processor configured to repeatedly determine instantaneous pressure and flow values and determine an instantaneous conductance value based on the instantaneous pressure and flow values, wherein the controller monitors changes in the instantaneous conductance value over time to determine an occurrence of a respiratory event within the system.

In some forms the respiratory event is an obstruction event. The obstruction event may be detected when the instantaneous conductance falls below a predetermined threshold. In some forms the obstruction event is detected when the instantaneous conductance remains unchanged over time. The obstruction event may be in a patient circuit or a patient's airways.

In other forms the respiratory event is a flow starvation event occurring during a volume target mode. The flow starvation event may be detected as a function of a profile of the instantaneous conductance values over the inspiration phase of the breathing cycle. The flow starvation event may be detected when instantaneous conductance values are higher at an early to mid-inspiration phase compared to an end of the inspiration phase. The flow starvation event may be detected by comparison of the instantaneous conductance values determined during an inspiration phase of the breathing cycle with a third conductance threshold. The flow starvation event may be detected when the instantaneous conductance values determined during an inspiration phase of the breathing cycle exceed the third conductance threshold.

In some forms the controller of the respiratory system may be configured to provide a message to indicate the occurrence of the respiratory event.

Another aspect of one form of the present technology is a respiratory system configured to provide respiratory therapy to a patient breathing in successive breathing cycles including an inspiration phase and an expiration phase, the system comprising: pressure generator configured to provide a supply of pressurised gas; at least one sensor to provide a signal indicative of a pressure and flow of the pressurised gas; a patient interface device coupled to an air delivery circuit to deliver the pressurised gas from the pressure generator to the patient; and a controller including a processor configured to repeatedly determine instantaneous pressure and flow values and determine an instantaneous conductance value based on the instantaneous pressure and flow values, wherein the controller monitors changes in the instantaneous conductance value over time to monitor therapy.

The controller may determine a level of difference in the instantaneous conductance values determined at a beginning of the inspiration phase and the instantaneous conductance values determined at an end of the inspiration phase. The controller may be configured to adjust a rise time setting or a peak inspiratory flow setting based on the level of difference.

In some forms the controller may monitor the instantaneous conductance value over time to determine a patient's inspiration phase and expiration phase of each breathing cycle.

Another aspect of one form of the present technology is a respiratory system configured to provide respiratory therapy to a patient breathing in successive breathing cycles including an inspiration phase and an expiration phase, the system comprising: pressure generator configured to provide a supply of pressurised gas; at least one sensor to provide a signal indicative of a pressure and flow of the pressurised gas; a patient interface device coupled to an air delivery circuit to deliver the pressurised gas from the pressure generator to the patient; and a controller including a processor configured to repeatedly determine instantaneous pressure and flow values and determine an instantaneous impedance value based on the instantaneous pressure and flow values, wherein the controller monitors changes in the instantaneous impedance value over time to determine an occurrence of a respiratory event within the system.

In some forms the respiratory event is an obstruction event. The obstruction event may be detected when the instantaneous impedance exceeds a predetermined threshold. The obstruction event may be detected when the instantaneous impedance remains substantially unchanged over time. The obstruction event may be in a patient circuit or a patient's airways.

In some forms the respiratory event is a flow starvation event occurring during a volume target mode. The flow starvation event may be detected as a function of a profile of the instantaneous impedance values over an inspiration phase of the breathing cycle. The flow starvation event may be detected when instantaneous impedance values are lower at an early to mid-inspiration phase compared to an end of the inspiration phase. The flow starvation event may be detected by comparison of the instantaneous impedance values determined during an inspiration phase of the breathing cycle with a third impedance threshold. The flow starvation event may be detected when the instantaneous impedance values determined during an inspiration phase of the breathing cycle fall below the third impedance threshold. In some forms the controller is configured to provide a message to indicate the occurrence of the respiratory event.

Another aspect of one form of the present technology is a respiratory system configured to provide respiratory therapy to a patient breathing in successive breathing cycles including an inspiration phase and an expiration phase, the system comprising: pressure generator configured to provide a supply of pressurised gas; at least one sensor to provide a signal indicative of a pressure and flow of the pressurised gas; a patient interface device coupled to an air delivery circuit to deliver the pressurised gas from the pressure generator to the patient; and a controller including a processor configured to repeatedly determine instantaneous pressure and flow values and determine an instantaneous impedance value based on the instantaneous pressure and flow values, wherein the controller monitors changes in the instantaneous impedance value over time to monitor therapy.

In some forms the controller may determine a level of difference in the instantaneous impedance values determined at a beginning of the inspiration phase and the instantaneous impedance values determined at an end of the inspiration phase. The controller may be configured to adjust a rise time setting or a peak inspiratory flow setting based on the level of difference. The controller may monitor the instantaneous impedance value over time to determine a patient's inspiration phase and expiration phase of each breathing cycle.

An aspect of one form of the present technology is a method of detecting re-connection of a patient circuit to a respiratory apparatus.

Of course, portions of the aspects may form sub-aspects of the present technology. Also, various ones of the sub-aspects and/or aspects may be combined in various manners and also constitute additional aspects or sub-aspects of the present technology.

The methods, systems, devices and apparatus described herein for circuit disconnection detection can provide improved functioning in a processor, such as of a processor of a specific purpose computer, and/or monitoring devices for a respiratory apparatus. Moreover, in some cases they may be integrated within a controller or processor of a treatment device such as a respiratory pressure therapy device. Furthermore, the described methods, systems, devices and apparatus can provide improvements in the technological field of automated monitoring and/or respiratory apparatus for respiratory systems or conditions, including, for example, sleep disordered breathing, paediatric respiratory therapy or respiratory insufficiency (e.g., COPD) by permitting a device to perform circuit disconnection detection so that potentially problematic or dangerous respiratory related disconnection events may be discovered more readily.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

3.2 Respiratory System and Facial Anatomy

Figure 2A:
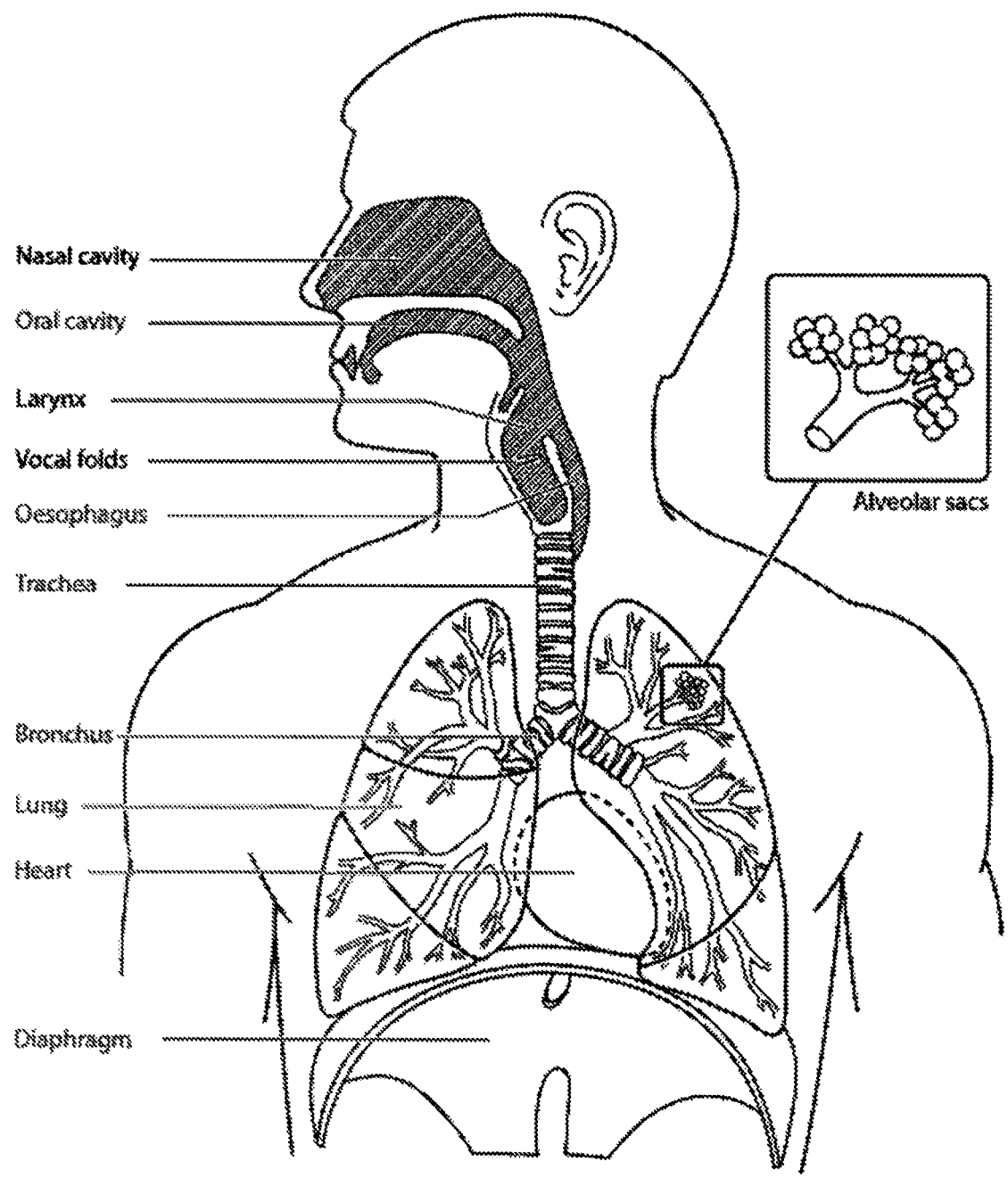

FIG. 2A shows an overview of a human respiratory system including the nasal and oral cavities, the larynx, vocal folds, oesophagus, trachea, bronchus, lung, alveolar sacs, heart and diaphragm.

Figure 2B:
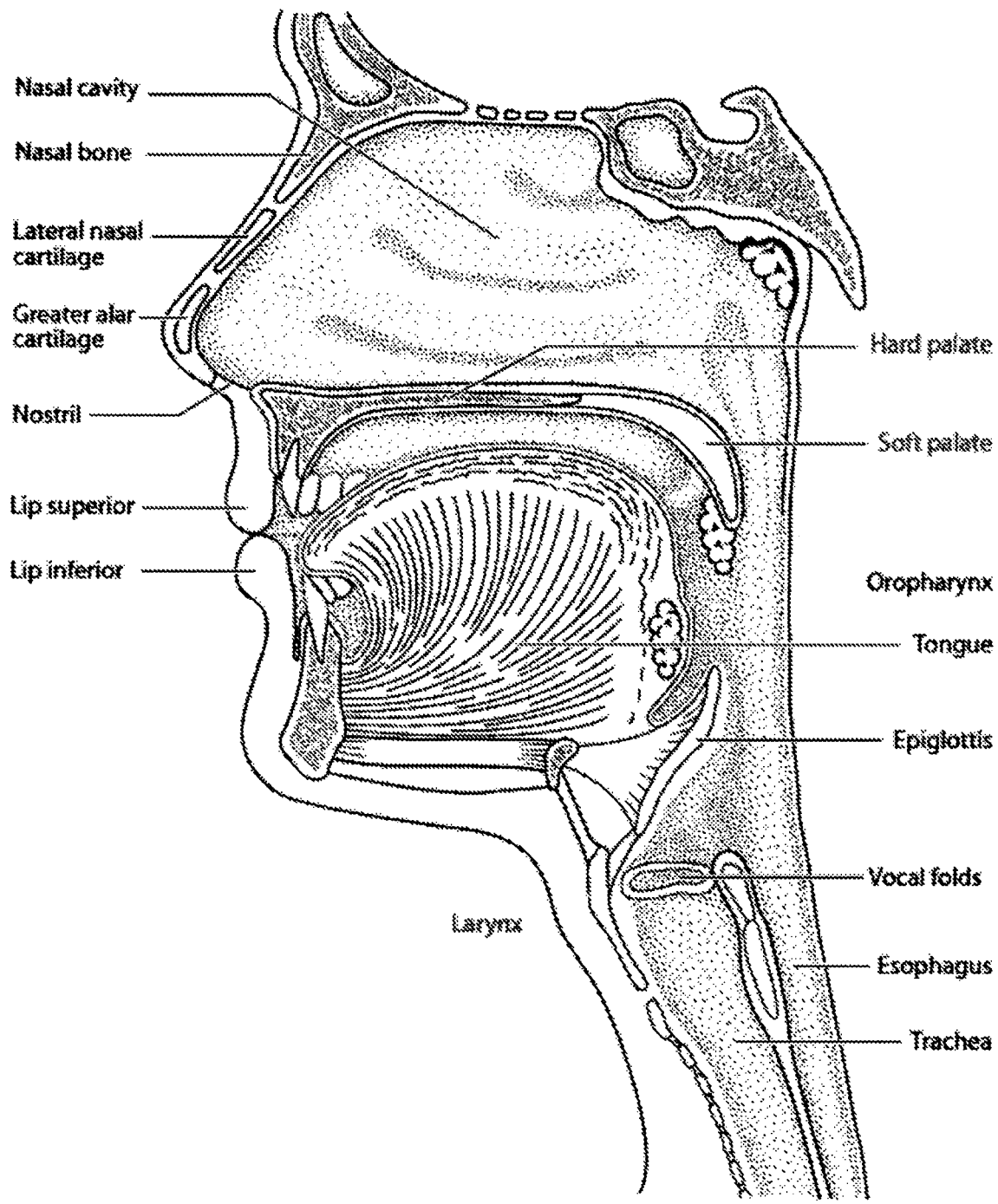

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

3.3 Patient Interface

Figure 3A:
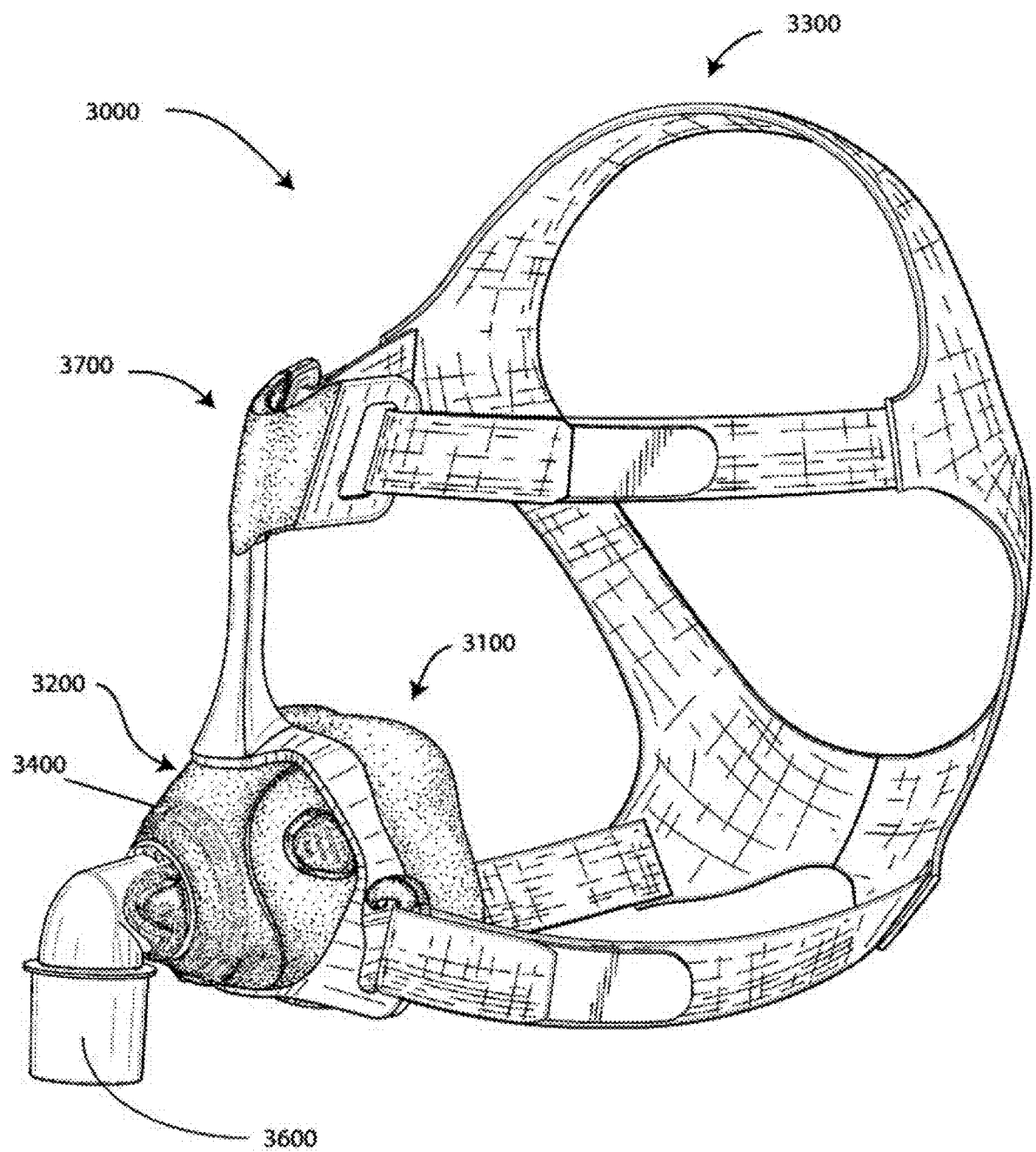

FIG. 3A shows a patient interface in the form of a nasal mask in accordance with one form of the present technology.

3.4 RPT Device

Figure 4A:
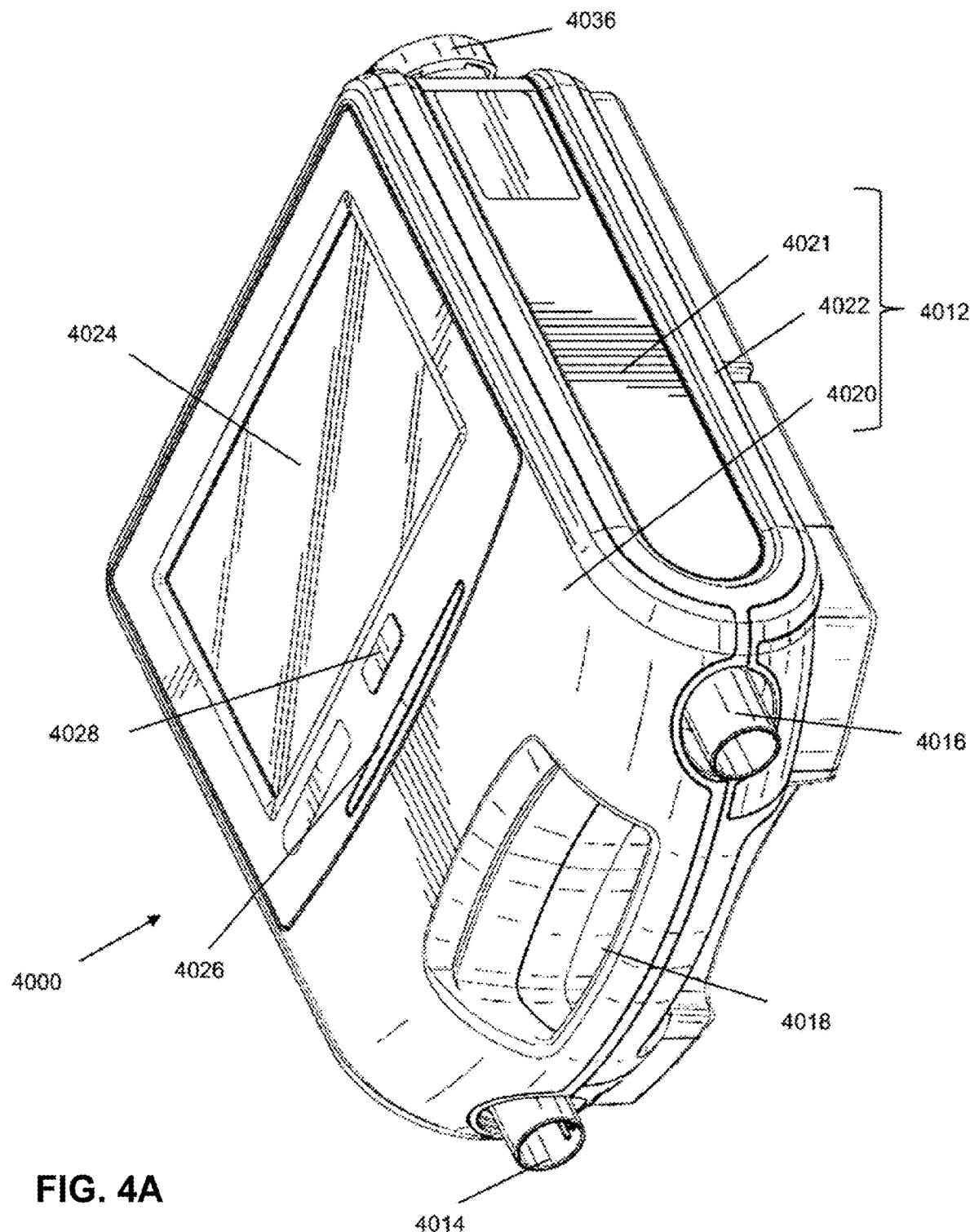

FIG. 4A shows a perspective view of an RPT device in the form of a ventilator device in accordance with one form of the present technology.

Figure 4B:
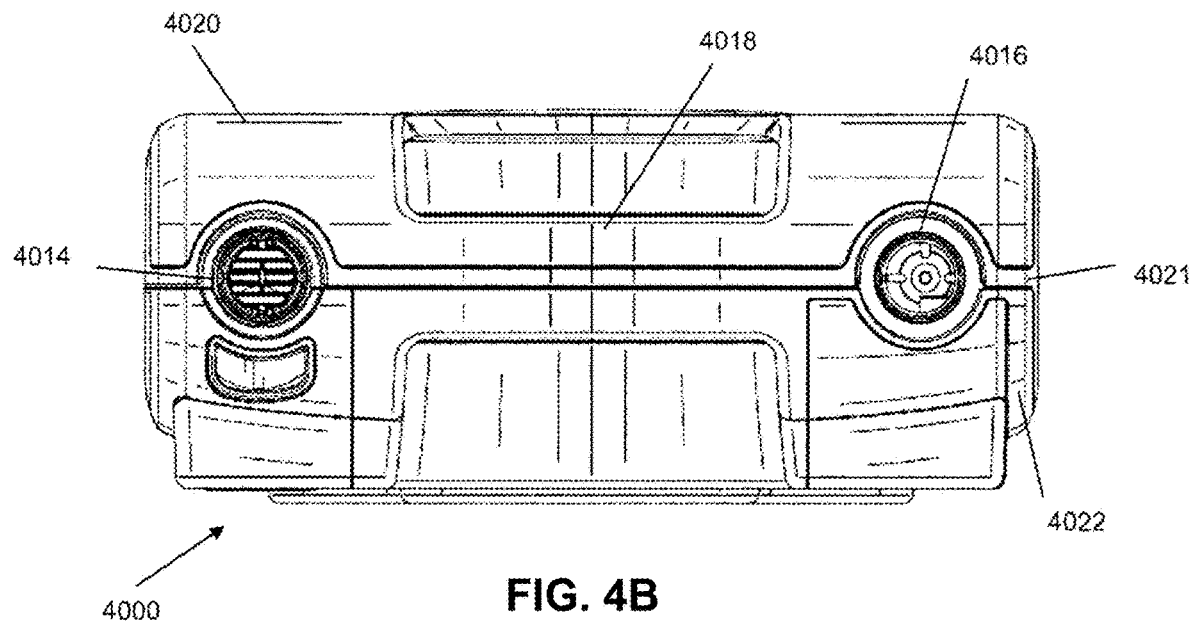

FIG. 4B shows a front view of the ventilator device of FIG. 4A.

Figure 4C:
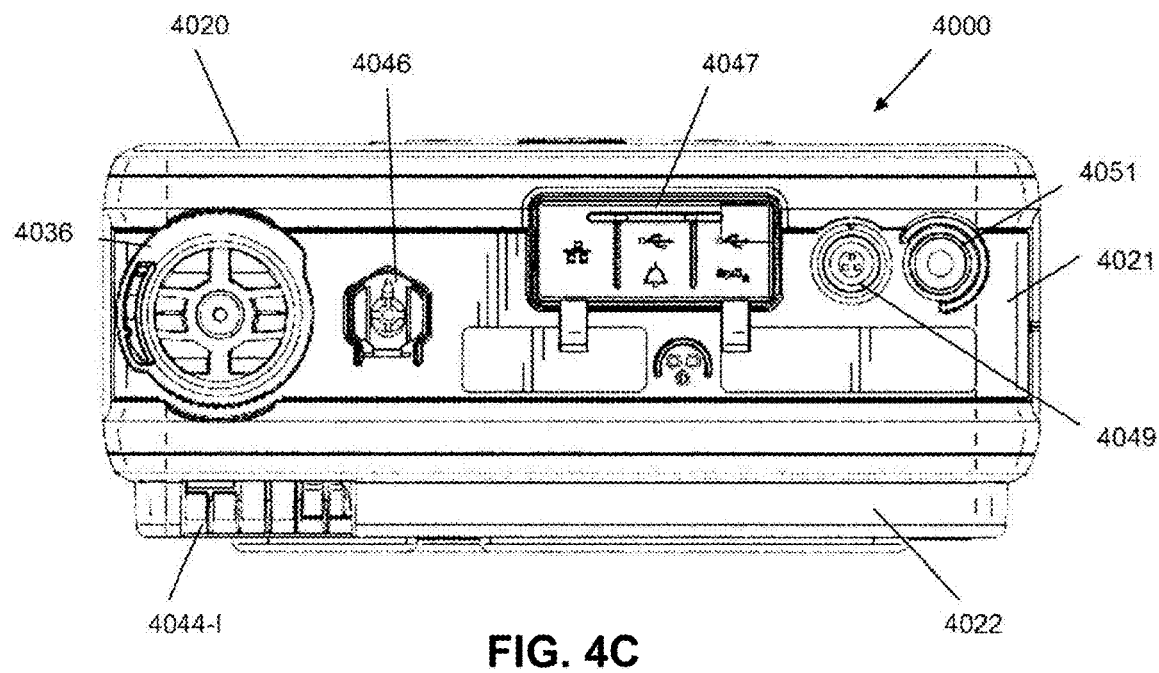

FIG. 4C shows a rear view of the ventilator device of FIG. 4A.

Figure 4D:
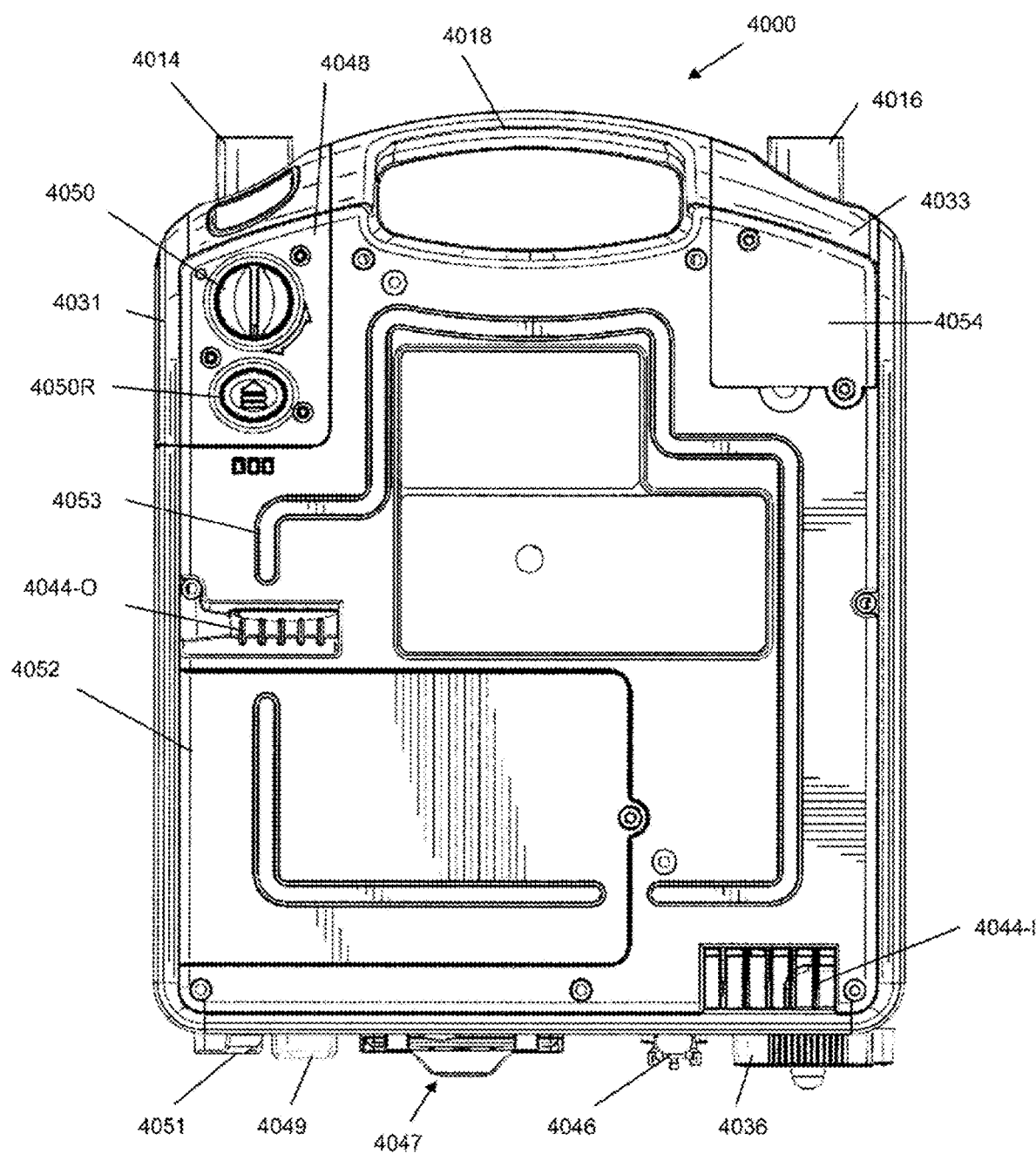

FIG. 4D shows a bottom view of the ventilator device of FIG. 4A.

Figure 4E:
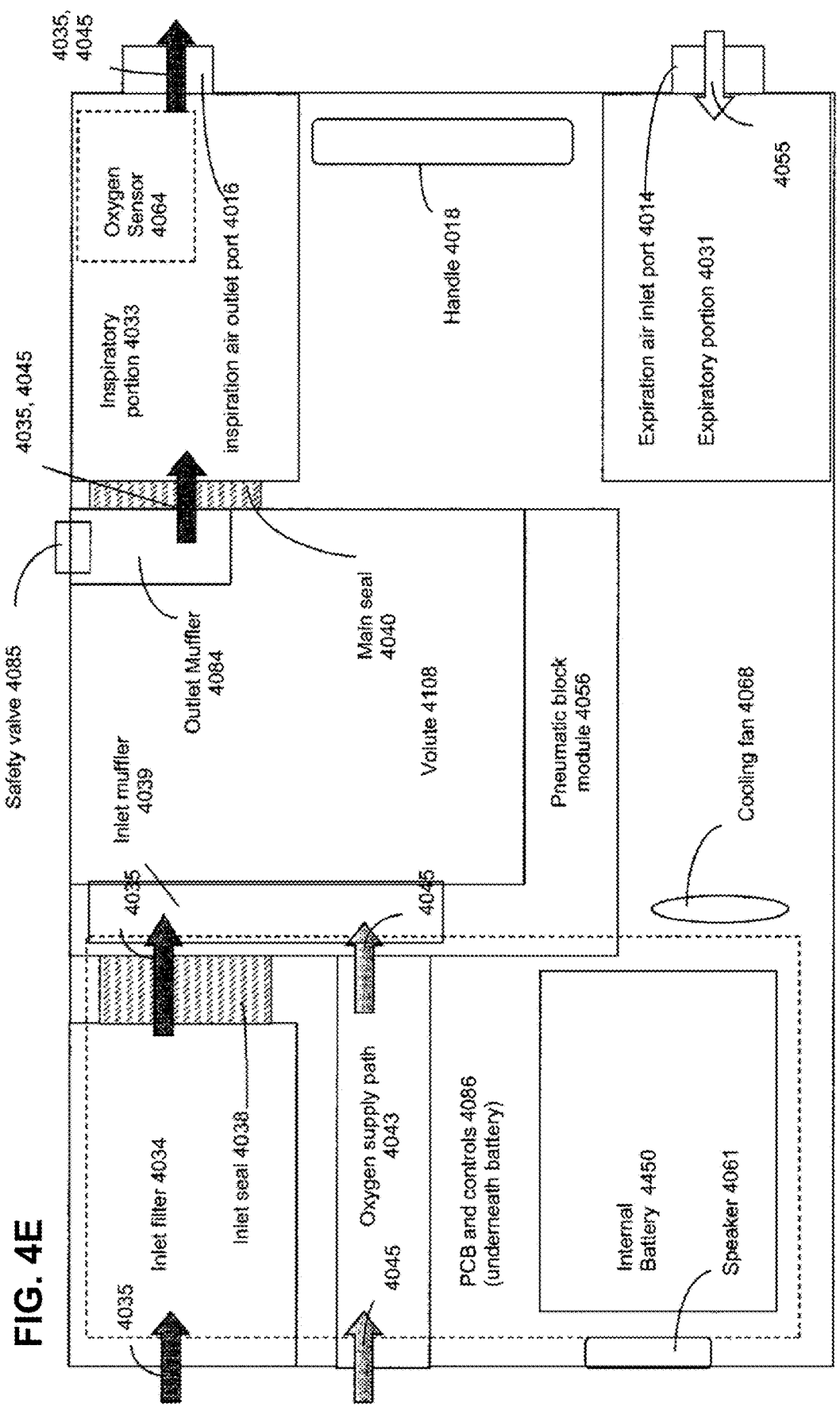

FIG. 4E shows a schematic of the arrangement of internal components in a ventilator according to an aspect of the present technology.

Figure 4F:
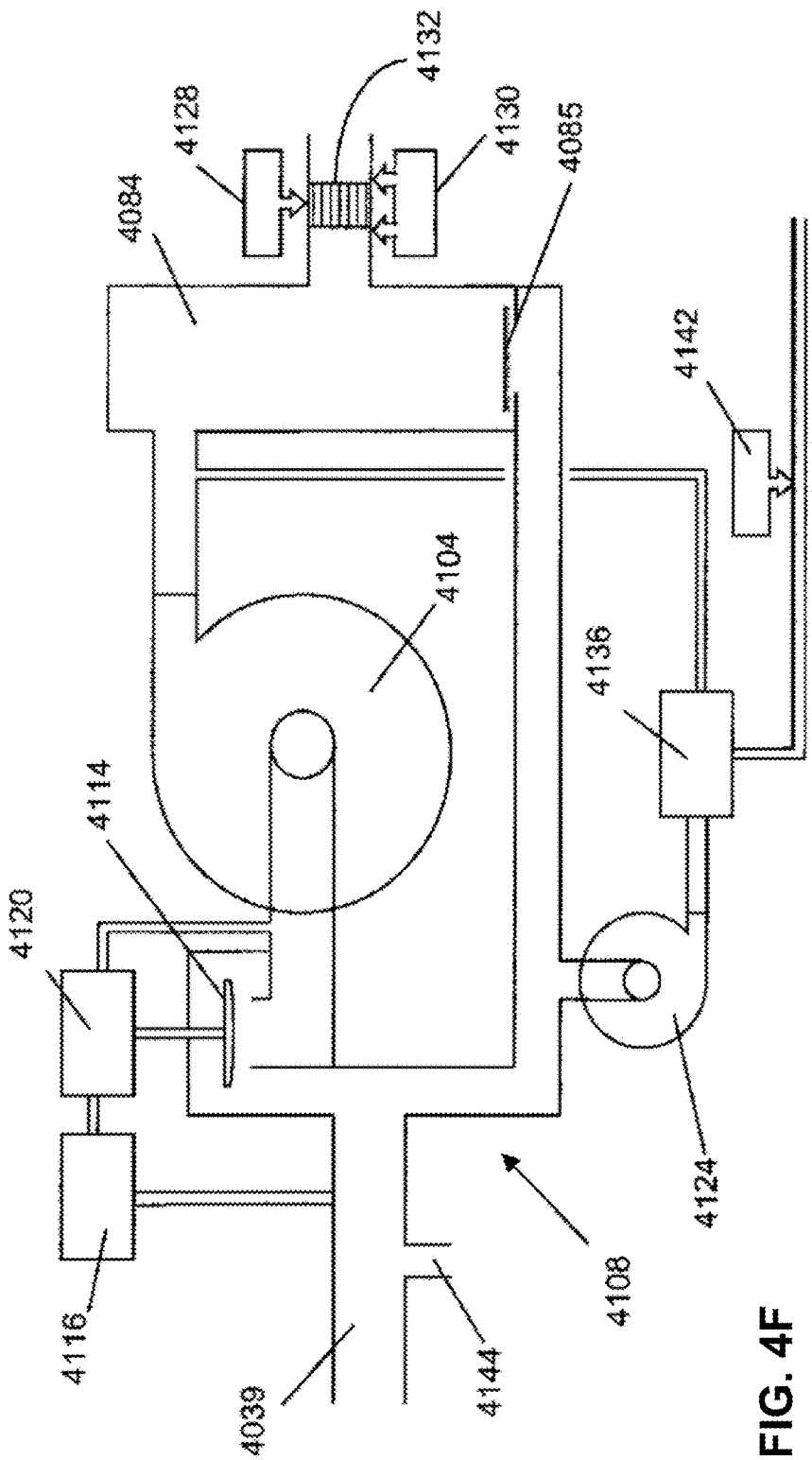

FIG. 4F shows a schematic view of the internals of the pneumatic block according to an aspect of the present technology.

Figure 4G:
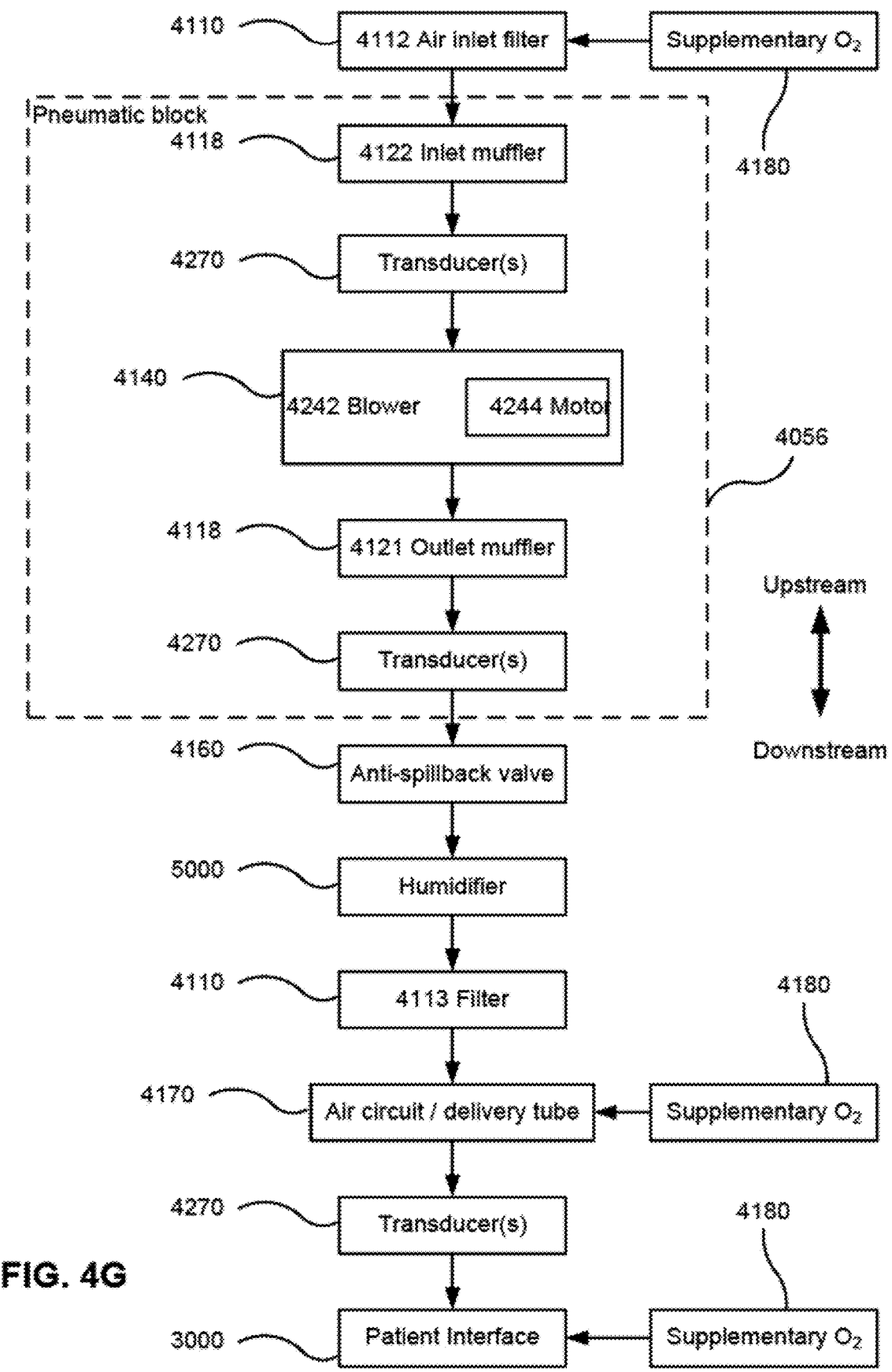

FIG. 4G shows a schematic diagram of the pneumatic circuit of a device in accordance with one form of the present technology. The directions of upstream and downstream are indicated.

Figure 4H:
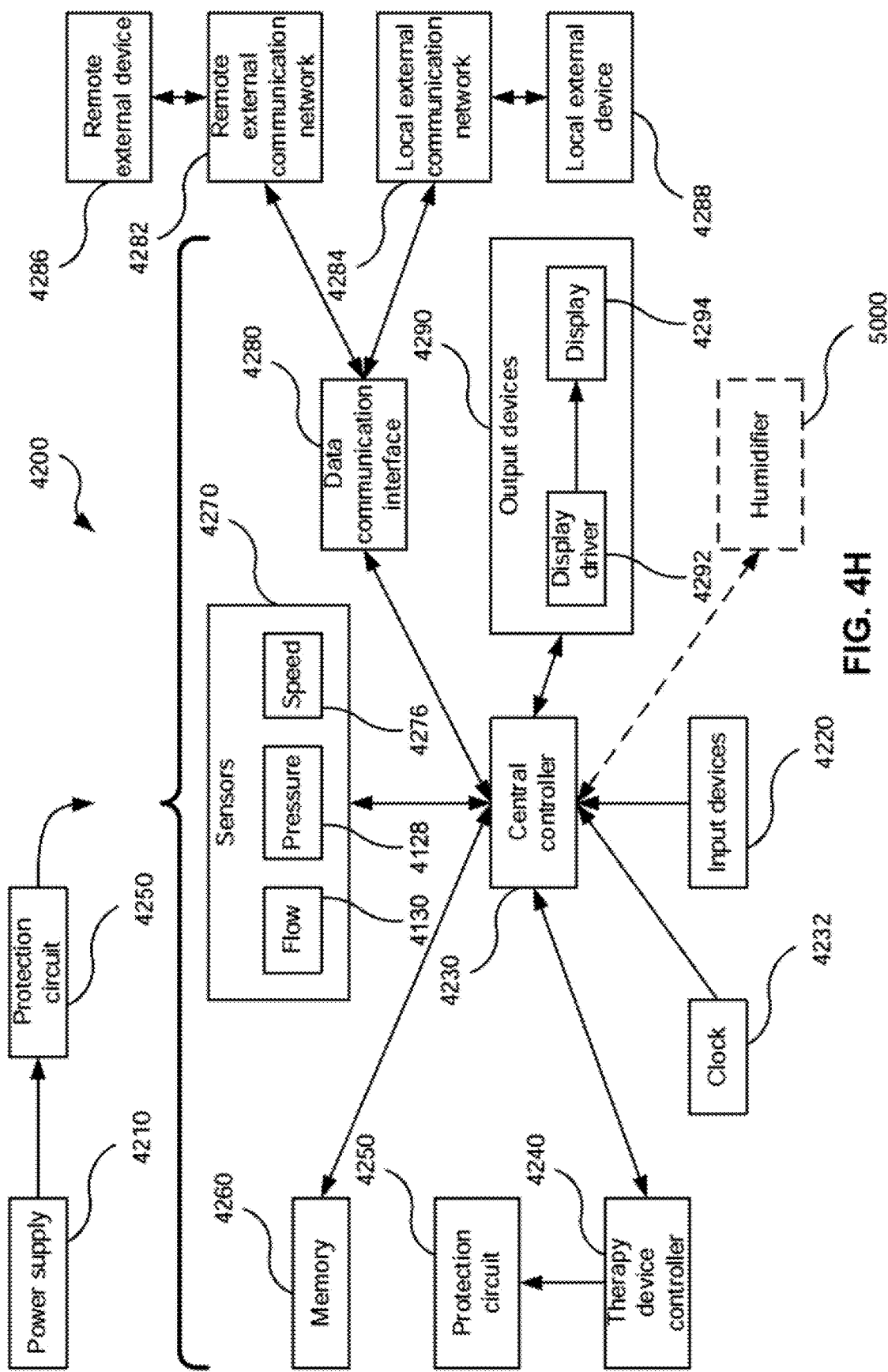

FIG. 4H shows a schematic diagram of the electrical components of a device in accordance with one aspect of the present technology.

Figure 4I:
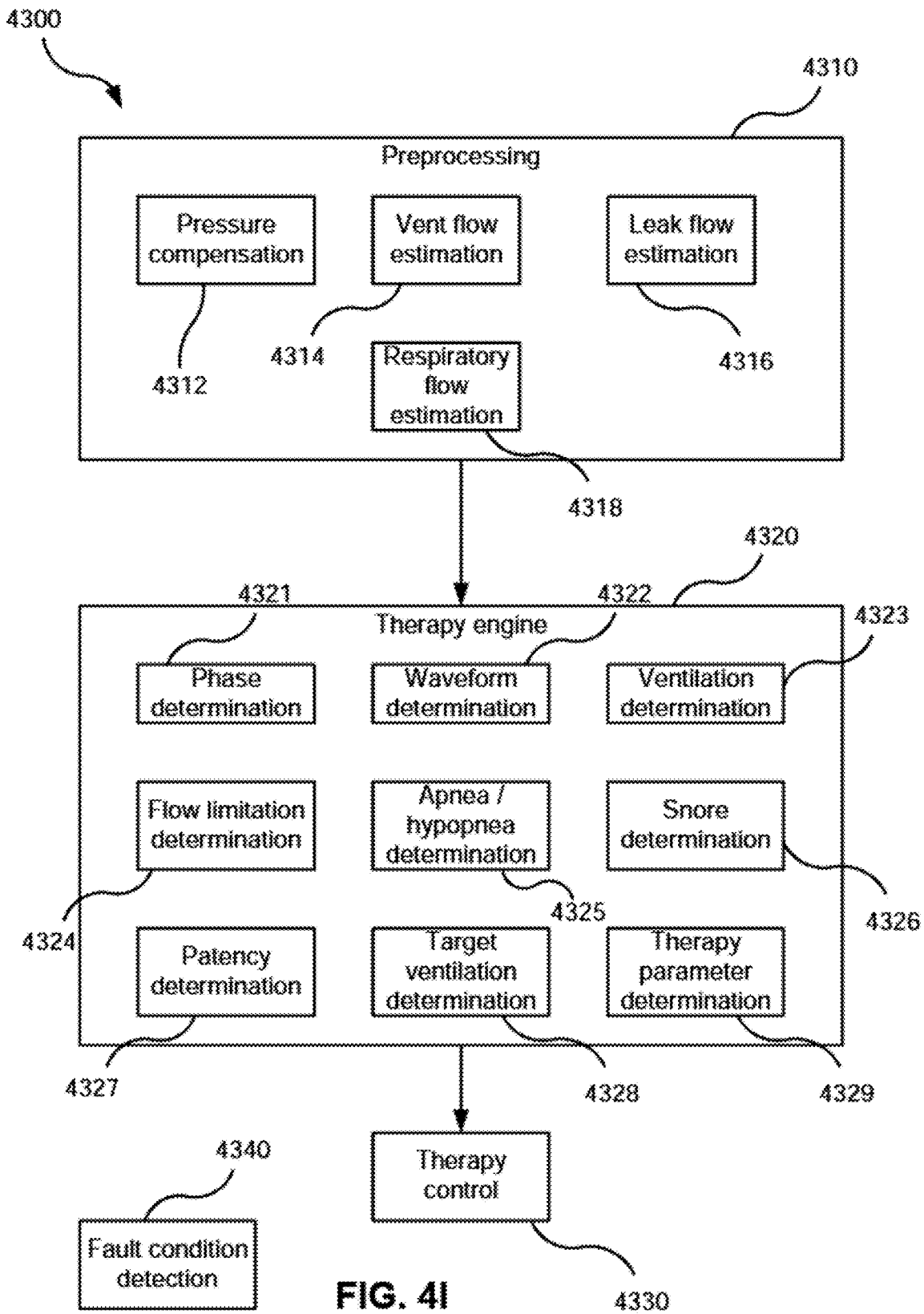

FIG. 4I shows a schematic diagram of the algorithms implemented in a device in accordance with an aspect of the present technology. In this figure, arrows with solid lines indicate an actual flow of information, for example via an electronic signal.

3.5 Humidifier

Figure 5A:
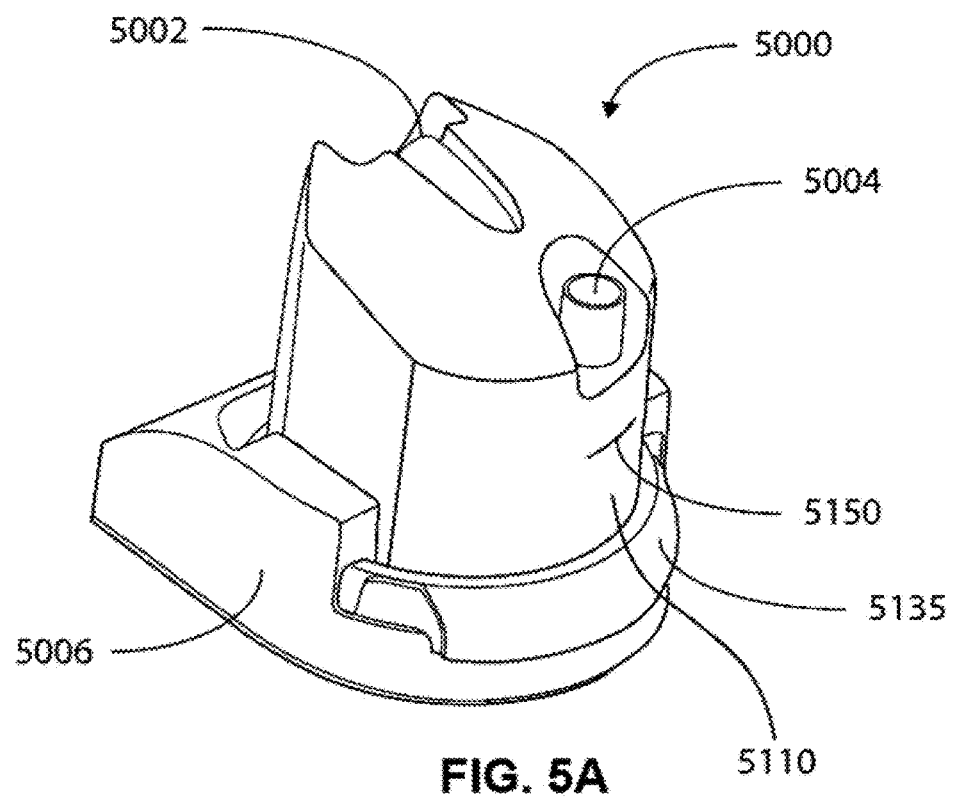

FIG. 5A shows an isometric view of a humidifier in accordance with one form of the present technology.

Figure 5B:
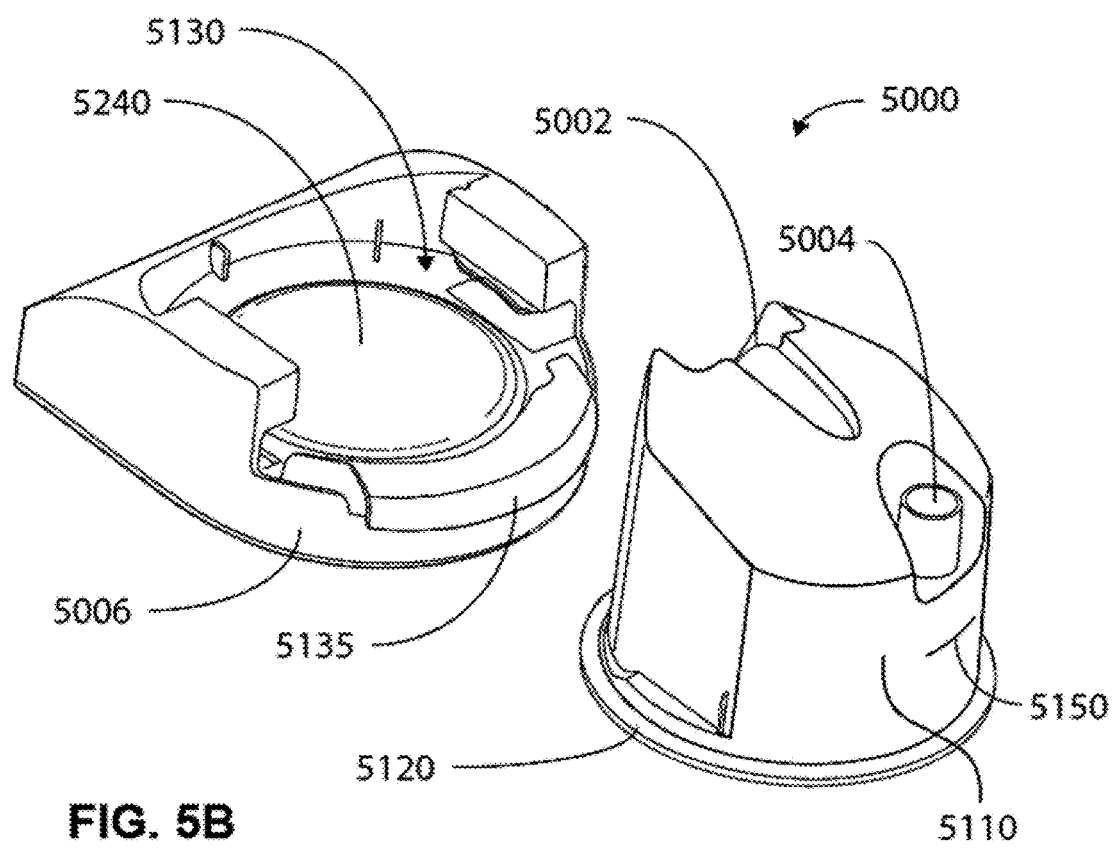

FIG. 5B shows an isometric view of a humidifier in accordance with one form of the present technology, showing a humidifier reservoir 5110 removed from the humidifier reservoir dock 5130.

Figure 5C:
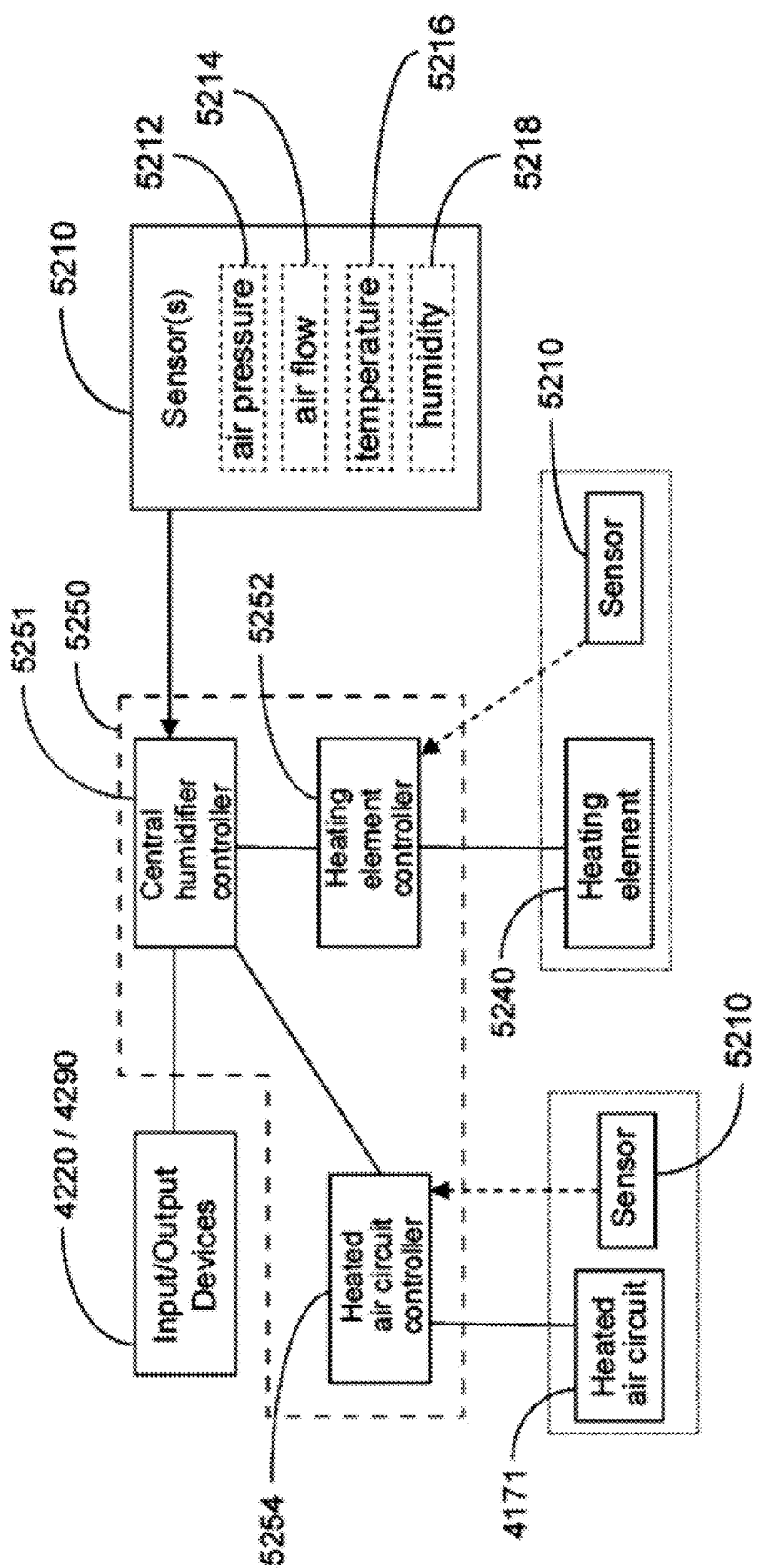

FIG. 5C shows a schematic of a humidifier in accordance with one form of the present technology.

3.6 Breathing Waveforms

Figure 6A:
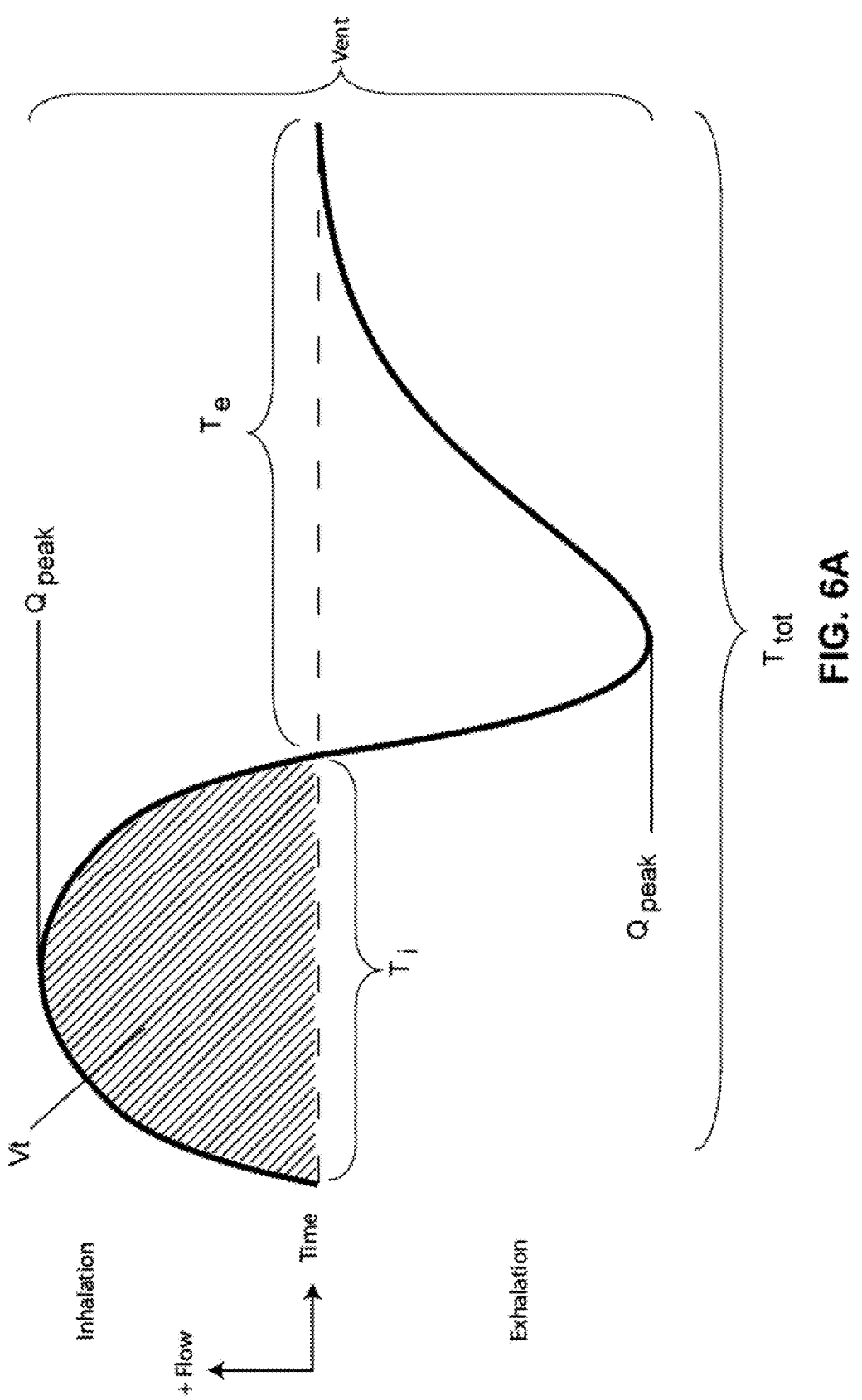

FIG. 6A shows a model typical breath waveform of a person while sleeping.

Figure 6B:
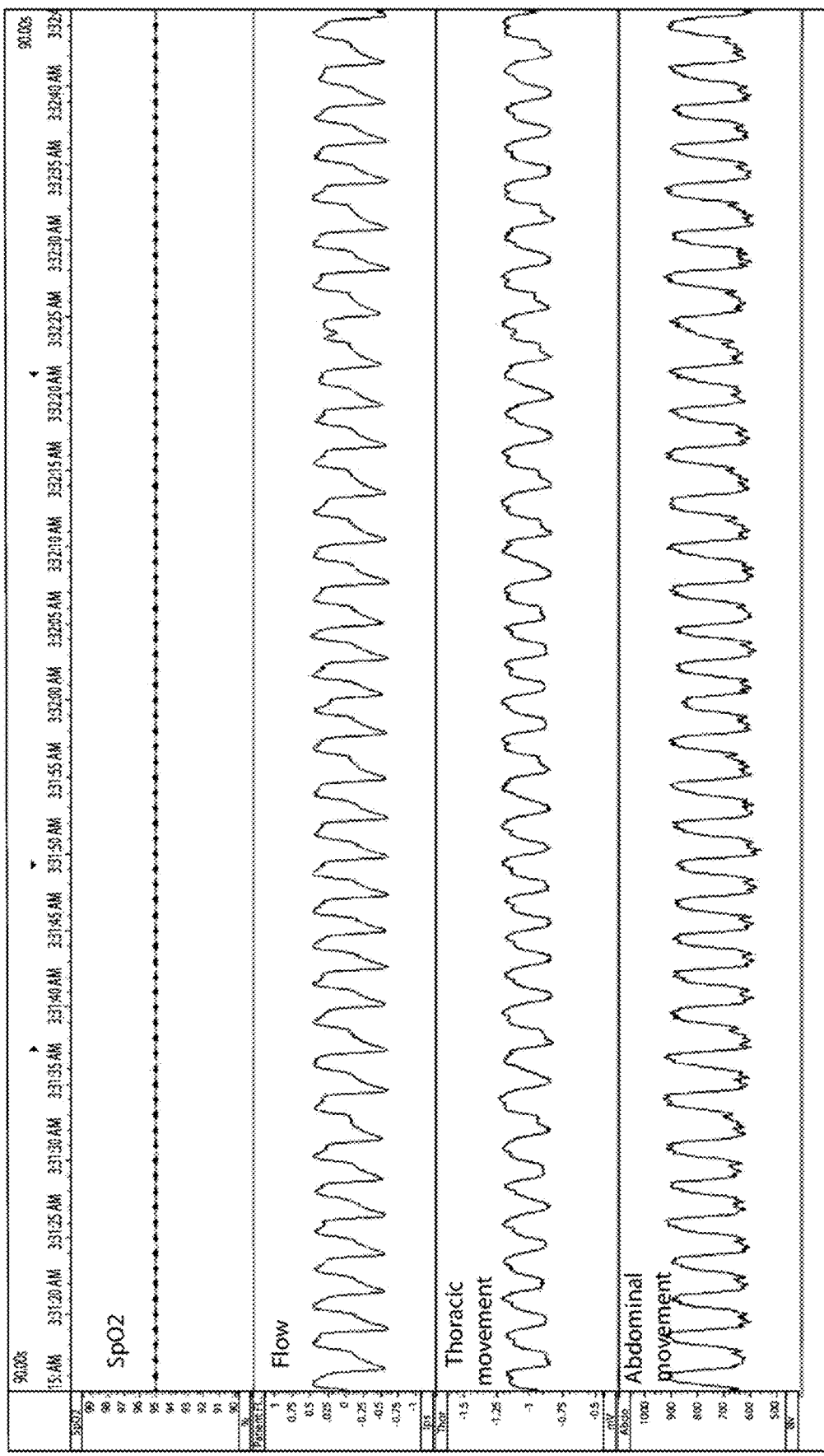

FIG. 6B shows a patient during Non-REM sleep breathing normally over a dperiod of about ninety seconds.

3.7 Fault Detection

Figure 7A:
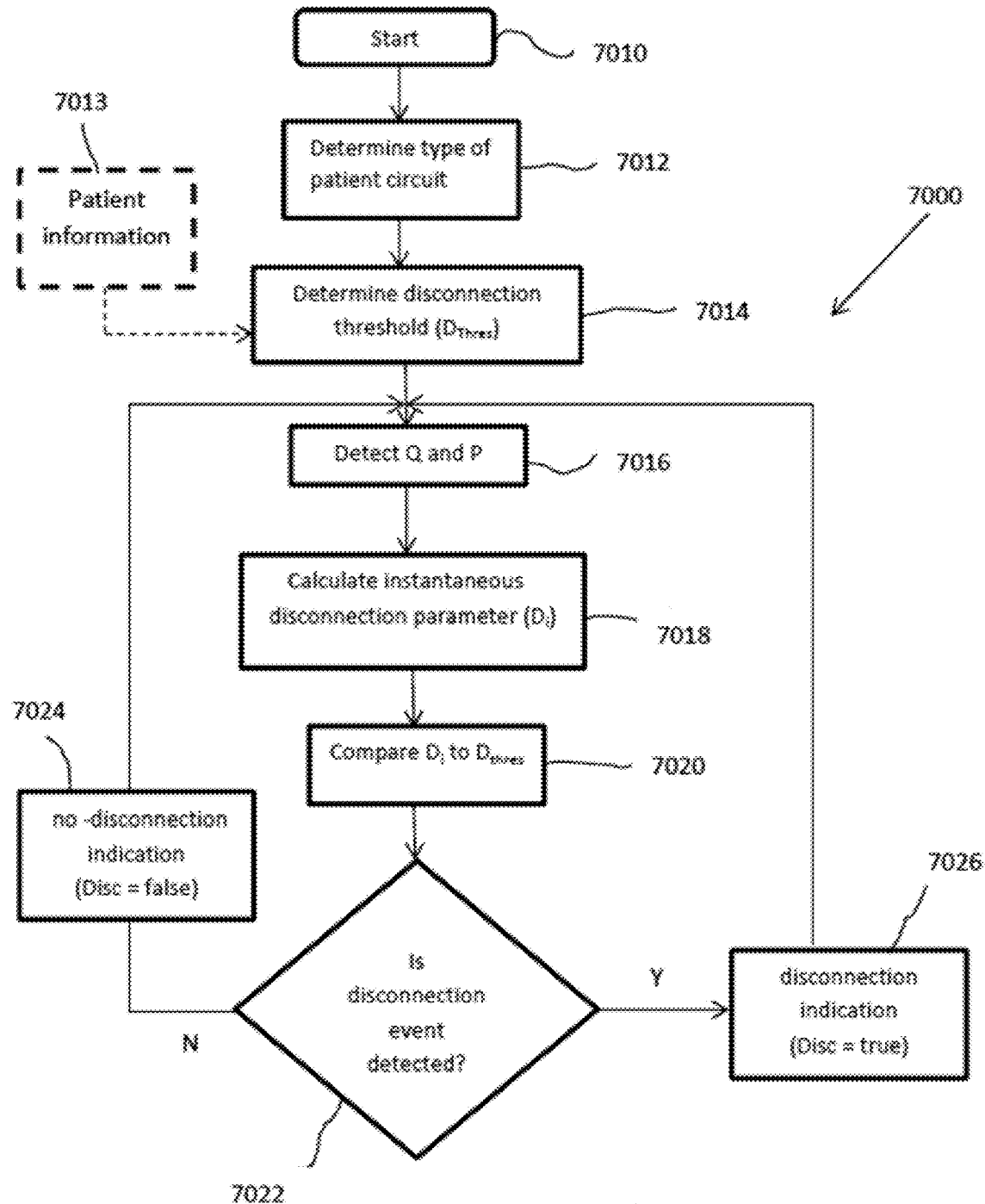

FIG. 7A is a flow chart of a circuit disconnection detection method according to an aspect of the present technology.

Figure 7B:
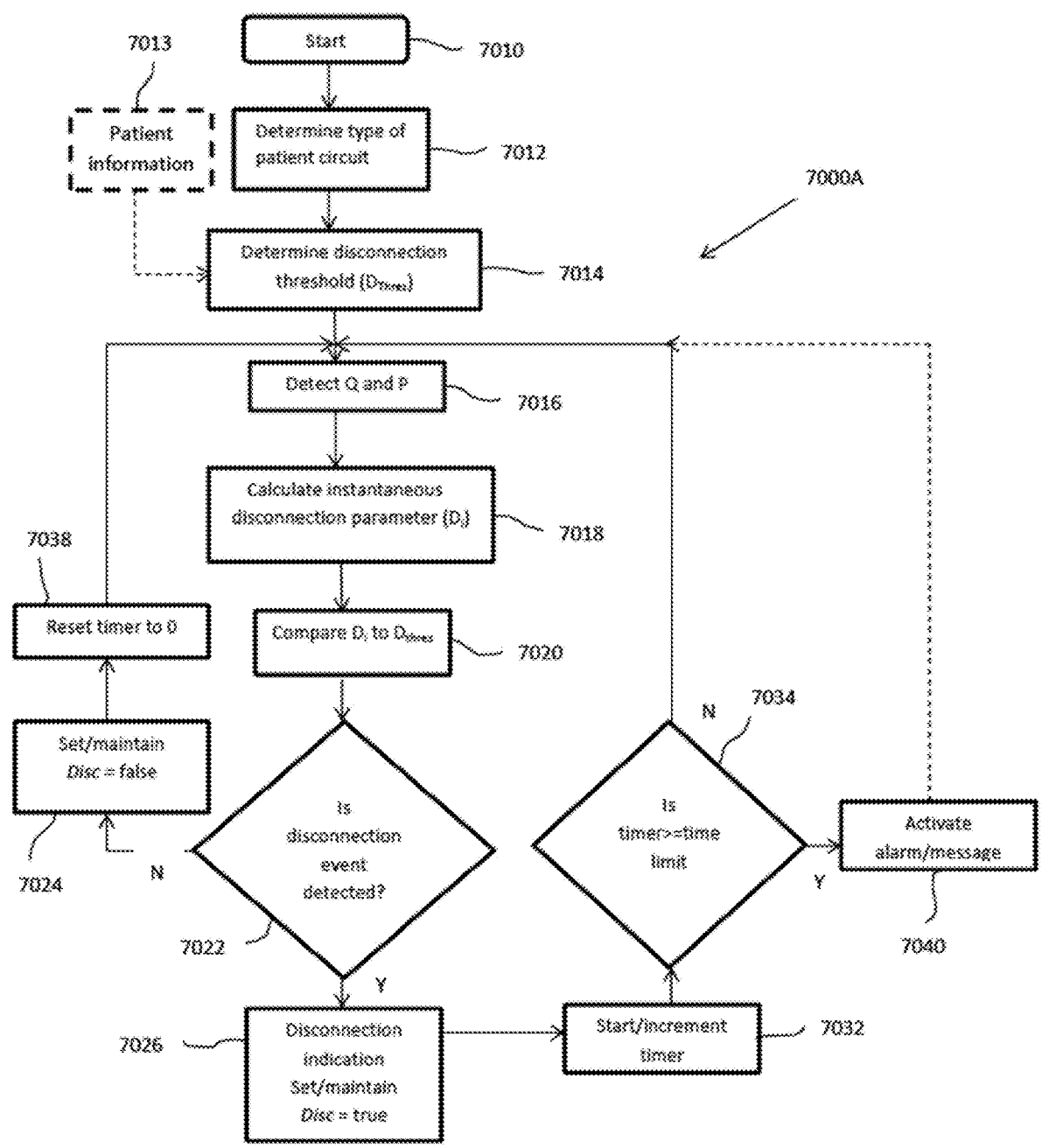

FIG. 7B is a flow chart of a circuit disconnection detection method according to another aspect of the present technology.

Figure 7C:
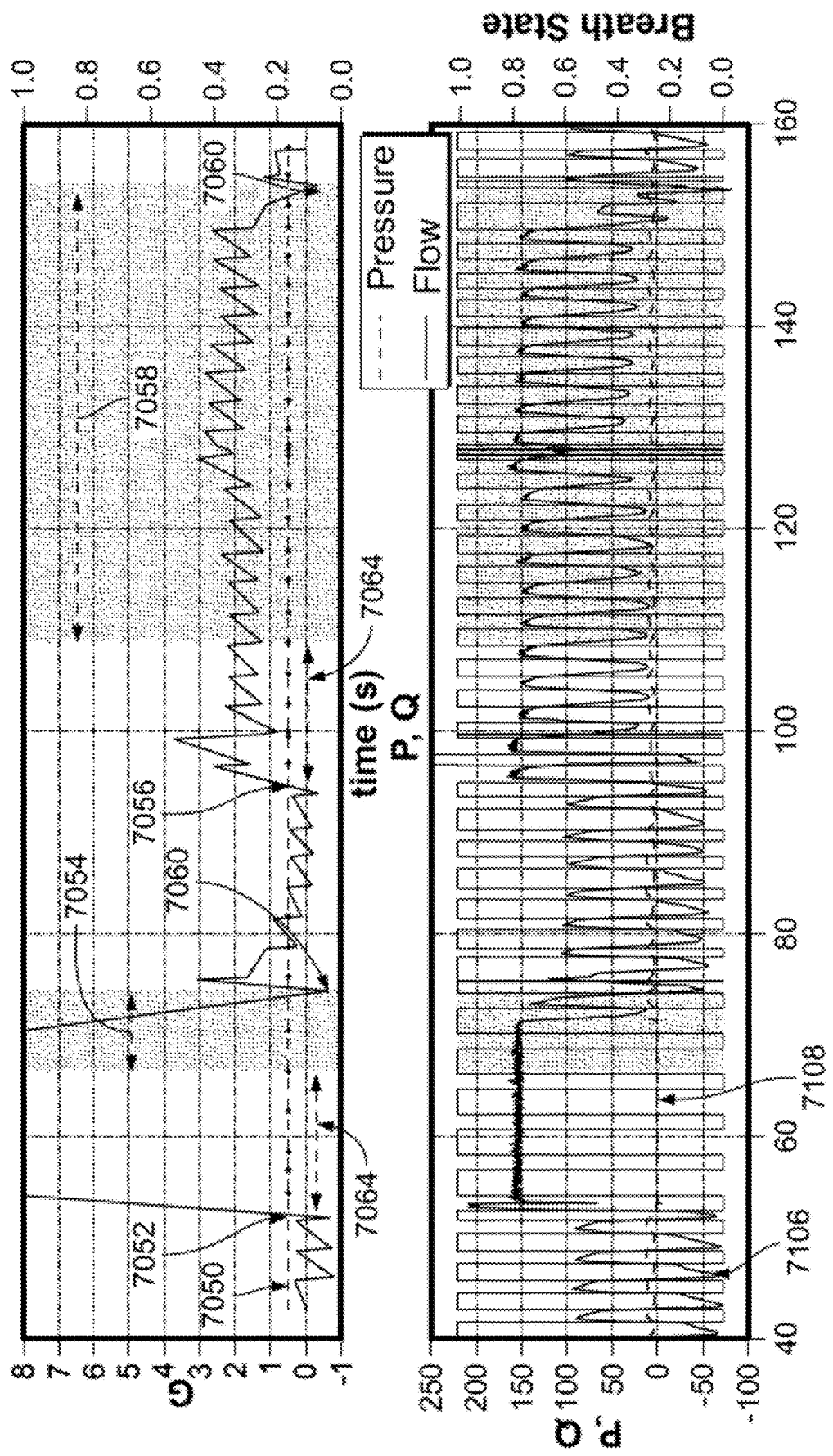

FIG. 7C shows traces for instantaneous conductance, pressure and flow values over time for a conductance threshold with a sensitivity setting of 45%.

Figure 7D:
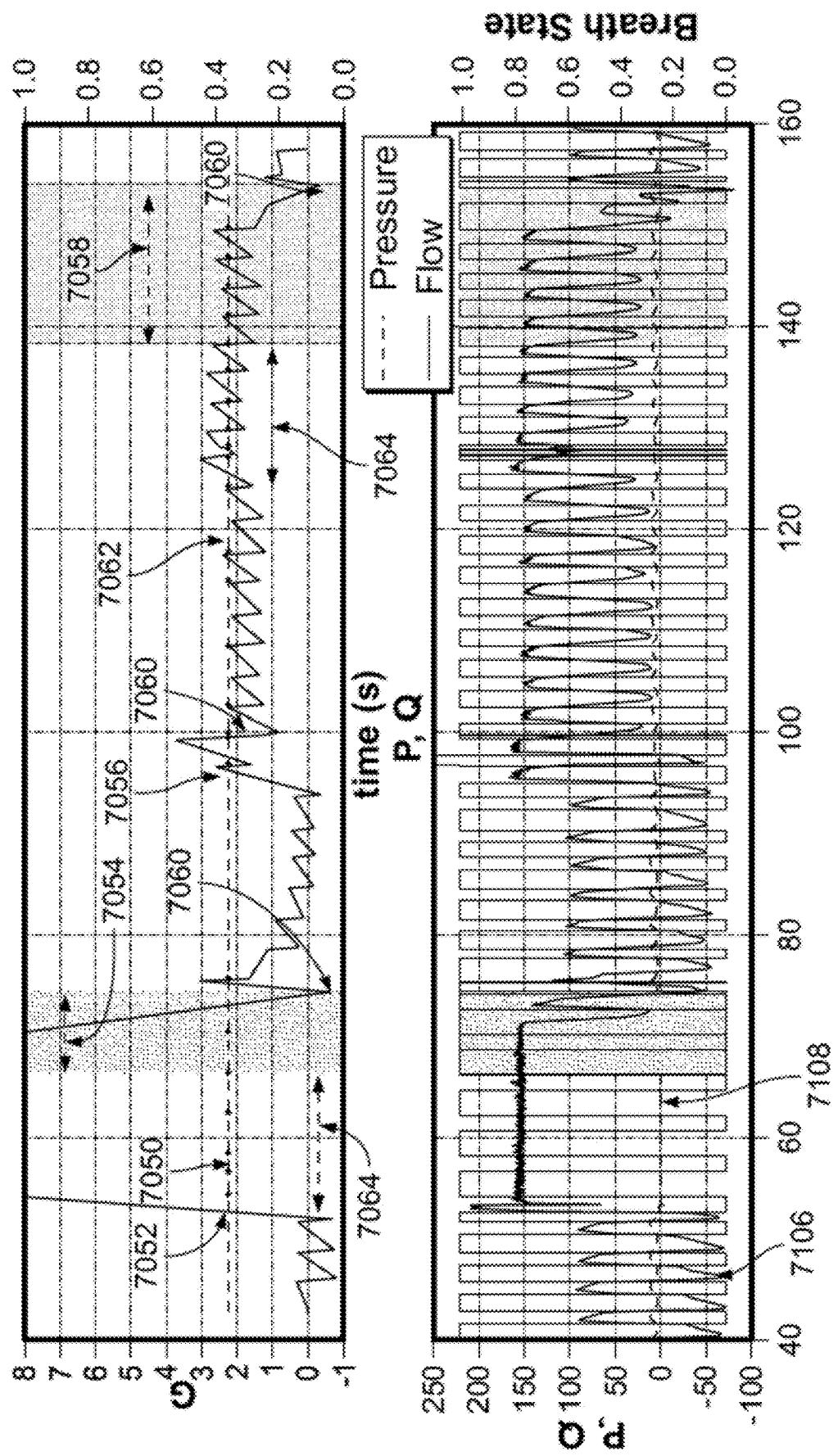

FIG. 7D shows traces for instantaneous conductance, pressure and flow values over time for a conductance threshold with a sensitivity setting of 20%.

Figure 7E:
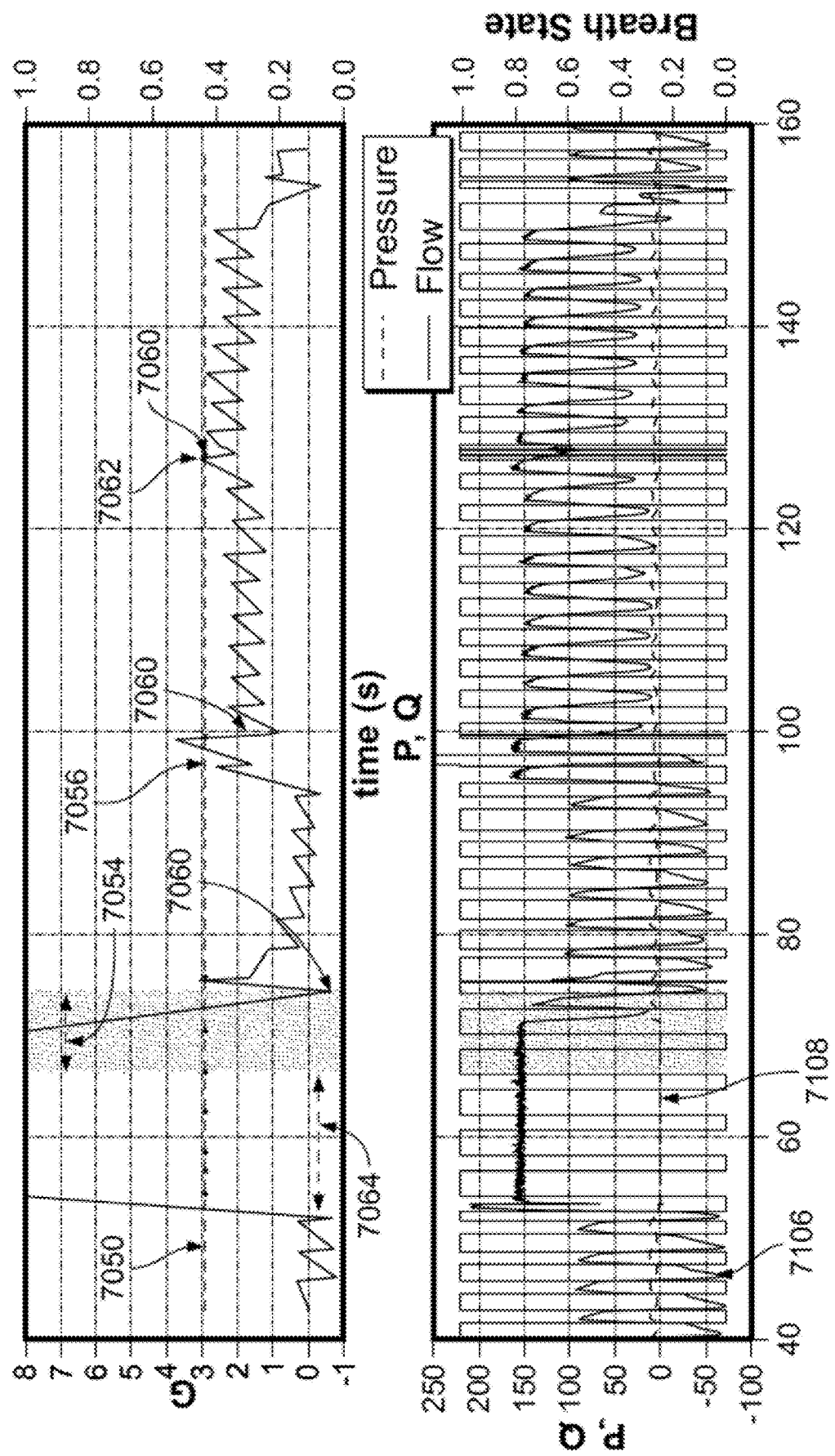

FIG. 7E shows traces for instantaneous conductance, pressure and flow values over time for a conductance threshold with a sensitivity setting of 15%.

Figure 7F:
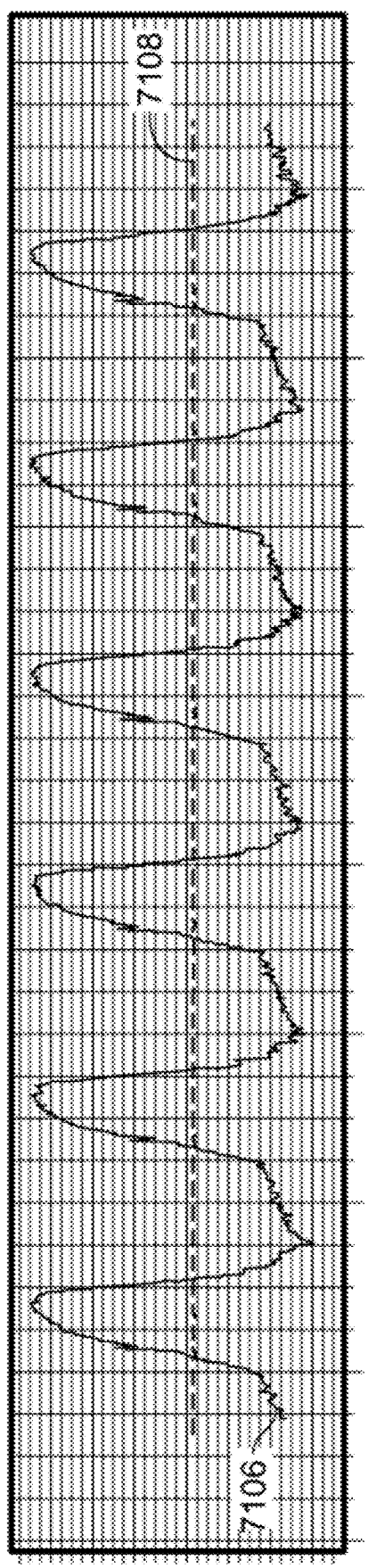
Figure 7F:
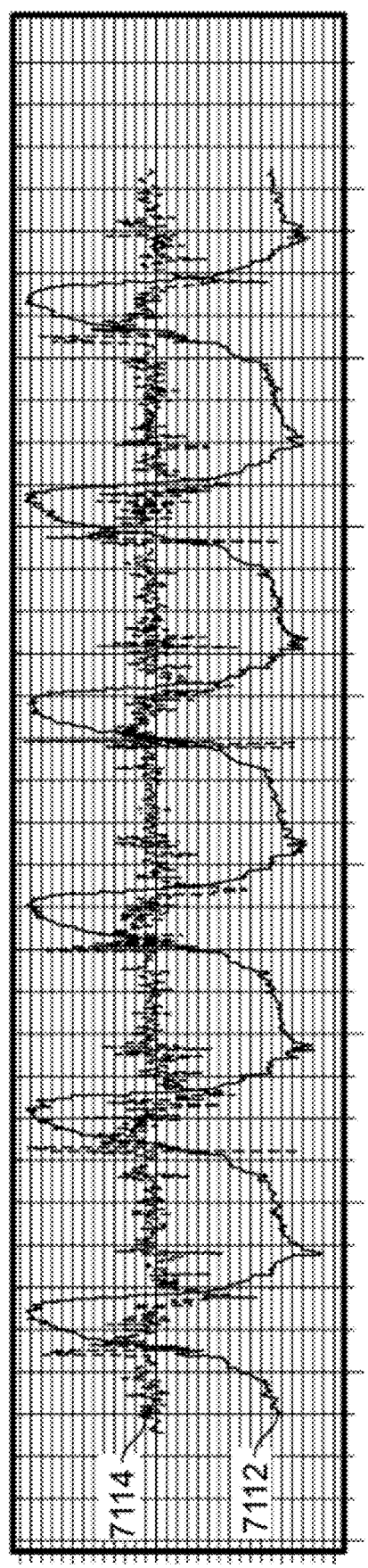

FIG. 7F (i) and (ii) show traces for respiratory flow and airway pressure over time and instantaneous conductance and change in conductance over time respectively.

FIG. 7G (i) and (ii) show traces of respiratory flow and instantaneous conductance indicating a conductance trigger threshold.

FIG. 7H (i) and (ii) show traces for respiratory flow and airway pressure over time and instantaneous conductance and instantaneous impedance over time respectively indicating a patient circuit disconnection.

Figure 7I:
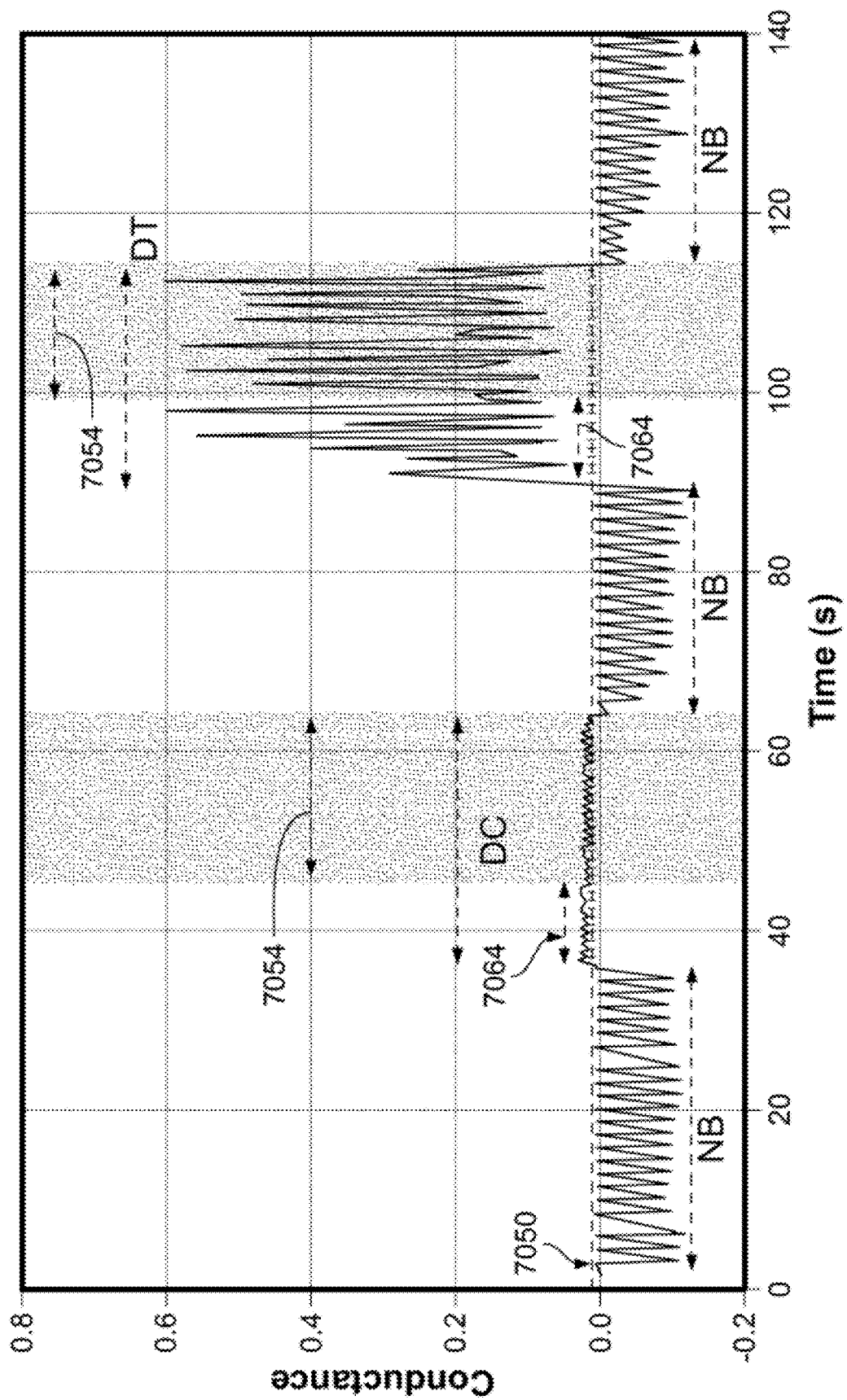

FIG. 7I shows a graph of instantaneous conductance over time with for a paediatric patient with a dual-limbed valved with endotracheal tube patient circuit.

4 DETAILED DESCRIPTION OF EXAMPLES OF THE TECHNOLOGY

Before the present technology is described in further detail, it is to be understood that the technology is not limited to the particular examples described herein, which may vary.

It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

4.2 Treatment Systems

In one form, the present technology comprises a respiratory apparatus or device for treating a respiratory disorder. The respiratory apparatus or device may comprise an RPT device 4000 for supplying pressurised air to the patient 1000 via an air circuit 4170 to a patient interface 3000.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Positioning and Stabilising Structure

The seal-forming structure 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the patient interface. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

4.3.3 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

4.3.4 Decoupling Structure(s)

In one form the patient interface 3000 includes at least one decoupling structure, for example, a swivel or a ball and socket.

4.3.5 Connection Port

Connection port 3600 allows for connection to the air circuit 4170.

4.3.6 Forehead Support

In one form, the patient interface 3000 includes a forehead support 3700.

4.3.7 Anti-Asphyxia Valve

In one form, the patient interface 3000 includes an anti-asphyxia valve.

4.3.8 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

4.4 RPT Device

An RPT device 4000 in accordance with one aspect of the present technology comprises mechanical and pneumatic components, electrical components and is configured to execute one or more algorithms.

An RPT device or ventilator 4000 in accordance with one form of the present technology is shown in FIGS. 4A to 4E. The RPT device 4000 includes a housing 4012, an expiration air inlet port 4014 and an inspiration air outlet port 4016. The air inlet port 4014 and the air outlet port 4016 are connectable to air delivery tubes (not shown) which may be inserted into the trachea of a patient, coupled to a face or nasal mask that fits over the nose or mouth or both of a patient, or otherwise attaches to the patient to assist with breathing. The housing 4012 for the RPT device 4000 may be portable and include a handle 4018 for carrying the ventilator. The housing may have an upper housing case 4020, a chassis 4021 and a lower housing case 4022 that are coupled together to form the external faces of the RPT device. However, it is to be understood that the housing may have other configurations such as only comprising two component parts with an upper and lower casing or may have more than three component parts. The RPT device may include a ventilator or aspects of a ventilator as described in U.S. patent application Ser. No. 13/624,167 filed 21 Sep. 2012 and published as US 2013/0263854 and incorporated herein in its entirety.

The chassis 4021 may provide the structural skeleton for the ventilator assembly. The chassis 4021 may be structured to receive an inlet filter assembly 4036 and inlet seal 4038 respectively described in more detail below. The inlet seal 4038 is also configured to couple to an inlet of a pneumatic block module 4056. Preferably the inlet seal 4038 is formed of a compliant material such as silicone, the inlet seal may be over moulded onto the inlet of the pneumatic block module 4056.

The chassis 4021 may also comprise a pneumatic block seat into which the pneumatic block module 4056 is located for ease of alignment and assembly of the pneumatic block module 4056 within the housing. The chassis 4021 also may include a portion of the handle 4018.

The rear of the chassis 4021 may include a range of interfaces for a variety of connections and switches on the rear panel. For example, interfaces for electrical power connections 4049, switches 4051, data connections 4047 and oxygen connections or inlet port 4046.

The chassis 4021 may also provide a number of interfaces to locate and retain components of the RPT device 4000 such as a cooling fan 4068, printed circuit board (PCB) 4086, and components of an expiratory portion 4031 that is located adjacent the expiration air inlet port 4014 (see FIG. 4E).

The expiratory portion 4031 of the ventilator 4000 is configured to allow the insertion of an expiratory interface module to receive the expired gas from the patient, via the expiration air inlet port 4014. The different expiratory interface modules may include an expiratory valve and an expiratory adaptor.

As seen in FIGS. 4A to 4E, the RPT device 4000 may include a battery compartment to locate and interface with a removable internal battery 4450. A removable battery cover 4052 is provided on the outer bottom surface of the lower housing case 4022 to allow access to insert or remove the battery. A removable expiratory cover 4048, an oxygen sensor cover 4054 and grills 4044 may also be provided on the outer bottom surface to allow component heat venting as seen in FIG. 4D. The lower housing case 4022 may also include an anti-slip foot or grip surface or one or more anti-slip or grip feet 4053, such as a thermoplastic polyurethane (TPU) foot, on the outer bottom surface to prevent the RPT device 4000 from slipping off a smooth surface. The anti-slip or grip feet 4053 may also raise the RPT device 4000 to prevent spilt water from pooling under the bottom of the RPT device. A portion of the handle 4018 is also located within the lower housing case 4022.

As seen in FIG. 4A the upper housing case 4020 provides the top face of the RPT device 4000 and is structured to receive a user interface display device 4024. The housing may include a computer or processor driven user interface display device 4024, such as a liquid crystal display (LCD) adapted to receive touch inputs for the computer. The display device may be flush with a top surface of the housing to be easily visible while the RPT device is in use. An alarm indicator light bar 4026, such as a light emitting diode (LED) light bar, and a button 4028 for disabling an audio or visual alarm may be adjacent the display. However it is to be understood that other known user interface systems may be used such as screens, buttons, dial, keys or combinations thereof. The chassis 4021, lower housing case 4022 and upper housing case 4020 are coupled together for assembly of the complete housing 4012. Fasteners such as screws may be used to assembly the housing 4012 although any other known fasteners may also be used. The chassis 4021 is assembled between the upper housing case 4020 and the lower housing case 4022.

As shown in FIG. 4C, the rear of the housing 4012 may include a filter assembly 4036. Air to be pumped into the lungs of the patient is drawn into the air inlet associated with the filter assembly. The air passes through a permeable filter membrane in the filter and enters an air passage for air flowing to the patient.

The rear of the housing may include data connections 4047 for communications with digital devices such as computer networks, alarm systems, a pulse oximeter (e.g., spO2) and digital recording media. An electrical power connection 4049 and an on-off switch 4051 may also be positioned at the rear of the housing. An input grill 4044-I may provide an inlet for air to cool components and permit dissipation of the heat generated by operation of the internal components (e.g., blower motors and CPU). Movement of the heated air across internal components may be driven by a cooling fan 4068 in the housing, which may be near a heated air output grill 4044-O (shown on bottom of housing in FIG. 4D). In addition, an oxygen (02) inlet port 4046 may be at the rear of the housing, which permits coupling with an oxygen source.

FIG. 4D shows a bottom of the RPT device 4000. The removable expiratory cover 4048, which serves as an external access hatch, provides access to and protection for the compartment of the expiratory portion or section of the housing. Removing the expiratory cover 4048 provides access to any inserted expiratory gas routing module as well as the expiration air inlet port 4014. It also allows for easy removal and replacement of the expiratory gas routing module such as an expiratory valve or expiratory adapter. The expiratory cover 4048 may be tightened to the housing 4012 to reduce excess play by a latch 4050 that may be turned with the fingers. Optionally, in some embodiments, the latch might serve to lock the latch from releasing. An optional latch release button 4050R may be operated to disengage the expiratory cover. The release button 4050R may be depressed to unlatch the expiratory cover 4048. A skilled addressee would understand that alternative ways of removably securing and coupling the expiratory cover 4048 to the housing may also be utilised. The bottom of the housing may also have removable battery cover 4052 for a replaceable internal battery and an oxygen sensor cover 4054 which may be removed to access an oxygen sensor 4064.

FIG. 4E shows the internal components of the RPT device 4000 according to an aspect of the present technology. The RPT device 4000 may include some or all of the following components: an inlet air filter 4034, inlet seal 4038, inlet muffler 4039, an oxygen supply path 4043, a pneumatic block module 4056, an inspiratory portion 4033, safety valve 4085, an expiratory portion 4031, controls and PCB 4086, cooling fan 4068 and internal battery 4450.

The pneumatic block module 4056 is arranged within the RPT device 4000 such that its air passages are aligned with the filter assembly 4036 at the air inlet, the inspiration outlet port 4016 and optionally the oxygen supply path 4043. Arrows indicate the path of the air flow 4035 and the oxygen flow 4045 respectively through the ventilator 4000. The air flow 4035 enters via the inlet air filter 4034 and travels through the filter assembly 4036 and inlet seal 4038 into an inlet muffler 4039 of the pneumatic block module 4056. Optionally an oxygen source may be attached at the oxygen inlet port 4046 and the oxygen flow 4045 is directed through the oxygen supply path 4043 and an oxygen seal into the pneumatic block module 4056 where it is combined with the inlet air flow 4035 within the inlet muffler 4039. Within the pneumatic block module 4056 the air flow 4035 is pressurised by a main blower 4104 (see FIG. 4F). The pressurised air flow 4035 and oxygen flow 4045 are directed out of the pneumatic block module 4056 via outlet muffler 4084 and through the main seal 4040 into the inspiratory portion 4033 and then out the inspiration outlet port 4016 to be delivered to the patient interface (not shown) via an air circuit (not shown).

An oxygen sensor 4064, which may be located in an oxygen sensor compartment of the inspiratory portion 4033, measures the amount of oxygen being delivered to patient. The oxygen sensor 4064 may be mounted in the housing 4012 such that it is easily replaced and adjacent the inspiration outlet port 4016. The oxygen sensor detects the oxygen level of the air being pumped to the patient. Data from the oxygen sensor may be used to trigger alarms related to oxygen concentration and to provide data to the microprocessor to display the oxygen concentration on the user interface. The amount of oxygen supplied may be controlled by adjusting the known volumes of air and oxygen supplied to the patient. However, the oxygen sensor may also optionally be used to regulate the amount of supplemental oxygen to be supplied through the oxygen inlet port 4046.

An oxygen sensor cover 4054 (shown in FIG. 4D) on the bottom of the housing is removable to provide access to the oxygen sensor contained within an oxygen sensor compartment of the housing. The oxygen sensor fits in a mount within the housing and adjacent to the inspiration outlet port 4016. A portion of the air flowing through the inspiration outlet port 4016 is sensed by the oxygen sensor. The sensor generates data signals indicating the oxygen level of the gas. The data is conveyed to a data connection which conveys the data to a processor. The processor analyzes the data to determine the amount of supplemental oxygen to be added to the air being pumped to the patient.

The oxygen source may be a low pressure oxygen supply or a high pressure oxygen supply. For the supply of a high pressure oxygen source an oxygen regulator (not shown) may be located within the oxygen supply path 4043 to reduce the pressure from the high pressure oxygen source before the oxygen enters the inlet muffler 4039. The oxygen inlet port 4046 may be adapted to couple to a range of different oxygen connection adaptors to allow the connection of different types of oxygen connectors used in different jurisdictions including but not limited to male or female diameter index safety system (DISS), sleeve indexing system (SIS), National Institute of Standards Technology (NIST) and Association Francaise De Normalisation (AFNOR).

In an alternative arrangement (not shown), a high pressure oxygen source may be provided after the main blower 4104 such as within the outlet muffler 4084 where it is mixed with the pressurised air. In some examples, the high pressure oxygen may be used to provide the pressure source for the gas flow to the patient. In some arrangements low pressure oxygen may optionally be provided to the air circuit 4170 or the patient interface 3000.

Although the pneumatic block module 4056 is schematically shown as a rectangular shape it is to be understood that the pneumatic block module 4056 may have any shape including a non-symmetrical shape that conforms to a seat in the housing and would minimise the possibility that the pneumatic block module 4056 is improperly inserted into the housing.

The main printed circuit board (PCB) 4086, may be assembled and mounted to the chassis 4021 and located between the chassis 4021 and the lower housing case 4022. The electronic components of the main board may include a processor, electrical connectors to convey data signals from the pneumatic block module 4056 such as an electrical power and data connector for the blower which provides pressurised air to the inspiration outlet port 4016. In this regard, the electrical connectors provide power and signal paths between the electronic components on a PCB in the pneumatic block module 4056 and the electronic components on the main PCB in the housing. The electronic components of the main board may also include a data and power connector for any sensors, such as the oxygen sensor 4064. The electronic components in the housing may control a generation of images for the display device, sound signals for a speaker 4061, such as for producing audible alarms, detect signals from pressure and oxygen sensors, and control the rotational speed of the blower. The RPT device 4000 may optional include a clock connected to the PCB 4086.

FIG. 4F is a schematic of the internal components of the pneumatic block module 4056. The pneumatic block module 4056 includes the main blower 4104 with volute assembly 4108, an inlet non-return valve assembly 4114, an optional oxygen inlet port 4144, a positive end expiratory pressure (PEEP) blower 4124, outlet muffler 4084, safety valve 4085, pressure sensor 4128, flow rate sensor 4130 and flow element 4132 and a PEEP pressure sensor 4142. The volute assembly 4108 forms the majority of the air path and performs some of the critical functions of the pneumatic block module 4056.

The pneumatic block 4056 may include electrovalve 4116 and a flow control electrovalve 4120 that are configured to communicate with and control the non-return valve assembly 4114. A PEEP electrovalve 4136 is configured to communicate with the PEEP blower 4124 to control the supply of the pressure from the PEEP blower 4124 to the expiratory portion 4031. A PEEP pressure tube is coupled between the PEEP expiratory valve and a PEEP supply port in the expiratory portion 4031 to provide the PEEP pressure source. The PEEP pressure sensor 4142 senses the PEEP pressure.

FIG. 4G shows a schematic arrangement for another form of RPT device 4000. The pneumatic path of the RPT device 4000 preferably comprises an inlet air filter 4034, an inlet muffler 4039, a controllable source (pressure generator) 4140 capable of supplying air at positive pressure (preferably a main blower 4104), and an outlet muffler 4084. One or more transducers 4270, such as pressure sensors 4128 and flow rate sensors 4130, are included in the pneumatic path.

The preferred pneumatic block 4056 comprises a portion of the pneumatic path that is located within the external housing 4012.

The RPT device 4000 preferably has an electrical power supply 4210, one or more input devices 4220, a central controller 4230, a therapy device controller 4240, one or more protection circuits 4250, memory 4260, transducers 4270, data communication interface 4280, and one or more output devices 4290. Electrical components 4200 may be mounted on a single Printed Circuit Board Assembly (PCBA). In an alternative form, the RPT device 4000 may include more than one PCBA.

The central controller 4230 of the RPT device 4000 is programmed to execute a set of one or more algorithm modules 4300 in use, preferably including a pre-processing module 4310, a therapy engine module 4320, a therapy control module 4330, and further preferably a fault condition module 4340.

4.4.1 RPT Device Mechanical & Pneumatic Components

An RPT device may comprise one or more of the following components in an integral unit. In an alternative form, one or more of the following components may be located as respective separate units.

4.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4113, for example an antibacterial filter, is located between an outlet of the pneumatic block 4056 and a patient interface 3000.

4.4.1.2 Muffler(s)

An RPT device in accordance with one form of the present technology may include a muffler or a plurality of mufflers 4118.

In one form of the present technology, an inlet muffler 4122 is located in the pneumatic path upstream of a pressure generator 4140.

In one form of the present technology, an outlet muffler 4121 is located in the pneumatic path between the pressure generator 4140 and a patient interface 3000.

4.4.1.3 Pressure Generator

In one form of the present technology, a pressure generator 4140 for producing a flow, or a supply, of air at positive pressure is a controllable blower 4242. For example the blower 4242 may include a brushless DC motor 4244 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

4.4.1.4.1 Flow Rate Sensor

A flow rate sensor 4130 in accordance with the present technology may be based on a differential pressure transducer, for example, an SDP600 Series differential pressure transducer from SENSIRION.

In one form, a signal representing a flow rate from the flow rate sensor 4130 is received by the central controller 4230.

4.4.1.4.2 Pressure Sensor

A pressure sensor 4128 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure sensor 4128 is received by the central controller 4230.

4.4.1.4.3 Motor Speed Transducer

In one form of the present technology a motor speed transducer 4276 is used to determine a rotational velocity of the motor 4244 and/or the blower 4242. A motor speed signal from the motor speed transducer 4276 may be provided to the therapy device controller 4240. The motor speed transducer 4276 may, for example, be a speed sensor, such as a Hall effect sensor.

4.4.1.5 Anti-Spill Back Valve

In one form of the present technology, an anti-spill back valve 4160 is located between the humidifier 5000 and the pneumatic block 4056. The anti-spill back valve is constructed and arranged to reduce the risk that water will flow upstream from the humidifier 5000, for example to the motor 4244.

4.4.1.6 Air Circuit

An air circuit 4170 in accordance with an aspect of the present technology comprises at least one conduit or tube constructed and arranged to allow, in use, a flow of air or gas to travel between two components such as the pneumatic block 4056 and the patient interface 3000.

Figure 1A:
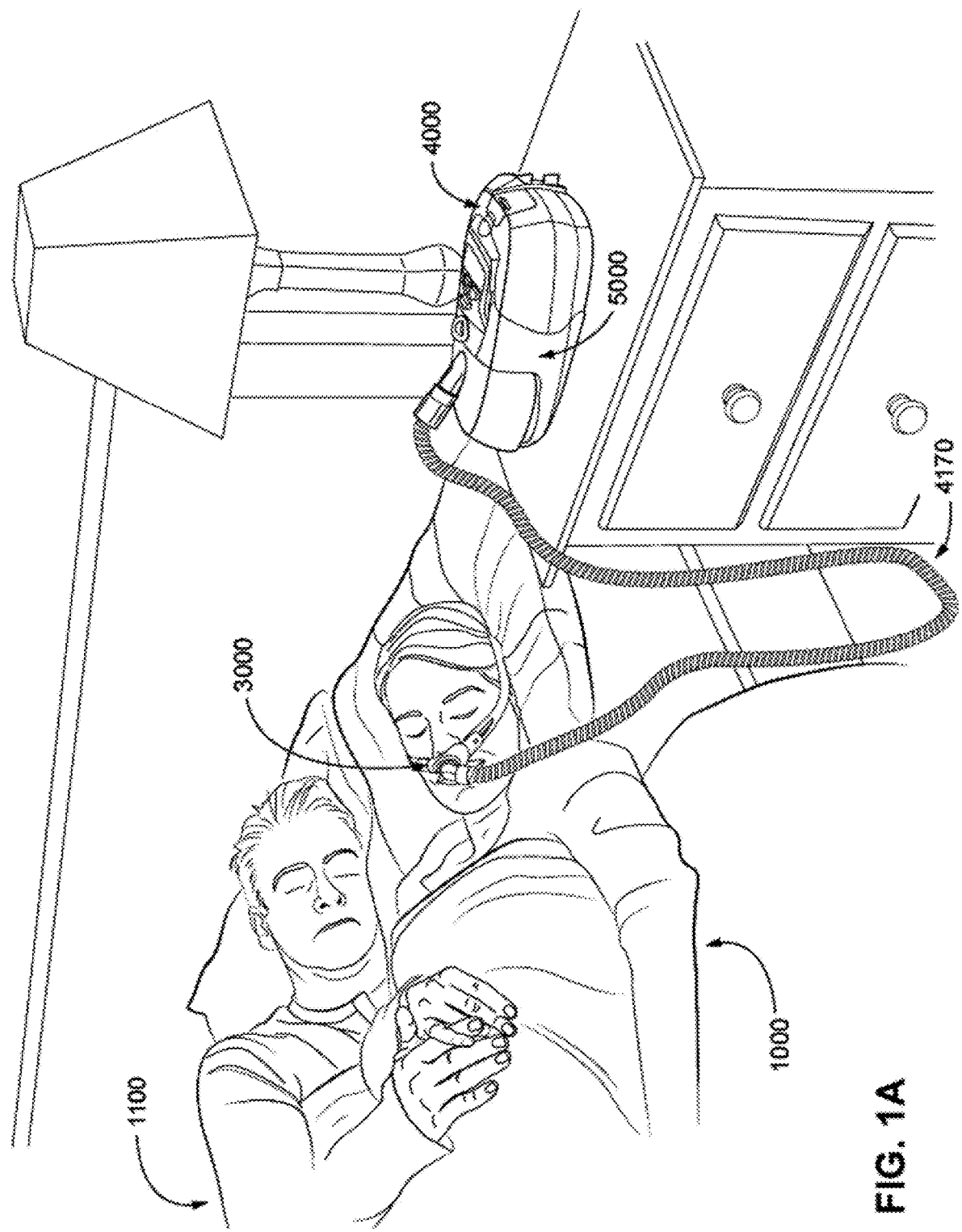
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
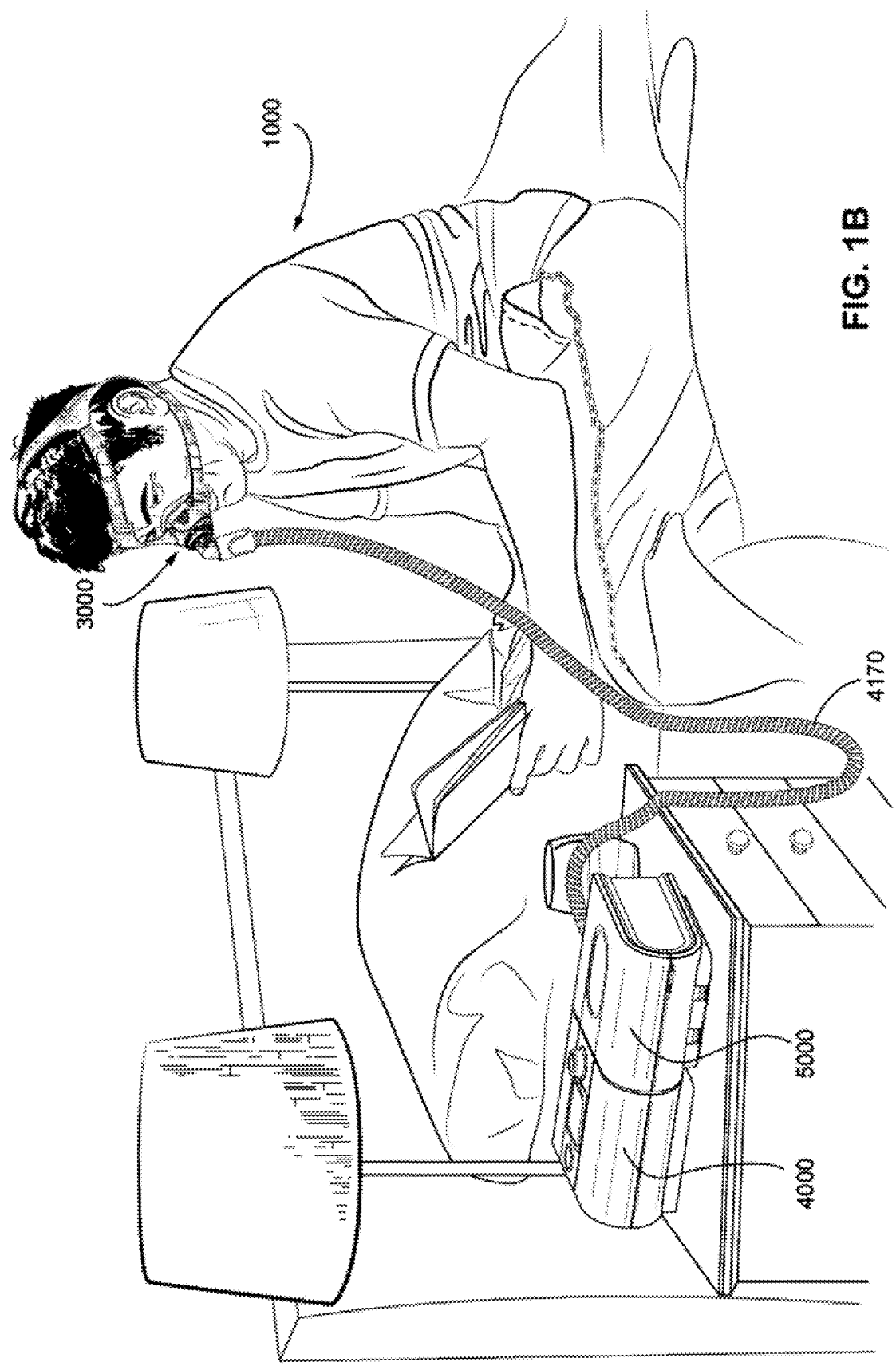
Figure 1C:

In particular, the air circuit 4170 may be in fluid connection with the outlet of the pneumatic block 4056 and the patient interface 3000. Air circuit configurations may include a single limb configuration as shown in FIG. 1A. A single limb circuit may be used with a vent. The vent may be provided as an independent part, such as an anti-asphyxia valve, fitted to an air delivery tube or the vent may be incorporated in as part of the patient interface. The air delivery tube is connected to the outlet of the device, e.g. ventilator or humidifier. In this vented single limb configuration, the inspiratory air or gas flows from the RPT device through the air delivery tube to the patient interface for delivery to the patient and the patient's exhaled gas is exhausted through the vent. The RPT device provides a positive pressure at the vent to ensure the patient exhalant is exhausted.

In an alternative configuration, a single limb circuit may be used with a proximal pneumatic valve. The proximal pneumatic valve is provided near the patient interface end of the air delivery tube. The opposite end of the air delivery tube is connected to the outlet of the device, e.g. ventilator or humidifier. A small tube is also connected between the device and the proximal pneumatic valve to provide a pressure control line. The RPT device applies a control pressure to the proximal pneumatic valve to control opening and closing of an exhaust port of the proximal pneumatic valve. During inspiration, the valve is fully closed, directing all air flow to the patient interface. During expiration, the valve is proportionally controlled to permit the patient to exhale out of the exhaust port but at a specified back-pressure (known as the Positive End Expiratory Pressure (PEEP)). The RPT device also continues to output a bias flow to ensure accurate control of PEEP, and to offset any leak at the patient interface. Air pressure at the patient may be monitored, using a pressure sense line that is connected to a proximal pressure sensor within the RPT device.

In a further configuration, a double limb circuit may be used. A double limb circuit comprises two tubes: an inspiratory tube that delivers air from the RPT device to the patient during inspiration; and an expiratory tube that delivers expired air from the patient to an expiratory port of the RPT device and then out an exhaust port. Geometrically the two tubes may be arranged side-by-side or co-axially. Air flow between the expiratory port and the exhaust port may be regulated by a pneumatic valve located internally within the RPT device.

During inspiration, the valve is fully closed, directing all air flow to the patient. During expiration, the valve is proportionally controlled to permit the patient to exhale out of the exhaust port but at a specified PEEP pressure. The RPT device also continues to output a bias flow to ensure accurate control of PEEP, and to offset any leak at the patient interface. Air pressure at the patient may be monitored during inspiration via a proximal pressure sensor within the RPT device connected to the expiratory tube; and during expiration via an output pressure sensor connected to the inspiratory tube.

In some forms, the air circuit 4170 may comprise one or more heating elements configured to heat air in the air circuit, for example to maintain or raise the temperature of the air. For double limb circuits the inspiratory tube or the expiratory tube or both may be heated. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in U.S. Pat. No. 8,733,349, which is incorporated herewithin in its entirety by reference.

4.4.1.7 Oxygen Delivery

In one form of the present technology, supplemental oxygen 4180 is delivered to one or more points in the pneumatic path, such as upstream of the pneumatic block 4056, to the air circuit 4170, and/or to the patient interface 3000.

4.4.2 RPT Device Electrical Components 4.4.2.1 Power Supply

A power supply 4210 may be located internal or external of the external housing 4012 of the RPT device 4000.

In one form of the present technology, power supply 4210 provides electrical power to the RPT device 4000 only. In another form of the present technology, power supply 4210 provides electrical power to both RPT device 4000 and humidifier 5000. The power supply may include a power management system to control power supplied from internal and external batteries as described in WO 2015/063218, which is incorporated herein in its entirety.

4.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4012, or may, in another form, be in wireless communication with a receiver that is in electrical connection to the central controller 4230.

In one form, the input device 4220 may be constructed and arranged to allow a person to select a value and/or a menu option.

4.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more set of algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

4.4.2.4 Clock

The RPT device 4000 may include a clock 4232 that is connected to the central controller 4230.

4.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

4.4.2.6 Protection Circuits

The one or more protection circuits 4250 in accordance with the present technology may comprise an electrical protection circuit, a temperature and/or pressure safety circuit.

4.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

4.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

4.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.4.2.9.1 Display Driver

A display driver 4292 receives as an input the characters, symbols, or images intended for display on the display 4294, and converts them to commands that cause the display 4294 to display those characters, symbols, or images.

4.4.2.9.2 Display

A display 4294 is configured to visually display characters, symbols, or images in response to commands received from the display driver 4292.

4.4.3 RPT Device Algorithms

4.4.3.1 Pre-Processing Module

A pre-processing module 4310 in accordance with one form of the present technology receives as an input a signal from a transducer 4270, for example a flow rate sensor 4130 or pressure sensor 4128, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

4.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

4.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

4.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate, Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

4.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

4.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude, a base pressure and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

4.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase □ of a current breathing cycle of a patient 1000.

In some forms, known as discrete phase determination, the phase output □ is a discrete variable. One implementation of discrete phase determination provides a bi-valued phase output □ with values of either inspiration or expiration, for example represented as values of 0 and 0.5 revolutions respectively, upon detecting the start of spontaneous inspiration and expiration respectively. RPT devices 4000 that "trigger" and "cycle" effectively perform discrete phase determination, since the trigger and cycle points are the instants at which the phase changes from expiration to inspiration and from inspiration to expiration, respectively. In one implementation of bi-valued phase determination, the phase output □ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold.

Another implementation of discrete phase determination provides a tri-valued phase output □ with a value of one of inspiration, mid-inspiratory pause, and expiration.

In other forms, known as continuous phase determination, the phase output □ is a continuous variable, for example varying from 0 to 1 revolutions, or 0 to 2 □ radians. RPT devices 4000 that perform continuous phase determination may trigger and cycle when the continuous phase reaches 0 and 0.5 revolutions, respectively. In one implementation of continuous phase determination, a continuous value of phase □□ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the inspiration time Ti and the expiration time Te are first estimated from the respiratory flow rate Qr. The phase □□ is then determined as the half the proportion of the inspiration time Ti that has elapsed since the previous trigger instant, or 0.5 revolutions plus half the proportion of the expiration time Te that has elapsed since the previous cycle instant (whichever was more recent).

In some forms of the present technology, a continuous determination of circuit impedance or circuit conductance values based on measured or estimated pressure (P) and flow rate (Q) parameters may be performed. The determined continuous impedance or conductance values may be used to discriminate a passive disconnected circuit from a circuit with a breathing patient attached to enable determination of the circuit connection status. A passive disconnected circuit may provide relatively constant or unvarying determined conductance or impedance values over time. Whilst in contrast, a circuit with a breathing patient attached would provide varying determined conductance or impedance values over time as the patient breaths on the circuit.

In other forms of the present technology, a continuous determination of instantaneous impedance or conductance values based on measured or estimated pressure (P) and flow rate (Q) parameters may be used to estimate the phase of the patient's breathing. The instantaneous impedance or conductance values may be filtered to remove noise from the signal. For instance, while a disconnected circuit will possess a relatively constant measure of conductance or impedance values, a breathing patient connected to the circuit may instead possess a characteristic shape or profile of conductance or impedance values within each respective respiratory phase. Because this profile embodies information about both pressure and flow rate relative to a baseline level of conductance, it may be more sensitive to patient activity than either of these parameters alone. For instance, inspiratory activity may be associated with an increase in delivered flow rate, or a reduction in airway pressure, or both, depending on the circuit type. The inverse may occur with patient expiratory effort. A conductance or impedance profile used to estimate breath phase may therefore be more sensitive and more universal across circuit configurations. Therefore, a conductance or impedance profile or absolute magnitude may be used to trigger and cycle the RPT device in synchrony with the patient's efforts, or be used to provide feedback to the clinician regarding potential asynchrony between the machine's breath phase and that of the patient. For example, detection of 'ineffective' triggering efforts may be performed in a similar manner to that described in U.S. Pat. No. 8,603,006 and U.S. patent application Ser. No. 13/264,4012 published as US 2012/0037159, the contents of both of which are incorporated herein in their entirety.

FIG. 7F(i) shows an exemplary trace of a respiratory flow rate and airway pressure for a breathing machine simulating a patient breathing on the system during CPAP treatment. The airway pressure 7108 remains relatively constant and the respiratory flow rate 7106 cycles through phases of inspiration and expiration. FIG. 7F(ii) shows the instantaneous conductance (G) 7112 that is determined from the respiratory flow rate and airway pressure values. As indicated, the instantaneous conductance shows a similar breathing cycle through phases of inspiration and expiration to that in the flow rate trace 7106. The change in instantaneous conductance over time (dG/dt) 7114 shows a continuously varying conductance with time indicative of a patient breathing on the system.

FIG. 7G(i) shows an exemplary trace of a respiratory flow rate 7106 and the determined instantaneous conductance 7112. An inspiration phase 7102, expiration phase 7104 and a flow rate trigger point 7120 are indicated. The flow rate trigger point 7120 may be used to trigger a new inspiration phase. A pressure trigger point 7130 is also indicated and may be used to trigger a new inspiration phase. In FIG. 7G(ii), the same determined instantaneous conductance 7112 trace is provided and a conductance trigger threshold 7100 is indicated. Each time the instantaneous conductance 7112 is increasing and crosses the conductance trigger threshold 7100 the system may trigger a new inspiration phase. Some examples of where a conductance trigger would trigger a new inspiration are indicated at 7110.

4.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template $\Pi(\Phi)$ is based on a square wave, but with a smooth rise from 0 to 1 for values of phase up to a "rise time" that is substantially less than 0.5 revolutions, and a smooth fall from 1 to 0 for values of phase within a "fall time" after 0.5 revolutions.

In some forms of the present technology, the waveform determination algorithm 4322 selects a waveform template $\Pi(\Phi)$ from a library of waveform templates, dependent on a setting of the RPT device. Each waveform template $\Pi(\Phi)$ in the library may be provided as a lookup table of values Π against phase values $\Phi$. In other forms, the waveform determination algorithm 4322 computes a waveform template $\Pi(\Pi)$ "on the fly" using a predetermined functional form, possibly parameterised by one or more parameters (e.g. time constant of an exponentially curved portion). The parameters of the functional form may be predetermined or dependent on a current state of the patient 1000.

In some forms of the present technology, suitable for discrete bi-valued phase of either inspiration ($\Phi=0$ revolutions) or expiration ($\Phi=0.5$ revolutions), the waveform determination algorithm 4322 computes a waveform template $\Pi$ "on the fly" as a function of both discrete phase $\Phi$ and time t measured since the most recent trigger instant. In one such form, the waveform determination algorithm 4322 computes the waveform template $\Pi(\Phi, t)$ in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template $\Pi(\Phi, t)$. In one such form, the inspiratory portion $\Pi_i(t)$ of the waveform template is a smooth rise from 0 to 1 parametrised by a rise time, and the expiratory portion ILO of the waveform template is a smooth fall from 1 to 0 parametrised by a fall time.

4.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

4.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

4.4.3.2.5 Determination of Apneas and Hypopneas

In one form of the present technology, the central controller 4230 executes an apnea/hypopnea determination algorithm 4325 for the determination of the presence of apneas and/or hypopneas.

The apnea/hypopnea determination algorithm 4325 receives as an input a respiratory flow rate signal Qr and provide as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

4.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further the snore determination algorithm 4326 may comprise a step of filtering the respiratory flow rate signal Qr to reduce background noise, e.g., the sound of air flow in the system from the blower.

4.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal Qr, and determines the presence or absence of a cardiogenic signal. The absence of a cardiogenic signal is taken to be an indication of a closed airway.

4.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

4.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:
A is the amplitude,
$\Pi(\Phi, t)$ is the waveform template value (in the range 0 to 1) at the current value $\Phi$ of phase and t of time, and
$P_0$ is a base pressure.

If the waveform determination algorithm 4322 provides the waveform template $\Pi(\Phi, t)$ as a lookup table of values indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value t of phase.

The values of the amplitude A and the base pressure $P_0$ may be set by the therapy parameter determination algorithm 4329 depending on the chosen respiratory pressure therapy mode.

4.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

4.4.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.
Disconnection of the patient circuit.

Upon detection of the fault condition, the corresponding algorithm signals the presence of the fault by one or more of the following:

Activation of an audible, visual &/or kinetic (e.g. vibrating) alarm
Sending a message to an external device
Logging of the incident

4.4.3.4.1 Patient Circuit Disconnection

According to one form of the present technology, for example as part of the fault detection methods 4340, an RPT device 4000 includes a circuit disconnection detection system that detects the occurrence of a patient circuit disconnection event and may activate a message or alarm to advise a patient, clinician or caregiver that a patient circuit disconnection event has occurred or change a control parameter of the RPT device (such as turn off therapy, decrease pressure, decrease flow or decrease motor speed) or combinations thereof. The patient circuit includes the air circuit 4170 and the patient interface 3000. The patient interface may include invasive, non-invasive, vented or non-vented patient interfaces including a mask, tracheostomy tube (cuffed or uncuffed), straw/tube interface, mouthpiece, or any other such patient interfaces.

The circuit disconnection detection system includes monitoring one or more disconnection parameter(s) that is/are independent of the therapy mode provided, i.e. volume or pressure controlled therapy modes, and of the therapy settings. The disconnection parameter(s) may include a circuit conductance or circuit impedance. In some forms, the instantaneous disconnection parameter $(D_i)$ may be compared to a disconnection threshold $(D_{thres})$ to detect the occurrence of a disconnection event.

In other forms, the instantaneous disconnection parameter $(D_i)$ may be monitored for a relatively constant or non-varying profile indicative of a passive disconnected circuit attached (i.e. patient is not connected to the circuit). In such forms, a level of variability in successively determined instantaneous disconnection parameters over time may provide an indication of a disconnection of the patient circuit. For example, if successively determined instantaneous disconnection parameters have substantially equal values (i.e. have no or very little variability over time) this would indicate a patient circuit disconnection. In contrast, successively determined instantaneous disconnection parameters that have different values (i.e. a level of variability over time) would indicate a patient was connected to the patient circuit.

FIG. 7H(i) shows traces for respiratory flow rate 7106 and airway pressure 7108 when a breathing machine is connected to a system simulating a patient breathing on the system. FIG. 7H(ii) shows a graph of instantaneous conductance 7112 and instantaneous impedance 7116 values determined based on the respiratory flow rate 7106 and airway pressure 7108 from FIG. 7H(i). Arrow 7122 indicates two breathing cycles when a patient circuit is connected to the system. Both the instantaneous conductance 7112 and instantaneous impedance 7116 show varying values over time when breathing on the patient circuit is simulated. At 7118 a circuit disconnection occurs and the instantaneous conductance 7112 and instantaneous impedance 7116 shows little variation over time that suggests a patient circuit disconnection event has occurred.

FIG. 7I shows a graph of instantaneous conductance over time for a paediatric patient connected to an RPT device via a dual value endotracheal tube. The conductance threshold 7050 is indicated. Arrows designated NB indicate periods of normal breathing with the patient circuit connected. Arrow DC indicates a period where de-cannulation has occurred. When the de-cannulation event first occurs there is a delay for a predetermined time limit 7064 until a response to the disconnection event is generated during 7054 to ensure a true disconnection event has occurred. Arrow DT indicates a period when tracheal tube disconnection has occurred. When disconnection of the tracheal tube first occurs there is also a delay for a predetermined time limit 7064 before a response to the disconnection event is generated during 7054. The disconnection event response 7054 may be in the form of activation of an alarm or message. In some forms, an indication may be displayed on the user interface of the RPT device when the disconnection event (DC or DT) is first detected but, in some forms an alarm may only be activated following the expiry of the predetermined time limit 7064.

A disconnection threshold ($D_{thres}$) is a threshold circuit conductance value or a threshold circuit impedance value. For the same circuit and fluid, conductance and impedance may be considered to be inverses of each other. Impedance (resistance) is how much a section of circuit impedes flow when there is a pressure difference applied across it. Conductance is how conducive a section of circuit is to flow when there is a pressure difference applied across it.

FIG. 7A is a flow chart of a patient circuit disconnection detection method 7000 that may be performed by a controller of the RPT device 4000 in one form of the present technology. The method 7000 starts at 7010 and determines the type of patient circuit coupled to the RPT device in 7012. The determination 7012 of the type of patient circuit may include determining the configuration of air circuit 4170 coupled to the RPT device 4000 and/or the type of patient interface 3000 coupled to the air circuit 4170. The determination 7012 of the type of patient circuit may include determining the configuration of air circuit including one or more of invasive, non-invasive, vented or non-vented, single limb circuit or double limb circuit. In one implementation, the type of patient circuit may be entered into the RPT device 4000 via an input device 4220. In another implementation, the type of patient circuit including the configuration of air circuit 4170 or the type of patient interface 3000 or both may be determined by the RPT device 4000. One such implementation involves applying certain predetermined values of pressure and/or flow rate with no patient present during a setup phase of operation and measuring the interface pressure and/or flow rate at each value. The resulting measurements may be used to infer the type of patient circuit. Another such implementation disclosed in PCT Publication no. WO 2010/091462, the entire contents of which are herein incorporated by reference, involves acoustic analysis of sound reflected back from the patient circuit to determine characteristics thereof, including the configuration of air circuit 4170 and/or the type of patient interface 3000. In other such implementations, the sensor(s) of the RPT device 4000 may detect identification of patient circuit type from a tag of the air circuit and/or patient interface, such as by radio frequency identification (e.g., RFID, etc.).

In step 7014 the value of a disconnection threshold ($D_{thres}$) is determined based on the type of patient circuit from step 7012. The disconnection threshold ($D_{thres}$) is set based on a predicted impedance or predicted conductance of the patient circuit and an expected leakage to atmosphere provided by the patient circuit to determine a range of impedance or conductance values that are capable of detecting a 'true' patient circuit disconnection while discriminating a 'true' disconnection from a level of background leak expected in the patient circuit during use. The disconnection threshold may be empirically determined based on pre-characterisation of a range of different patient circuit types to determine the appropriate range of impedance or conductance values. In some forms, the RPT device 4000 may use a lookup table to set an initial value of the disconnection threshold based on the type of patient circuit coupled to the RPT device.

Optionally in some forms, patient information 7013 may also be provided to the RPT device and be used as a basis for determining or setting the disconnection threshold. The patient information may include at least one of: the type of patient (e.g. adult or paediatric), the patient's weight, the patient's height, and the patient's age.

To monitor for the disconnection of a patient circuit during therapy, the RPT device may be configured to repeatedly detect a measure or estimate of instantaneous pressure (Pm) in the patient interface and instantaneous flow rate (Qt) in the patient circuit in step 7016. As mentioned previously, the RPT device may include one or more of a pressure sensor 4128 or flow rate sensor 4130 to measure or estimate the pressure or flow rate respectively. In step 7018, an instantaneous disconnection parameter ($D_i$) may be calculated based on the instantaneous pressure (Pm) and flow rate (Q) inputs. The instantaneous disconnection parameter ($D_i$) may be calculated as either a circuit impedance value or a circuit conductance value.

In step 7020, the instantaneous disconnection parameter ($D_i$) is compared to the disconnection threshold ($D_{thres}$) to detect whether a circuit disconnection event has occurred. If the comparison indicates that a circuit disconnection event has occurred, then a Boolean disconnection indication (Disc) may be set to True. The True disconnection indication may signal the occurrence of a circuit disconnection event. In step 7022 the system detects whether a disconnection event has been detected and if the result is NO then in step 7024 a no-disconnection status is signalled by setting the disconnection indication (Disc) to False, and the method 7000 cycles back to repeat the detection of instantaneous pressure and flow rate values in 7016. If in step 7022 the result is YES, a disconnection event is signalled in 7026 by setting the disconnection indication (Disc) to True. The method 7000 may continue to monitor the disconnection status by cycling back to the detection of instantaneous pressure and flow rate values in 7016. In some forms, a True disconnection indication may be provided when a disconnection event is detected, but when no disconnection event is detected, the method 7000 cycles back to repeat the detection of instantaneous pressure and flow rate values at step 7016.

The setting of the disconnection indication in 7026 may be followed by activation of a disconnection alarm, message, counter, or timer. In some forms, the RPT device may provide a first indication when the disconnection event is first detected. For example the output device 4290 may include a display 4294 on which an indication that a circuit disconnection event has been detected may be provided. The indication on the display 4294 may be in the form of a message or light (e.g. light turned on, changed colour or flashing LED) or other form of visual indication. The RPT device may also or alternatively start a counter or timer to monitor the continuous detection of a disconnection event for a predetermined period of time. The activation of an alarm or message may be provided only after the continuous detection of the disconnection event for the predetermined period of time. Alternatively, a second indication, different from the first indication, may be provided such as in the form of an audio indication, e.g. an alarm, when the disconnection event is continuously detected for the predetermined period of time. In some forms, the status of the disconnection parameter, as compared to the threshold, may be continuously indicated on the output device 4290 of the RPT device 4000. Such a disconnection status indication may provide real-time feedback to a user, caregiver or clinician as to the status of the disconnection detection and assist in adjusting the level of the disconnection threshold ($D_{thres}$) to ensure a disconnection event is correctly detected. The disconnection status may indicate whether the currently set disconnection threshold ($D_{thres}$) would have provided a disconnection indication or not, and the user, caregiver or clinician may use this status information to adjust or tune the disconnection threshold ($D_{thres}$). For example the user, caregiver or clinician may purposely disconnect the patient circuit or provide a patient interface leak to test whether the currently set disconnection threshold ($D_{thres}$) would detect a circuit disconnection event and provide a disconnection indication (Disc) in either of these situations. The disconnection threshold ($D_{thres}$) may be adjusted to prevent a disconnection indication being provided when a patient interface leak occurs whilst still detecting a patient circuit disconnection event. The disconnection status may allow monitoring of the performance of the patient circuit disconnection detection system.

FIG. 7B is a flow chart of a circuit disconnection detection method 7000A that may be performed by a controller of the RPT device 4000 in another form of the present technology. In this form, the disconnection indication (Disc) must be provided for a predetermined time limit before a disconnection alarm is activated. The method 7000A is similar to the method 7000 illustrated in FIG. 7A from the start 7010 to the "Is disconnection event detected" step 7022, like item numbers indicating the same or substantially similar steps. Similarly in the method 7000A, if step 7022 detected no disconnection event, a disconnection indication (Disc) is set to false in step 7024 or maintained as false if it was previously set to false. However in addition, a timer is reset to zero in step 7038 prior to returning to step 7016 to monitor the instantaneous pressure and flow rate.

Similarly if in step 7022 the result is YES, i.e. a disconnection event is detected, then a disconnection indication (Disc) is set to true in step 7026 or maintained as true if was previously set to true. In addition, in step 7032, a timer is started, if not previously started, or incremented, if the timer had been previously started. The timer may count up or down to a predetermined time limit. The disconnection indication (Disc) may also be displayed on the output device 4290 (e.g. user interface) of the RPT device 4000 to indicate to the user, caregiver or clinician the disconnection status. Such a display of the disconnection indication may assist in tuning the disconnection threshold ($D_{thres}$) or in monitoring the performance of the patient circuit disconnection detection system or both as discussed above.

In step 7034, the current value of the timer is compared to the predetermined time limit. The predetermined time limit may include a set time duration such as 5 to 60 seconds, or 5 to 30 seconds, or some other time limit. Alternatively the predetermined time limit may be in the form of a counter and include a count of a predetermined number of breaths, such as 1, 2, 3, 4, 5, 6, 7, 8, 9, 10 or more breaths. The set time limit may be adjustable, via an input device 4220, for a set time length in seconds or minutes or for a set number of breaths.

If the current value of the timer is not greater than or equal to the predetermined time limit then the method 7000A cycles back to continue monitoring the instantaneous pressure and flow rate inputs and detecting the disconnection status over time.

If the current value of the timer is greater than or equal to the predetermined time limit, then an alarm or message may be activated at step 7040 to signal to one or more of a patient, clinician, or caregiver that a patient circuit disconnection event has occurred. Optionally, the method 7000A cycles back to continue to monitor the instantaneous pressure and flow rate inputs and detect the disconnection status.

Thus, in this form, when a 'true' disconnection event is first detected, the timer commences and continues to monitor the continued occurrence of a disconnection event until the predetermined time limit has been reached or exceeded.

Once a disconnection event has been continuously detected for the predetermined time limit, the RPT device will activate an alarm or message. However, if before the predetermined time limit is reached a 'false' disconnection indication is detected, then the counter is reset and the predetermined time limit is not reached, consequently no alarm or message is activated. The disconnection system continues to determine the instantaneous disconnection parameter and monitor the disconnection status.

An instantaneous disconnection parameter may be calculated as either or both of an impedance and a conductance based on a measured or estimated pressure at the patient interface (Pm) and the measured or estimated volumetric flow rate (Qt) from the RPT device 4000. As mentioned previously, the RPT device may include one or more of a pressure sensor 4128 or flow rate sensor 4130 to measure or estimate the pressure or flow rate respectively. The instantaneous disconnection parameter value may be filtered to remove noise in the signal.

In one form of the present technology, the instantaneous disconnection parameter may be calculated based on a measurement or estimation of pressure at the patient interface (Pm) and the measured flow rate (Qt). The disconnection parameter may be calculated based on the following equation related to pressure loss at the patient interface:

$$P_m = Z \times \rho^{0.75} \times Q_t^{1.75} \quad [1]$$

wherein Pm is the pressure at the patient interface, Z is the impedance, $\rho$ is the air density and Qt is the measured flow rate. In some forms, air density may be estimated based on ambient pressure and a gas temperature. Ambient pressure and gas temperature may be measured via sensors or entered into the device via the input device.

This equation [1] may be rearranged to provide an impedance (Z) determination that may be used as one form of the instantaneous disconnection parameter:

$$Z = \frac{P_m}{\rho^{0.75} \times Q_t^{1.75}} \quad [2]$$

In such a form, the disconnection threshold will be an impedance threshold, and if the instantaneous impedance is less than the disconnection threshold impedance, then the patient circuit is determined to be disconnected.

The equation [2] may be inverted to provide a conductance (G) determination that may be used as another form of the instantaneous disconnection parameter:

$$G = \frac{\rho^{0.75} \times Q_t^{1.75}}{P_m} \quad [3]$$

In such a form, the disconnection threshold will be a conductance threshold, and if the instantaneous conductance is greater than the disconnection threshold conductance for a predetermined time limit then the patient circuit is determined to be disconnected.

In some forms of the present technology, the instantaneous disconnection parameter is determined at predetermined time intervals. The predetermined time interval may include one or more breaths or a time duration in milliseconds or seconds. In one form, the instantaneous disconnection parameter is determined at least once during each breath. For example, the instantaneous disconnection parameter is determined during the inspiration phase of the breath. In other forms, the instantaneous disconnection parameter is determined multiple times per breath including during an inspiration phase and an expiration phase. The instantaneous disconnection parameter is determined based on inputs of pressure (P) and flow rate (Qt) that are provided at least once per breath, preferably at least once during an inspiration phase or at least once during an inspiration phase and at least once during an expiration phase.

In other forms the instantaneous disconnection parameter may be detected at predetermined time intervals.

The instantaneous pressure and flow rate inputs may be measured or estimated based on sensor signals that are sampled during the breathing cycle. The inspiration sampling time may be configured to minimise the effect of large patient inspiratory effort on the signals, such as at the end of the inspiratory portion of a breath. For example, inspiration pressure and flow rate inputs may be determined at a predetermined time prior to cycling (e.g. 10-30 milliseconds prior to cycling) or a predetermined time after a new breath is triggered (e.g. 100-300 milliseconds after triggering). Expiration pressure and flow rate inputs may be determined at a time when periods of unstable flow may be avoided, such as unstable flow associated with valve switching. For example the expiration pressure and flow rate inputs may be determined at a predetermined time after cycling (such as 100-300 milliseconds or 200-250 milliseconds) or a predetermined time prior to triggering (such as 10-50 milliseconds prior to triggering). The sampling times may be chosen based on whether a measurement of patient effort is required or not. If patient effort measurements are required, then sampling may occur at a time just after the detection of a triggering and cycling event. Alternatively, to make a measurement with minimum patient effect, sampling may occur at a time just prior to triggering and cycling.

A skilled addressee would appreciate that other pressure loss equations may be used to determine the instantaneous disconnection parameter (conductance or impedance).

In some forms, the circuit disconnection detection system is always enabled to detect patient circuit disconnection. In other forms, the circuit disconnection detection system may be disabled for non-dependent patients (i.e. spontaneously breathing patients) or depending upon the circuit configuration coupled to the RPT device. Preferably, the circuit disconnection detection system cannot be disabled for ventilation dependent patients.

In some forms, the RPT device may allow the disconnection alarm to be muted for a predetermined period of time, such as for 30 seconds to 5 minutes, or 30 seconds, 60 seconds or 120 seconds or some other length of time, after it has been activated. The disconnection alarm may be muted via the input device 4220 of the RPT device 4000, for example by pressing a button or dial on the input device 4220. In some forms, the length of time of the alarm mute may be adjustable via the input device 4220. The adjustment may be performed by the clinician, patient or caregiver.

In some forms of the present technology, the disconnection threshold ($D_{thres}$) may be adjusted based on a sensitivity setting. The sensitivity setting may be used to adjust the disconnection threshold ($D_{thres}$) to tune the level of disconnection event detection. The sensitivity setting may be considered a disconnection tolerance factor. The sensitivity setting may be manually tuned by a user, caregiver or clinician to test the disconnection system with the patient circuit coupled, including the air circuit 4170 and the patient interface 3000, prior to connecting the patient. Tuning the sensitivity setting is configured to increase the probability of successfully detecting circuit disconnection and/or reduce the probability of falsely detecting circuit disconnection and activating an alarm or message during therapy. A display of the disconnection indication (Disc) on the output device 4290 of the RPT device 4000 may be used to assist in tuning the sensitivity setting.

In one form, the sensitivity setting may be set manually during a testing phase based on empirically testing a range of sensitivity settings to determine the minimum sensitivity setting at which the disconnection threshold is just sensitive enough to correctly detect a circuit disconnection event as indicated by the disconnection indication step 7026. The sensitivity setting may be set at the determined sensitivity setting or at one or more levels of increased sensitivity to guard against partial occlusion of the air circuit impairing the effectiveness the disconnection system during disconnection. The testing phase may be prior to providing therapy or whilst providing therapy, such as at an initial phase of therapy.

In some forms, during the testing phase for the sensitivity setting, the RPT device may disable or reduce the predetermined time limit required to activate the disconnection alarm to allow prompt feedback to aid adjustment of the sensitivity setting.

In some forms, the RPT device may be configured to provide feedback via the output device 4290, such as on a display 4294, as to the level of the sensitivity setting that would have detected a circuit disconnection event based on the currently measured instantaneous disconnection parameter. The feedback in sensitivity setting may be provided as real-time feedback or saved in a memory for subsequent analysis.

The sensitivity setting may be a percentage between 1 and 100%, such as 5 to 100%, or a fraction or value such as between 0.01 and 1, or an arbitrary scale. In some forms, the sensitivity setting may be selected from a predetermined range of settings between an upper and lower limit, such as 5% increments between 5% and 95%. The disconnection threshold may be adjusted by the sensitivity setting to provide a final disconnection threshold that may be used in the comparison 7020 with the instantaneous disconnection parameter. In some forms, the higher the sensitivity setting, the more tolerant the final disconnection threshold will be to leak from the system. Thus, a lower sensitivity setting will be more sensitive to disconnection detection than a higher sensitivity setting. However, it is acknowledged that a skilled addressee would understand that the sensitivity setting may be configured in other manners such that a higher sensitivity setting will be more sensitive to disconnection detection than a lower sensitivity setting.

In some forms, the sensitivity setting may be set as a default sensitivity setting based on one or more of the configuration of the air circuit, the type of patient interface, or the type of patient. In other forms, the default sensitivity setting may be set based on analysis of previous sensitivity data saved in memory from a previous therapy session or from a previous learn period.

FIGS. 7C to 7E disclose example testing phases for the same patient circuit configuration under the same conditions but with different sensitivity settings. The patient circuit includes a single limb circuit with patient interface mask being used by an adult patient. In these tests, a circuit disconnection occurs between 52 and 74 seconds and a high leak occurs between 96 and 153 seconds. The instantaneous conductance value (G) is required to remain above the conductance threshold for a predetermined time limit such as at least 5 consecutive breaths to generate a disconnection event response such as an alarm or message. In each of FIGS. 7C to 7E the top trace shows the changes in instantaneous conductance (G) value over time in seconds and the lower trace show the changes in instantaneous pressure (Pm) 7108 and instantaneous flow rate (Qt) 7106 over time in seconds.

FIG. 7C shows a test with a 15% sensitivity setting that sets the conductance threshold 7050 as indicated by the dashed line on the conductance trace. When the instantaneous conductance (G) exceeds the conductance threshold 7050 as indicated at 7052 and 7056 a timer starts to count to assess if the instantaneous conductance continuously exceeds the threshold for a predetermined time limit as indicated by arrow 7064. After the predetermined time limit 7064 is exceeded, a disconnection event response 7054 is initiated, which may include activating a message or alarm during this time. However, each time the instantaneous conductance exceeds the conductance threshold 7050, a disconnection event may be detected, as indicated by the dots provided along the conductance threshold dashed line. A single disconnection event (i.e. a single dot) will not generate a disconnection event response 7054. When the circuit is re-connected, the instantaneous conductance value drops below the conductance threshold at point 7060, and the disconnection event response is discontinued, i.e. the message or alarm is deactivated. The shaded block indicated by arrow 7058 also indicates a period of time where the instantaneous conductance has continuously exceeded the disconnection threshold 7050 for longer than a predetermined time limit 7064 and a disconnection event response is generated, e.g. a message or alarm. However, in block 7058, a disconnection event is wrongly detected as a circuit disconnection has not occurred but a high leak event has occurred, which has wrongly indicated a circuit disconnection. Thus, the disconnection threshold is too sensitive, such that the level of the sensitivity setting needs to be increased to decrease the level of sensitivity to prevent false indications of circuit disconnection events. The pressure 7108 and flow rate 7106 traces are provided in the lower trace and indicate that a circuit disconnection has occurred between 52 and 74 seconds as the cyclic respiratory flow rate trace 7106 is no longer present. However, between 96 and 153 seconds, the cyclic respiratory flow rate trace 7106 remains present indicating that the patient is continuing to breathe on the patient circuit.

In FIG. 7D, the sensitivity setting has been increased to 35% to decrease the sensitivity of the conductance threshold 7050. As above, the instantaneous conductance exceeds the conductance threshold 7050 at point 7052 and continues to exceed the conductance threshold for a predetermined time limit 7064 to result in a disconnection event response 7054. As above, each time the instantaneous conductance exceeds the conductance threshold 7050 a disconnection event may be detected as indicated by the dots provided along the conductance threshold dashed line 7050. The disconnection event response 7054 includes activating a message or alarm to indicate the occurrence of a circuit disconnection event when a disconnection indication has been continuously detected for a predetermined time limit. When the circuit is re-connected, the instantaneous conductance value drops below the conductance threshold at point 7060 and the disconnection event response is discontinued, i.e. the message or alarm is deactivated. The instantaneous conductance threshold 7050 is again exceeded at 7056 but is not continuously exceeded for the predetermined time limit as the instantaneous conductance drops below the conductance threshold at 7060 resulting in no disconnection event response, i.e. no alarm or message being activated. However, due to the high leak event, the instantaneous conductance value again exceeds the conductance threshold at 7062 and remains above the conductance threshold for the predetermined time limit 7064 leading to a second disconnection event response (e.g. activation of a message or alarm) indicating a circuit disconnection event in block 7058. However, as above, this is a false detection of a circuit disconnection event caused by high leak rather than an actual disconnection of the circuit. Consequently, the sensitivity setting of 35% may still provide some false disconnection indications if high leaks occur.

In FIG. 7E, the sensitivity setting has been further increased to 45% to further decrease the sensitivity of the conductance threshold 7050 in an attempt to prevent false disconnection event detections. As above, the instantaneous conductance exceeds the conductance threshold 7050 at point 7052 and continues to exceed the conductance threshold for a predetermined time limit 7064 to result in a disconnection event response 7054. The disconnection event response 7054 provides a message or alarm to indicate the occurrence of a circuit disconnection event. When the circuit is re-connected, the instantaneous conductance value drops below the conductance threshold at point 7060 and the disconnection event response is discontinued, i.e. the message or alarm is deactivated. The instantaneous conductance threshold 7050 is again exceeded at 7056 and 7062 as indicated by the dots on the dashed disconnection threshold line 7050, but only for brief time periods that are less than the predetermined time limit 7064 before the instantaneous conductance drops back below the conductance threshold at 7060 resulting in no disconnection event response, i.e. no alarm or message being activated. This indicates that for this example, the most appropriate sensitivity setting for this patient circuit configuration would be 45% or more to avoid false detection of high leak events as circuit disconnection events.

In some forms of the present technology, the circuit disconnection detection system may include disconnection mitigations to improve the likelihood of a correct activation of a disconnection alarm or message. Such mitigations may be performed following the initial detection of a disconnection event, for example, via the monitoring of the instantaneous disconnection parameter for comparison to the disconnection threshold or for a relatively constant or non-varying profile indicative of a passive disconnected circuit. The disconnection mitigations may include detection of characteristics that either confirm the disconnection event or identify the occurrence of a false detection.

False disconnection mitigations, such as for disqualifying previously/contemporaneously detected disconnection events, may include detection of one or more of the following respiratory indicators which indicate that a patient remains connected to the patient circuit:
- an expiratory flow indicative of expiratory effort;
- an inspiratory flow indicative of inspiratory effort;
- a difference in the instantaneous disconnection parameter calculated during the inspiration phase compared to the instantaneous disconnection parameter calculated during the expiration phase of the breathing cycle;
- a negative instantaneous disconnection parameter during an expiratory portion, i.e. detection of either a negative respiratory flow rate (Qr) or a negative pressure in the patient interface (Pm) during an expiratory portion; or
- a comparison of the instantaneous disconnection parameter to a calculated variance of previous values of the instantaneous disconnection parameters, the variance calculated based on a long term measure of a plurality of the immediately preceding values of the instantaneous disconnection parameters from the same phase (i.e. from inspiration phase or expiration phase). The long term measure is based on a predetermined time constant such as 30 seconds to 300 seconds, 60 seconds to 120 seconds, a predetermined number of breath phases, or some other time limit.

In the case of multiple instantaneous disconnection parameters being determined within each breath phase, variation between these instantaneous disconnection parameters within the breath phase may indicate an 'active' load (i.e. patient activity), and serve as a condition to overrule false disconnection indications.

If one or more of the above false disconnection mitigations are detected after a circuit disconnection event is detected, then the circuit disconnection event is qualified as false and the disconnection indication (Disc) is set to False.

Confirmation disconnection mitigations may include detecting that an outlet flow rate exceeds a predetermined threshold, such as flows associated with extreme leak or associated with dispersion of fluid within the circuit or within a humidifier.

The type of disconnection mitigations that may be utilised may depend upon the patient circuit being used.

In some forms, the RPT device may be configured to detect re-connection of the patient circuit. In response to detecting the re-connection of the patient circuit, the RPT device may be configured to perform one or more of recommencing therapy, discontinuing the disconnection event response, and generating a different response to the re-connection. A re-connection event may be detected by a comparison of the instantaneous disconnection parameter to a re-connection threshold indicating a change in circuit disconnection status or a false disconnection indication. In another form, the re-connection event may be detected by detecting a variation in the instantaneous disconnection parameter over a breathing cycle to indicate that a patient is breathing on the patient circuit.

Alternatively, a re-connection event may be detected by an abrupt change in the instantaneous disconnection parameter, indicative of a patient's presence being restored at the patient interface, be it inhaling, exhaling, or occluding the patient interface. The required change in the instantaneous disconnection parameter may be based on satisfying a second threshold of increase or decrease in the instantaneous disconnection parameter, or based on a discontinuity in the instantaneous disconnection parameter over time. For example, when an impedance is used, an increase in the instantaneous disconnection impedance above a second impedance threshold may signal the triggering of a breath. Alternatively when a conductance is used, a decrease in the instantaneous disconnection conductance below a second conductance threshold may signal the triggering of a breath.

A re-connection event may be indicated after the detection of a single re-connection or after a plurality of re-connection detections following the activation of a disconnection alarm or message. The length of time that the true disconnection event has been indicated prior to the re-connection event being detected may be used as a basis for determining the rate of the response to the re-connection. In other forms, the rate of response to re-connection may be determined as a function of the patient circuit.

4.4.3.4.2 Monitoring Therapy Using Conductance or Impedance

While the previously discussed methods are implemented for detection of disconnection/re-connection events as opposed to high leak events, in alternative forms of the fault detection methods 4340, a conductance or impedance value may be used to detect occurrence of particular respiratory events occurring within the system. In one such form, a conductance or impedance value may be used to detect obstructions and, optionally, activate an alarm or message. The changes in conductance or impedance over time may be monitored and compared to a recent baseline for the treatment session. A recent baseline may include determining a short-term average for the conductance or impedance values over time, such as for 2-10 seconds or 2-10 breaths. For example, an unchanging conductance of nominally zero (or consistently excessive impedance) would indicate a complete blockage somewhere in the patient circuit or within the patient's airways. Alternatively, a value associated with total obstruction may be deduced relative to recent baseline conductance (or impedance) measurements. Using conductance or impedance may provide a configuration-free means of detecting obstruction that is consistent across therapy modes, and may be automatic and always available.

In still other forms of the fault detection methods 4340, conductance or impedance values may be used for detecting "flow starvation" in a patient. Flow starvation may occur on spontaneously breathing patients ventilated in volume target modes. It occurs if the configured peak inspiratory flow rate does not meet the patient's inspiratory demand. Flow starvation results in the patient attempting to suck more flow out of the RPT device and circuit than the ventilator can or will supply, resulting in a reduction in airway pressure. This 'suck' may be seen as an anomalously high conductance value compared to recent baseline conductance values or as a particular profile during inspiration (e.g. a conductance higher at early-to-mid inspiration than at the end of inspiration). The anomalously high conductance value indicating flow starvation would be detected when patient circuit connection is confirmed based on detection of changing conductance over the breathing cycle or detection of other false disconnection mitigations as discussed above.

In some such forms, the conductance value during an inspiration phase may be compared to a third conductance threshold and if the instantaneous conductance value exceeds the third conductance threshold and inspiratory flow is detected then a flow starvation event may be detected.

Similarly, a low impedance value compared to recent baseline impedance values or of a particular profile during inspiration may signal a flow starvation event. A distinctive profile during inspiration may include a low impedance value at the beginning of inspiration and then an increase in impedance to a higher level at the end of inspiration. A third impedance threshold may be provided and if an instantaneous impedance value from an inspiration phase is below the third threshold and inspiratory flow is detected then a flow starvation event may be detected.

Upon detection of a flow starvation event the RPT device may provide an indication to the caregiver or clinician. The indication may be activation of a message on the output device 4290 or activation of an alarm. In some forms, the detection of a flow starvation event may result in adjustments of therapy parameters.

In yet other forms of the fault detection methods 4340, conductance or impedance values may be used for detecting insufficient vent flow. This condition may be detected as an anomalously low conductance value compared to recent baseline conductance values or as an anomalously high impedance value compared to recent baseline impedance values. The anomalously low conductance value indicating insufficient vent flow may be detected when patient circuit connection is confirmed based on detection of changing conductance over the breathing cycle or detection of other false disconnection mitigations as discussed above.

In some such forms, the conductance value during an inspiration phase may be compared to a fourth conductance threshold and if the instantaneous conductance value is lower than the fourth conductance threshold then an insufficient vent flow condition may be detected. Alternatively, a fourth impedance threshold may be provided and if an instantaneous impedance value exceeds the fourth impedance threshold then an insufficient vent flow condition may be detected.

Upon detection of an insufficient vent flow condition, the RPT device may provide an indication to the caregiver or clinician. The indication may be activation of a message on the output device 4290 or of an alarm. In some forms, the detection of an insufficient vent flow condition may result in adjustments of therapy parameters.

In still other forms of the fault detection methods 4340, a conductance or impedance value may be provided to detect inappropriate settings for rise time or peak inspiratory flow (PIF), consistent with the patient expending substantial effort during a period where unloading of the patient is typically desired. Conductance or impedance may be continuously calculated over a breathing cycle. A high conductance or low impedance value at the start of inspiration compared to the conductance or impedance value at the end of inspiration may indicate an inappropriate setting for rise time or peak inspiratory flow (PIF). The conductance or impedance value at the beginning of inspiration may be compared to a conductance or impedance value at the end of inspiration and based on the level of difference, an adjustment in the rise time setting or PIF setting may be provided.

4.5 Humidifier

4.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.5.2 Humidifier Mechanical Components

4.5.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory pressure therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one arrangement, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

4.5.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

4.5.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

4.5.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

4.5.3 Humidifier Electrical & Thermal Components

The humidifier 5000 may comprise a number of electrical and/or thermal components such as those listed below.

4.5.3.1 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

4.5.3.1.1 Pressure Transducer

One or more pressure transducers 5212 may be provided to the humidifier 5000 in addition to, or instead of, a pressure sensor 4128 provided in the RPT device 4000.

4.5.3.1.2 Flow Rate Transducer

One or more flow rate transducers 5214 may be provided to the humidifier 5000 in addition to, or instead of, a flow rate sensor 4130 provided in the RPT device 4000.

4.5.3.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

4.5.3.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

4.5.3.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

4.5.3.3 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

4.6 Breathing Waveforms

FIG. 6A shows a model typical breath waveform of an adult person while sleeping. The horizontal axis is time, and the vertical axis is respiratory flow rate. While the parameter values may vary, a typical breath may have the following approximate values: tidal volume, Vt, 0.5 L, inspiration time, Ti, 1.6 s, peak inspiratory flow rate, Qpeak, 0.4 L/s, expiration time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot, is about 40%.

FIG. 6B shows a patient during Non-REM sleep breathing normally over a period of about ninety seconds, with about 34 breaths, being treated with Automatic PAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory air flow, and the scale ranges from −1 to +1 LPS in a vertical direction, and with inspiration positive. Thoracic and abdominal movement are shown in the third and fourth channels.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during expiration, and slightly lower during inspiration. In some forms, the pressure will vary between different respiratory cycles of the patient, for example, being increased in response to detection of indications of partial upper airway obstruction, and decreased in the absence of indications of partial upper airway obstruction.

Flow rate: The volume or mass of air or gas delivered per unit time. Flow rate as volume per unit time may be referred to specifically as the "volumetric flow rate"; in the present disclosure, this is the quantity meant by the unqualified term "flow rate". Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory disease.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

4.7.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inspiration time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Tidal volume (Vt): The volume of air inhaled or exhaled during normal breathing, when extra effort is not applied.

(inspiration) Time (Ti): The duration of the inspiratory portion of the respiratory flow rate waveform.

(expiration) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.7.3 RPT Device Parameters

Leak: The word leak will be taken to be an unintended flow of air. In one example, leak may occur as the result of an incomplete seal between a mask and a patient's face. In another example leak may occur in a swivel elbow to the ambient.

4.7.4 Terms for Ventilators

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory portion. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the inspiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

Ventilator: A mechanical device that provides pressure support to a patient to perform some or all of the work of breathing.

4.7.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.7.6 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.7.7 Terms Used in Relation to Mechanical Items

Resilience: Ability of a material to absorb energy when deformed elastically and to release the energy upon unloading.

'Resilient': Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

'Floppy' structure or component: A structure or component that will change shape, e.g. bend, when caused to support its own weight, within a relatively short period of time such as 1 second.

'Rigid' structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilised to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilised, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognise that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 Reference Signs List

| Item | Reference number |
|---|---|
| patient | 1000 |
| patient interface | 3000 |
| seal-forming structure | 3100 |
| plenum chamber | 3200 |
| stabilising structure | 3300 |
| vent | 3400 |
| connection port | 3600 |
| forehead support | 3700 |
| RPT device (or ventilator) | 4000 |
| external housing | 4012 |
| expiration air inlet port | 4014 |
| inspiration outlet port | 4016 |

-continued

| Item | Reference number |
|---|---|
| handle | 4018 |
| upper housing case | 4020 |
| chassis | 4021 |
| lower housing case | 4022 |
| user interface display device | 4024 |
| alarm indicator light bar | 4026 |
| button | 4028 |
| expiratory portion | 4031 |
| inspiratory portion | 4033 |
| inlet air filter | 4034 |
| air flow | 4035 |
| filter assembly | 4036 |
| inlet seal | 4038 |
| inlet muffler | 4039 |
| main seal | 4040 |
| oxygen supply path | 4043 |
| grill | 4044 |
| oxygen flow | 4045 |
| oxygen connection or inlet port | 4046 |
| data connection | 4047 |
| expiratory cover | 4048 |
| electrical power connection | 4049 |
| latch | 4050 |
| switch | 4051 |
| release button | 4050R |
| battery cover | 4052 |
| grip feet | 4053 |
| oxygen sensor cover | 4054 |
| pneumatic block | 4056 |
| speaker | 4061 |
| oxygen sensor | 4064 |
| cooling fan | 4068 |
| outlet muffler | 4084 |
| safety valve | 4085 |
| printed circuit board or PCB | 4086 |
| main blower | 4104 |
| volute assembly | 4108 |
| outlet air filter | 4113 |
| return valve assembly | 4114 |
| electrovalve | 4116 |
| muffler | 4118 |
| flow control electrovalve | 4120 |
| outlet muffler | 4121 |
| inlet muffler | 4122 |
| peep blower | 4124 |
| pressure sensor | 4128 |
| flow rate sensor | 4130 |
| flow element | 4132 |
| PEEP electrovalve | 4136 |
| controllable source pressure device or pressure generator | 4140 |
| peep pressure sensor | 4142 |
| oxygen inlet port | 4144 |
| back valve | 4160 |
| delivery tube or air circuit | 4170 |
| air circuit | 4171 |
| supplemental oxygen | 4180 |
| electrical component | 4200 |
| power supply | 4210 |
| input device | 4220 |
| central controller | 4230 |
| clock | 4232 |
| therapy device controller | 4240 |
| blower | 4242 |
| motor | 4244 |
| protection circuit | 4250 |
| memory | 4260 |
| transducer or sensor | 4270 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |

-continued

| Item | Reference number |
|---|---|
| display | 4294 |
| set of algorithm modules | 4300 |
| processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| fault condition module | 4340 |
| internal battery | 4450 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| humidifier transducers or sensors | 5210 |
| pressure transducer or sensor | 5212 |
| flow rate transducer | 5214 |
| temperature sensor or transducer | 5216 |
| humidity sensor | 5218 |
| heating element | 5240 |
| humidifier controller | 5250 |
| central humidifier controller | 5251 |
| Heating element controller | 5252 |
| Air circuit controller | 5254 |
| Circuit disconnection detection method | 7000 |
| Circuit disconnection detection method | 7000A |
| Start | 7010 |
| Determine type of patient circuit | 7012 |
| Provide patient information | 7013 |
| Determine disconnection threshold | 7014 |
| Detect Q and P | 7016 |
| Calculate instantaneous disconnection parameter | 7018 |
| Compare disconnection parameter to disconnection threshold | 7020 |
| Check for disconnection event detected | 7022 |
| Set/maintain disconnection indication as false | 7024 |
| Set/maintain disconnection indication as true | 7026 |
| Start/increment timer | 7032 |
| Is timer greater than or equal to time limit | 7034 |
| Reset timer to zero | 7038 |
| Activate alarm/message | 7040 |
| Conductance threshold | 7050 |
| Threshold exceeded | 7052, 7056, 7062 |
| Disconnection event response | 7054 |
| False disconnection event response | 7058 |
| Drop below Threshold | 7060 |
| Predetermined time limit | 7064 |
| Conductance trigger threshold | 7100 |
| Inspiration phase | 7102 |
| Expiration phase | 7104 |
| Instantaneous Respiratory flow | 7106 |
| Instantaneous Airway pressure | 7108 |
| Conductance trigger point | 7110 |
| Instantaneous conductance (G) | 7112 |
| Change in conductance with time (dG/dt) | 7114 |
| Instantaneous impedance (Z) | 7116 |
| Disconnection point | 7118 |
| Flow trigger point | 7120 |
| Normal breathing phases | 7122 |

| Item | Reference number |
|---|---|
| Disconnection phase | 7124 |
| Pressure trigger point | 7130 |

The invention claimed is:

1. A respiratory therapy system configured to provide respiratory therapy to a patient breathing in successive breathing cycles including an inspiration phase and an expiration phase, the system comprising:
   a pressure generator configured to supply a flow of pressurised air, the pressure generator configured to couple with a patient interface via an air circuit to deliver the pressurised air from the pressure generator to the patient;
   a plurality of sensors configured to provide signals indicative of a pressure and a flow rate of the pressurised air flow; and
   a controller including a processor configured to:
      repeatedly detect values of instantaneous pressure and values of instantaneous flow rate from the signals from the plurality of sensors;
      repeatedly calculate instantaneous conductance values based on the values of instantaneous pressure and the values of instantaneous flow rate; and
      monitor changes in the instantaneous conductance values over time to detect an occurrence of a respiratory event within the system,
      wherein the controller determines a level of difference in an instantaneous conductance value calculated from a beginning portion of the inspiration phase and an instantaneous conductance value calculated from an end portion of the inspiration phase,
      wherein the controller is configured to adjust a rise time setting based on the level of difference.

2. A respiratory system according to claim 1, wherein the respiratory event is an obstruction.

3. A respiratory system according to claim 2, wherein the obstruction is detected when the instantaneous conductance falls below a predetermined threshold.

4. A respiratory system according to claim 2, wherein the obstruction is detected when the instantaneous conductance remains unchanged over time.

5. A respiratory system according to claim 2, wherein the obstruction occurs in the air circuit, the patient interface, or the patient's airways.

6. A respiratory system according to claim 1, wherein the respiratory event is flow starvation during a volume target mode.

7. A respiratory system according to claim 6, wherein the flow starvation is detected as a function of a profile of the instantaneous conductance values over the inspiration phase of a breathing cycle.

8. A respiratory system according to claim 7, wherein the flow starvation is detected when instantaneous conductance values are higher at an early-to-mid-inspiration portion of the inspiration phase compared to an end portion of the inspiration phase.

9. A respiratory system according to claim 6, wherein the flow starvation is detected by a comparison of (a) an instantaneous conductance value calculated from the inspiration phase of a breathing cycle and (b) a conductance threshold.

10. A respiratory system according to claim 9, wherein the flow starvation is detected when the instantaneous conductance value calculated from the inspiration phase of the breathing cycle exceeds the conductance threshold.

11. A respiratory system according to claim 1, wherein upon detection of the respiratory event, the controller is configured to activate a message to indicate the occurrence of the respiratory event.

12. A respiratory therapy system configured to provide respiratory therapy to a patient breathing in successive breathing cycles including an inspiration phase and an expiration phase, the system comprising:
   a pressure generator configured to supply a flow of pressurised air, the pressure generator configured to couple with a patient interface via an air circuit to deliver the pressurised air from the pressure generator to the patient;
   a plurality of sensors configured to provide signals indicative of a pressure and a flow rate of the pressurised air flow; and
   a controller including a processor configured to:
      repeatedly detect values of instantaneous pressure and values of instantaneous flow rate from the signals from the plurality of sensors;
      repeatedly calculate instantaneous conductance values based on the values of instantaneous pressure and the values of instantaneous flow rate; and
      monitor changes in the instantaneous conductance values over time to monitor the respiratory therapy,
      wherein the controller determines a level of difference in an instantaneous conductance value calculated from a beginning portion of the inspiration phase and an instantaneous conductance value calculated from an end portion of the inspiration phase,
      wherein the controller is configured to adjust a rise time setting based on the level of difference.

13. A respiratory system according to claim 12, wherein the controller is configured to adjust a peak inspiratory flow setting based on the level of difference.

14. A respiratory system according to claim 12, wherein the controller is configured to monitor the instantaneous conductance value over time to determine the inspiration phase and the expiration phase of one or more breathing cycles.

15. A respiratory system according to claim 12, wherein the controller is configured to monitor the instantaneous conductance value over time to detect an insufficient vent flow condition.

16. A respiratory system according to claim 15, wherein the controller is configured to detect the insufficient vent flow condition as an anomalously low conductance value compared to recent baseline conductance values.

17. A respiratory therapy system configured to provide respiratory therapy to a patient breathing in successive breathing cycles including an inspiration phase and an expiration phase, the system comprising:
   a pressure generator configured to supply a flow of pressurised air, the pressure generator configured to couple with a patient interface via an air circuit to deliver the pressurised air from the pressure generator to the patient;
   a plurality of sensors configured to provide signals indicative of a pressure and flow of the pressurised air flow; and a controller including a processor configured to:
repeatedly detect values of instantaneous pressure and values of instantaneous flow rate from the signals from the plurality of sensors;
repeatedly calculate instantaneous impedance values based on the values of instantaneous pressure and the values of instantaneous flow rate; and
monitor changes in the instantaneous impedance values over time to detect an occurrence of a respiratory event within the system,
wherein the controller determines a level of difference in an instantaneous impedance value calculated from a beginning portion of the inspiration phase and an instantaneous impedance value calculated from an end portion of the inspiration phase,
wherein the controller is configured to adjust a rise time setting based on the level of difference.

18. A respiratory system according to claim 17, wherein the respiratory event is an obstruction.

19. A respiratory system according to claim 18, wherein the obstruction is detected when the instantaneous impedance exceeds a predetermined threshold.

20. A respiratory system according to claim 18, wherein the obstruction is detected when the instantaneous impedance remains substantially unchanged over time.

21. A respiratory system according to claim 18, wherein the obstruction occurs in the air circuit, the patient interface, or the patient's airways.

22. A respiratory system according to claim 17, wherein the respiratory event is flow starvation during a volume target mode.

23. A respiratory system according to claim 22, wherein the flow starvation is detected as a function of a profile of instantaneous impedance values over an inspiratory portion of a breathing cycle.

24. A respiratory system according to claim 23, wherein the flow starvation is detected when instantaneous impedance values are lower at an early to mid-inspiration portion of the inspiration phase compared to an end portion of the inspiration phase.

25. A respiratory system according to claim 22, wherein the flow starvation is detected by comparison of instantaneous impedance values calculated from the inspiration phase of a breathing cycle with an impedance threshold.

26. A respiratory system according to claim 25, wherein the flow starvation is detected when the instantaneous impedance values calculated from the inspiration phase of the breathing cycle fall below the impedance threshold.

27. A respiratory system according to claim 17, wherein upon detection of the respiratory event the controller is configured to provide a message to indicate the occurrence of the respiratory event.

28. A respiratory therapy system configured to provide respiratory therapy to a patient breathing in successive breathing cycles including an inspiration phase and an expiration phase, the system comprising:
a pressure generator configured to supply a flow of pressurised air, the pressure generator configured to couple with a patient interface via an air circuit to deliver the pressurised air from the pressure generator to the patient;
a plurality of sensors configured to provide signals indicative of a pressure and a flow rate of the pressurised air flow; and
a controller including a processor configured to:
repeatedly detect values of instantaneous pressure and instantaneous flow rate from the signals from the plurality of sensors;
repeatedly calculate instantaneous impedance values based on the values of instantaneous pressure and the values of instantaneous flow rate; and
monitor changes in the instantaneous impedance values over time to monitor the respiratory therapy,
wherein the controller determines a level of difference in an instantaneous impedance value calculated from a beginning portion of the inspiration phase and an instantaneous impedance value calculated from an end portion of the inspiration phase,
wherein the controller is configured to adjust a rise time setting based on the level of difference.

29. A respiratory system according to claim 28, wherein the controller is configured to adjust a peak inspiratory flow setting based on the level of difference.

30. A respiratory system according to claim 28, wherein the controller is configured to monitor the instantaneous impedance value over time to determine the inspiration phase and the expiration phase of each breathing cycle.

31. A respiratory system according to claim 28, wherein the controller is configured to monitor the instantaneous impedance value over time to detect an insufficient vent flow condition.

32. A respiratory system according to claim 31, wherein the controller is configured to detect an insufficient vent flow condition as an anomalously high impedance value compared to recent baseline impedance values.

* * * * *